(12) United States Patent
Nakamura et al.

(10) Patent No.: US 10,591,749 B2
(45) Date of Patent: Mar. 17, 2020

(54) MEDICAL DEVICE, COMBINATION OF COATING SOLUTIONS, AND METHOD FOR PRODUCING MEDICAL DEVICE

(75) Inventors: Masataka Nakamura, Otsu (JP); Rumiko Kitagawa, Otsu (JP); Ryuta Tamiya, Otsu (JP)

(73) Assignee: Toray Industries, Inc., Tokyo (JP)

( * ) Notice: Subject to any disclaimer, the term of this patent is extended or adjusted under 35 U.S.C. 154(b) by 397 days.

(21) Appl. No.: 14/238,010

(22) PCT Filed: Aug. 10, 2012

(86) PCT No.: PCT/JP2012/070435
§ 371 (c)(1),
(2), (4) Date: Feb. 10, 2014

(87) PCT Pub. No.: WO2013/024799
PCT Pub. Date: Feb. 21, 2013

(65) Prior Publication Data
US 2014/0198294 A1    Jul. 17, 2014

(30) Foreign Application Priority Data

Aug. 17, 2011  (JP) ................................. 2011-178649
Aug. 17, 2011  (JP) ................................. 2011-178652
Aug. 17, 2011  (JP) ................................. 2011-178653

(51) Int. Cl.
G02C 7/04        (2006.01)
A61L 27/52       (2006.01)
(Continued)

(52) U.S. Cl.
CPC .............. *G02C 7/049* (2013.01); *A61L 27/18* (2013.01); *A61L 27/34* (2013.01); *A61L 27/50* (2013.01);
(Continued)

(58) Field of Classification Search
None
See application file for complete search history.

(56) References Cited

U.S. PATENT DOCUMENTS 4,277,595 A    7/1981  Deichert et al.
5,143,660 A    9/1992  Hamilton et al.
(Continued)

FOREIGN PATENT DOCUMENTS

CN    1327002 A    12/2001
CN    1993151      7/2007
(Continued)

OTHER PUBLICATIONS

Extended European Search Report dated Jun. 1, 2015 for European Application No. 1282514.0.
(Continued)

*Primary Examiner* — Leslie Lopez
(74) *Attorney, Agent, or Firm* — RatnerPrestia

(57) ABSTRACT

Disclosed is a medical device having an elastic modulus of 100 kPa or more and 2,000 kPa or less, a water content of 10% by mass or less, a tensile elongation of 50% or more and 3,000% or less, and a dynamic contact angle (advancing angle) relative to a borate buffer of 80° or less. The present invention can significantly reduce or avoid a phenomenon of adhesion to a surface when contacted with a surface outside or inside the body, which has hitherto been regarded as a problem in a conventional medical device.

9 Claims, 4 Drawing Sheets

(51) Int. Cl.
  *A61L 27/34*   (2006.01)
  *A61L 27/18*   (2006.01)
  *A61L 27/50*   (2006.01)
  *G02C 7/16*    (2006.01)
  *B29D 11/00*   (2006.01)
  *G02B 1/04*    (2006.01)

(52) U.S. Cl.
  CPC ........ *A61L 27/52* (2013.01); *B29D 11/00865* (2013.01); *G02B 1/043* (2013.01); *G02C 7/165* (2013.01); *A61L 2400/10* (2013.01); *A61L 2420/06* (2013.01); *A61L 2430/16* (2013.01); *G02C 7/046* (2013.01)

(56) References Cited

U.S. PATENT DOCUMENTS

| | | | |
|---|---|---|---|
| 5,610,252 A | 3/1997 | Bambury | |
| 5,760,100 A * | 6/1998 | Nicolson | G02C 7/049 351/159.33 |
| 6,312,706 B1 * | 11/2001 | Lai | C08F 299/06 424/422 |
| 6,896,926 B2 | 5/2005 | Qiu et al. | |
| 2002/0006521 A1 | 1/2002 | Shimoyama et al. | |
| 2002/0021409 A1 | 2/2002 | Marmo | |
| 2002/0075447 A1 | 6/2002 | Andino et al. | |
| 2003/0065051 A1 | 4/2003 | Winterton et al. | |
| 2003/0117579 A1 | 6/2003 | Morris et al. | |
| 2003/0151718 A1 | 8/2003 | Marmo | |
| 2004/0054106 A1 * | 3/2004 | Ito | A61L 27/18 526/279 |
| 2004/0067365 A1 * | 4/2004 | Qiu | A61L 27/34 428/411.1 |
| 2004/0192872 A1 | 9/2004 | Iwata et al. | |
| 2005/0033420 A1 * | 2/2005 | Christie | A61B 3/152 623/5.12 |
| 2005/0254002 A1 | 11/2005 | Dukes et al. | |
| 2007/0229757 A1 | 10/2007 | McCabe | |
| 2008/0154196 A1 | 6/2008 | Moh | |
| 2008/0174035 A1 | 7/2008 | Winterton | |
| 2009/0104474 A1 | 4/2009 | Schwartz et al. | |
| 2009/0171026 A1 | 7/2009 | Fujisawa et al. | |
| 2011/0178507 A1 | 7/2011 | Bracken | |
| 2011/0294914 A1 | 12/2011 | Rathore et al. | |
| 2012/0200821 A1 | 8/2012 | Arai | |
| 2012/0314183 A1 | 12/2012 | Nakamura et al. | |
| 2014/0198295 A1 | 7/2014 | Fujisawa et al. | |

FOREIGN PATENT DOCUMENTS

| | | | |
|---|---|---|---|
| CN | 100538439 | 9/2009 | |
| CN | 102131531 | 7/2011 | |
| CN | 102202875 | 9/2011 | |
| JP | 56-51715 | 5/1891 | |
| JP | 54-81363 | 6/1979 | |
| JP | S 56-161436 | 12/1981 | |
| JP | 59-229524 | 12/1984 | |
| JP | 02-1888717 | 7/1990 | |
| JP | H 055861 | 1/1993 | |
| JP | H 09-502542 | 3/1997 | |
| JP | H 11-242191 | 9/1999 | |
| JP | 2000-191667 | 7/2000 | |
| JP | 2000-230021 | 8/2000 | |
| JP | 2002-501211 | 1/2002 | |
| JP | 2002-182166 | 6/2002 | |
| JP | 2004-510199 | 4/2004 | |
| JP | 2005-500554 | 1/2005 | |
| JP | 2005-508708 | 4/2005 | |
| JP | 2005089654 A | 4/2005 | |
| JP | 2005-538418 | 12/2005 | |
| JP | 2006-515688 | 6/2006 | |
| JP | 2006-309101 | 11/2006 | |
| JP | 2007-526946 | 9/2007 | |
| JP | 2007-537492 | 12/2007 | |
| JP | 2009-540369 | 11/2009 | |
| JP | 2011-500216 | 1/2011 | |
| JP | 2011-511850 | 4/2011 | |
| TW | M388011 | 9/2010 | |
| WO | 9724639 A1 | 12/1996 | |
| WO | WO 01/044861 | 6/2001 | |
| WO | WO 01/57118 A2 * | 8/2001 | ............... C08J 7/00 |
| WO | 2010062520 | 6/2010 | |
| WO | 2011048953 | 4/2011 | |

OTHER PUBLICATIONS

French, K. et al., "A decade with silicone hydrogels: Part 1," Optometry Today, Aug. 15, 2008, pp. 42-46.
International Search Report for PCT International Application No. PCT/JP2012/070435 dated Nov. 20, 2012.
Extended European Search Report for European Application No. 191969088, dated Dec. 4, 2019, 8 pages.

* cited by examiner

MEDICAL DEVICE, COMBINATION OF COATING SOLUTIONS, AND METHOD FOR PRODUCING MEDICAL DEVICE

CROSS-REFERENCE TO RELATED APPLICATIONS

This is the U.S. National Phase application of PCT International Application No. PCT/JP2012/070435, filed Aug. 10, 2012, and claims priority to Japanese Patent Application No. 2011-178649, filed Aug. 17, 2011, and Japanese Patent Application No. 2011-178652, filed Aug. 17, 2011, and Japanese Patent Application No. 2011-178653, filed Aug. 17, 2011, the disclosures of each of these applications being incorporated herein by reference in their entireties for all purposes.

FIELD OF THE INVENTION

The present invention relates to a medical device, a combination of coating solutions, and a method for producing a medical device.

BACKGROUND OF THE INVENTION

An example of a soft medical device includes a soft contact lens which is a commercially available soft lens for eye. A hydrogel material having a water content of about 25 to 80% is commonly used in the commercially available soft contact lens. However, since the low water content soft contact lens made of the hydrogel material contains water, there arises a phenomenon in which water is vaporized from the contact lens. Thereby, a certain proportions of contact lens wearers felt dry more strongly as compared with the case of the naked eye, and thus felt uncomfortable. Among these contact lens wearers, some persons complained a condition of so-called contact lens-related dry eye. Since a water-containing soft contact lens made of a hydrogel material is likely to be contaminated with components in a lacrimal fluid and also contains a large amount of water, there was also a risk of the growth of bacteria.

There has been known, as a highly oxygen permeable low water content soft contact lens, for example, a silicone rubber lens obtained by a method of adding a platinum-based catalyst to a mixture of polydimethylsiloxane in which both ends of the molecular chain are blocked with a vinyl-methylsilyl group, and methyl hydrogen polysiloxane, followed by heat-curing using a molding method (see, for example, Patent Literature 1).

Patent Literatures 2 to 7 also disclose a highly oxygen permeable contact lens material composed mainly of polysiloxane having a plurality of polymerizable functional groups. Of these, Patent Literature 6 discloses a contact lens material made of a polymer obtained by polymerizing a difunctional organosiloxane macromer alone, or a polymer obtained by copolymerizing a difunctional organosiloxane macromer with the other monomers, and also discloses an acrylic acid fluoroalkyl ester or a methacrylic acid fluoroalkyl ester, and an acrylic acid alkyl ester or a methacrylic acid alkyl ester as a monomer to be used in copolymerization.

Meanwhile, the following problems also lie in a conventional highly oxygen permeable low water content soft contact lens. A silicone rubber lens has such a drawback that a hydrophilized layer formed so as to improve hydrophobicity of the surface of the lens is peeled, or adhesion of the lens to the cornea occurs due to too large resilience, and thus the silicone rubber lens had not widely been put into practice.

A material composed mainly of polysiloxane having a plurality of polymerizable functional groups has high oxygen permeability and also has flexibility, and the material is considered to be one of materials which are suitable for a contact lens. However, since tackiness is left on the surface of the lens after polymerization, the lens may adhere to the cornea and is also insufficient in balance between flexibility of the lens and mechanical properties such as folding resistance.

There have been known various methods for modification of a surface of a soft lens for eye. Among these methods, there is known a method in which layers of two or more kinds of polymer materials are coated and accumulated in a layer by layer fashion (see, for example, Patent Literatures 8 to 10). Among these methods, a method of alternately forming layers made of two polymer materials, each having an opposite electric charge, in a layer by layer fashion by coating is called an LbL method, and it is considered that each layer of the material is noncovalently bonded to the other layer made of a different material.

However, the highly oxygen permeable soft lens for eye in which utility of the method disclosed in Patent Literature 1 is clearly shown is made only of a silicone hydrogel material, and utility to the low water content soft lens for eye has not been known. Conventional LbL coating was carried out to obtain a multi-layered structure constituted from about 4 to 20 layers, and thus the production process may increase, to cause an increase in production costs.

In the above-mentioned soft contact lens, there has been known a contact lens in which the color or size of iris portions of lens wearers can be changed by forming an iris pattern, which is an iris-like and approximately cyclic mask, to the lens (see, for example, Patent Literatures 11 and 12). There has also been known a contact lens in which formation of a hole (pinhole) at approximately center of the iris pattern enables clear vision irrespective of hyperopia, myopia, and presbyopia (see, for example, Patent Literatures 13 and 14). However, the same problems as those mentioned above arose when the iris pattern is formed to the contact lens (low water content soft device for eye) produced by the above-mentioned method.

In the above-mentioned soft contact lens, there has also been known a contact lens in which formation of a lacrimal fluid exchange-promoting pattern on the contact lens enables exchange of a lacrimal fluid during wearing of lenses (see, for example, Patent Literatures 15 to 18). However, the same problems as those mentioned above arose when the lacrimal fluid exchange-promoting pattern is formed to the contact lens produced by the above-mentioned method.

PATENT LITERATURE

[Patent Literature 1]
 Japanese Unexamined Patent Publication (Kokai) No. 54-81363
[Patent Literature 2]
 Japanese Unexamined Patent Publication (Kokai) No. 54-24047
[Patent Literature 3]
 Japanese Unexamined Patent Publication (Kokai) No. 56-51715
[Patent Literature 4]
 Japanese Unexamined Patent Publication (Kokai) No. 59-229524

[Patent Literature 5]
 Japanese Unexamined Patent Publication (Kokai) No. 2-188717
[Patent Literature 6]
 Japanese Unexamined Patent Publication (Kokai) No. 5-5861
[Patent Literature 7]
 Kohyo (National Publication of Translated Version) No. 2007-526946
[Patent Literature 8]
 Kohyo (National Publication of Translated Version) No. 2002-501211
[Patent Literature 9]
 Kohyo (National Publication of Translated Version) No. 2005-538418
[Patent Literature 10]
 Kohyo (National Publication of Translated Version) No. 2009-540369
[Patent Literature 11]
 Japanese Unexamined Patent Publication (Kokai) No. 2006-309101
[Patent Literature 12]
 Kohyo (National Publication of Translated Version) No. 2007-537492
[Patent Literature 13]
 Kohyo (National Publication of Translated Version) No. 9-502542
[Patent Literature 14]
 Japanese Unexamined Patent Publication (Kokai) No. 11-242191
[Patent Literature 15]
 Japanese Unexamined Patent Publication (Kokai) No. 56-161436
[Patent Literature 16]
 Kohyo (National Publication of Translated Version) No. 2004-510199
[Patent Literature 17]
 Kohyo (National Publication of Translated Version) No. 2005-500554
[Patent Literature 18]
 Kohyo (National Publication of Translated Version) No. 2006-515688

SUMMARY OF THE INVENTION

Meanwhile, like the above-mentioned low water content soft lens for eye, a low water content soft medical device, which is used on a surface outside the body or used inside the body, had the same problems. Particularly in a medical device which is contacted with a body surface including a body fluid or the like, or a medical device which is introduced into the body, there arises a phenomenon of adhesion of the medical device to the surface when contacted with a liquid such as a body fluid, and thus there is a need to maintain the above-mentioned mechanical properties and low water content and to improve lubricity.

The present invention has been made in view of the above problems and aims to provide a medical device which can maintain mechanical properties and low water content, and also can significantly reduce or avoid a phenomenon of adhesion to the surface when contacted with a body surface or a surface inside the body, or feeling of adhesion to the cornea; a combination of coating solutions for applying to this medical device; and a method for producing a medical device.

The present invention also aims to provide a low water content soft contact lens which enables satisfactory lacrimal fluid exchange. The present invention further aims to produce an excellent low water content soft contact lens by a simple process at low costs.

The medical device according to the present invention includes the following aspects.

[A1] A medical device having an elastic modulus of 100 kPa or more and 2,000 kPa or less, preferably 200 kPa or more and 1,200 kPa or less, a water content of 10% by mass or less, a tensile elongation of 50% or more and 3,000% or less, preferably 150% or more and 3,000% or less, and a dynamic contact angle (advancing angle) relative to a borate buffer of 80° or less.

[A2] The medical device according to [A1], wherein a surface friction coefficient ratio (Qa) in a state of being wetted with a borate buffer is 2 or less, provided that Qa=MIUa/MIUo: where MIUa represents a coefficient of surface friction between the medical device and a smooth quartz glass plate in a state of being wetted with the borate buffer; and MIUo represents a coefficient of surface friction between "ACUVUE®OASYS" and a smooth quartz glass plate in a state of being wetted with the borate buffer. "ACUVUE® OASYS" is a contact lens made of a material registered under the name of Senofilcon A in the United States Adopted Names, and preferably a contact lens equivalent to the product distributed in Japan in August 2011.

[A3] The medical device according to [A1], wherein a surface friction coefficient ratio (Qb) in a state of being wetted with a saline is 3 or less, provided that Qb=MIUb/MIUo: where MIUb represents a coefficient of surface friction between the medical device and a smooth quartz glass plate in a state of being wetted with the saline; and MIUo represents a coefficient of surface friction between "ACUVUE® OASYS" and a smooth quartz glass plate in a state of being wetted with the borate buffer.

In the above, the surface friction coefficient ratio (Qb) in a state of being wetted with a saline is preferably 2 or less.

[A4] The medical device according to [A1], wherein a difference (Qb−Qa) between a surface friction coefficient ratio (Qb) in a state of being wetted with a saline and a surface friction coefficient ratio (Qa) in a state of being wetted with a borate buffer is 1.6 or less, provided that Qa=MIUa/MIUo, and Qb=MIUb/MIUo:
where MIUa represents a coefficient of surface friction between the medical device and a smooth quartz glass plate in a state of being wetted with the borate buffer;
MIUb represents a coefficient of surface friction between the medical device and a smooth quartz glass plate in a state of being wetted with the saline; and MIUo represents a coefficient of surface friction between "ACUVUE® OASYS" and a smooth quartz glass plate in a state of being wetted with the borate buffer.

[A5] The medical device according to any one of [A1] to [A4], including a base material, wherein a layer made of an acidic polymer and a basic polymer is formed on at least a part of a surface of the base material.

[A6] The medical device according to [A5], wherein the base material contains, as main components, a polymer of the following component A, or a copolymer of the following components A and B:
 component A: a polysiloxane compound which has a plurality of polymerizable functional groups per molecule, and also has a number average molecular weight of 6,000 or more, and
 component B: a polymerizable monomer having a fluoroalkyl group.

[A7] The medical device according to [A6], wherein the component B is a (meth)acrylic acid fluoroalkyl ester.

[A8] The medical device according to any one of [A5] to [A7], wherein the layer made of an acidic polymer and a basic polymer is formed by performing the treatment with an acidic polymer solution once or twice, and the treatment with a basic polymer solution once or twice, that is, three times in total.

[A9] The medical device according to any one of [A5] to [A7], wherein the layer made of an acidic polymer layer and a basic polymer is formed by performing a treatment with two kinds of acidic polymer solutions twice and a treatment with a basic polymer solution once.

[A10] The medical device according to any one of [A5] to [A9], wherein at least one of the acidic polymer and the basic polymer, which form the layer made of an acidic polymer and a basic polymer, is a polymer having a group selected from a hydroxyl group and an amide group.

[A11] The medical device according to any one of [A1] to [A10], wherein an oxygen permeability [(cm$^2$/sec) mLO$_2$/(mL·hPa)] is $113 \times 10^{-11}$ to $1,130 \times 10^{-11}$.

[A12] The medical device according to any one of [A1] to [A11], which is a lens for eye.

[A13] A method for producing a medical device in which LbL coating is applied to a base material through n steps in total from a first step of bringing a base material into contact with a first solution containing a first polymer to thereby noncovalently apply the first polymer onto the base material to an nth step (n is an integer of 2 or more) of bringing the base material into contact with an nth solution containing an nth polymer to thereby noncovalently apply the nth polymer onto the base material, thus obtaining the medical device, the method including: bringing any one (k−1)th solution (k is an integer of 2 or more and n or less) of the first solution to the nth solution into contact with a quartz resonator sensor for quartz crystal microbalance (QCM), and quickly washing the quartz resonator sensor with pure water, followed by drying and further the measurement of a resonance frequency using the QCM to obtain a measured value $F_{k-1}$, subsequently bringing a kth solution into contact with this quartz resonator sensor, and quickly washing the quartz resonator sensor with pure water, followed by drying and further the measurement of a resonance frequency using the QCM to obtain a measured value $F_k$, and using the (k−1)th solution and the kth solution in which the $F_k$−the $F_{k-1}$ is 1,500 or more, wherein a quartz resonator sensor (resonance frequency of 9 MHz, AT-cut, gold electrode) is used as the quartz resonator sensor, and the measurement is performed at a fundamental frequency of 27 MHz at room temperature (about 25° C.) using the QCM.

[A14] A combination of coating solutions for applying LbL coating to a medical device, including a first solution to an nth solution, wherein a coating solution containing a first polymer for noncovalently applying the first polymer onto a base material is used as a first solution, and a coating solution containing a kth polymer for noncovalently applying the kth polymer onto a base material is used as a kth solution (k is an integer of 2 or more and n or less, n is an integer of 2 or more), and when a quartz resonator sensor for quartz crystal microbalance (QCM) is immersed in a first solution at 25° C. for 30 minutes, and then the quartz resonator sensor is quickly washed with pure water and dried, followed by the measurement of a resonance frequency using the QCM to obtain a measured value $F_1$, and subsequently, the quartz resonator sensor is immersed in a second solution containing a second polymer at 25° C. for 30 minutes immersed, and then the quartz resonator sensor is quickly washed with pure water and dried, followed by the measurement of a resonance frequency using the QCM to obtain a measured value $F_2$, and the measurement to a measured value $F_n$ was sequentially performed in the same manner, any one $F_k$−$F_{k-1}$ becomes 1,500 or more, and wherein a quartz resonator sensor (resonance frequency of 9 MHz, AT-cut, gold electrode) is used as the quartz resonator sensor, and the measurement is performed at a fundamental frequency of 27 MHz at room temperature (about 25° C.) using the QCM.

The present invention also includes the following aspects.

[B1] A low water content soft device for eye to be worn in the eye, having an elastic modulus of 100 kPa or more and 2,000 kPa or less, a water content of 10% by mass or less, a tensile elongation of 50% or more and 3,000% or less, and a dynamic contact angle (advancing angle) relative to a borate buffer of 80° or less, an iris-like pattern being formed on at least a part of the low water content soft device for eye.

[B2] A low water content soft device for eye, wherein a layer made of an acidic polymer and a basic polymer is formed on at least a part of the low water content soft device for eye, an iris-like pattern being formed on at least a part of the low water content soft device for eye.

[B3] The low water content soft device for eye according to [B2], wherein the base material contains, as main components, a polymer of the following component A, or a copolymer of the following components A and B:

component A: a polysiloxane compound which has a plurality of polymerizable functional groups per molecule, and also has a number average molecular weight of 6,000 or more, and component B: a polymerizable monomer having a fluoroalkyl group.

[B4] The low water content soft device for eye according to [B3], wherein the component A is a polysiloxane compound having two polymerizable functional groups per molecule.

[B5] The low water content soft device for eye according to [B4], wherein the component A is a polysiloxane compound represented by the following formula (A1):

[Chemical Formula 1]

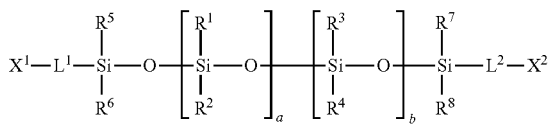

(A1)

wherein $X^1$ and $X^2$ each independently represents a polymerizable functional group; $R^1$ to $R^8$ each independently represents a substituent selected from hydrogen, an alkyl group having 1 to 20 carbon atoms, a phenyl group, and a fluoroalkyl group having 1 to 20 carbon atoms; $L^1$ and $L^2$ each independently represents a divalent group; and a and b each independently represents an integer of 0 to 1,500, provided that a and b are not simultaneously 0.

[B6] The low water content soft device for eye according to any one of [B3] to [B5], wherein the low water content soft base material contains 5% by mass or more of silicon atoms.

[B7] The low water content soft device for eye according to [B3], wherein the component B is a (meth)acrylic acid fluoroalkyl ester.

[B8] The low water content soft device for eye according to any one of [B2] to [B7], wherein the layer made of an acidic polymer and a basic polymer contains one or more kinds of acidic polymers and one or more kinds of basic polymers.

[B9] The low water content soft device for eye according to any one of [B2] to [B8], wherein the layer made of an acidic polymer and a basic polymer is formed by performing a treatment with an acidic polymer solution once or twice, and a treatment with a basic polymer solution once or twice, that is, three times in total.

[B10] The low water content soft device for eye according to any one of [B2] to [B8], wherein the layer made of an acidic polymer layer and a basic polymer is formed by performing a treatment with two kinds of acidic polymer solutions twice and a treatment with a basic polymer solution once.

[B11] The low water content soft device for eye according to any one of [B2] to [B10], wherein at least one of the acidic polymer and the basic polymer, which form the layer made of an acidic polymer and a basic polymer, is a polymer having a group selected from a hydroxyl group and an amide group.

[B12] The low water content soft device for eye according to any one of [B1] to [B11], wherein the pattern is a light shielding pattern having a circular ring shape, and an optical pupil having a diameter of 2.0 mm or less is formed in the center of the pattern.

[B13] The low water content soft device for eye according to any one of [B1] to [B12], wherein the pattern covers a surface of an iris to thereby pseudo-color the iris.

The present invention also includes the following aspects.

[C1] A low water content soft contact lens to be worn in the eye, wherein a pattern promoting exchange of lacrimal fluid between the low water content soft contact lens and the eye is formed.

[C2] The low water content soft contact lens according to [C1], wherein the pattern is at least one selected from a through hole, a groove, and a pleats structure.

[C3] The low water content soft contact lens according to [C2], wherein the pattern is the through hole.

[C4] The low water content soft contact lens according to any one of [C1] to [C3], including a base material, wherein a layer made of an acidic polymer and a basic polymer is formed on at least a part of a surface of the base material.

[C5] The low water content soft contact lens according to [C4], wherein the base material contains, as main components, a polymer of the following component A, or a copolymer of the following components A and B:
component A: a polysiloxane compound which has a plurality of polymerizable functional groups per molecule, and also has a number average molecular weight of 6,000 or more, and
component B: a polymerizable monomer having a fluoroalkyl group.

[C6] The low water content soft contact lens according to [C5], wherein the component B is a (meth)acrylic acid fluoroalkyl ester.

[C7] The low water content soft contact lens according to any one of [C4] to [C6], wherein the layer made of an acidic polymer and a basic polymer is formed by performing a treatment with an acidic polymer solution once or twice, and a treatment with a basic polymer solution once or twice, that is, three times in total.

[C8] The low water content soft contact lens according to any one of [C4] to [C6], wherein the layer made of an acidic polymer layer and a basic polymer is formed by performing a treatment with two kinds of acidic polymer solutions twice and a treatment with a basic polymer solution once.

[C9] The low water content soft contact lens according to any one of [C4] to [C8], wherein at least one of the acidic polymer and the basic polymer, which form the layer made of an acidic polymer and a basic polymer, is a polymer having a group selected from a hydroxyl group and an amide group.

[C10] A method for producing a low water content soft contact lens, which includes molding a base material using a mold made of a resin, and then perforating the base material before separating the base material from the mold made of a resin.

A medical device according to the present invention, a coating liquid for applying to this medical device, a combination of coating solutions, and a method for producing a medical device can maintain mechanical properties and low water content, and also can significantly reduce or avoid a phenomenon of adhesion to a surface when contacted with a surface outside or inside the body, or feeling sticky to the cornea. The medical device of the present invention can reduce a risk of the growth of bacteria because of its low water content. According to the present invention, it is possible to provide a medical device, which has high oxygen permeability and is excellent in water wettability, and which is flexible and is therefore excellent in comfort, and is also excellent in mechanical properties such as folding resistance. The medical device of the present invention also has a merit capable of producing by a simple process at low costs.

A low water content soft contact lens as an aspect of the present invention, and a method for producing the same enable the above-mentioned effects and satisfactory lacrimal fluid exchange, and thus it is possible to expect the effect of maintaining soundness of eyes. The low water content soft contact lens as an aspect of the present invention also has a merit capable of producing by a simple process at low costs.

DETAILED DESCRIPTION OF EMBODIMENTS OF THE INVENTION

Figure 1:
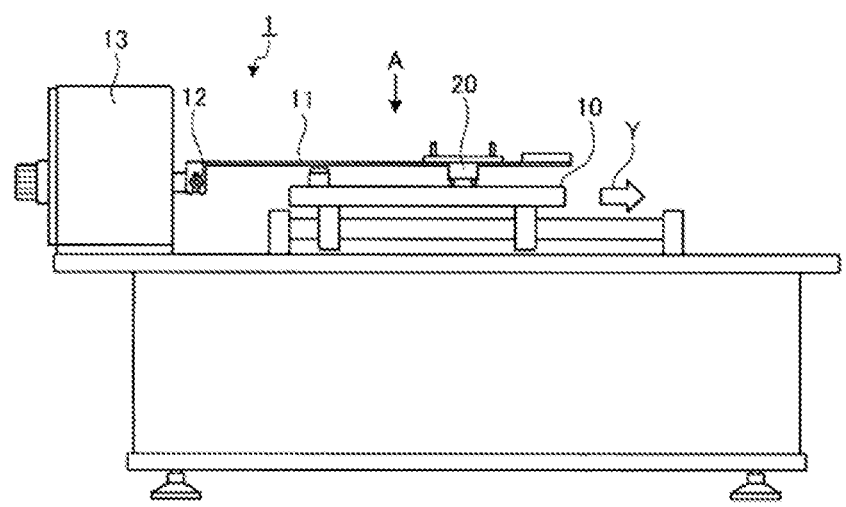
FIG. 1 is a schematic view showing an apparatus for measuring a surface friction coefficient of a sample of a medical device according to Example of the present invention, provided that FIG. 1 shows a state where a measurement jig and a friction block are fitted as standard equipment.

Mode for carrying out the present invention will be described in detail below. The present invention is not limited to the following embodiments.

The medical device of the present invention is a device which is intended to be contacted with a body surface including a body fluid or the like, or a device which is introduced into the body and includes, for example, a contact lens (lens for eye), an endoscope, a catheter, an infusion tube, a gas transfer tube, a stent, a sheath, a cuff, a tube connector, an access port, a drainage bag, a blood circuit, a skin material, and a drug carrier.

The medical device of the present invention is a low water content medical device which preferably has a water content of 10% by mass or less. The medical device of the present invention is a medical device which preferably has a tensile elastic modulus of 10 MPa or less. The water content is given from the mass in a dry state of a specimen (mass in a dry state) and the mass in the case of wiping off surface moisture of a specimen in a state of being wetted with a borate buffer (mass in a wet state) by [((mass in a wet state)−(mass in a dry state))/(mass in a wet state)].

The medical device of the present invention has features such as less feeling of dryness of patients while being contacted with a surface of the living body (eye in the case of a lens for eye) and excellent comfort because of its low water content. The medical device of the present invention has a merit such as low risk of the growth of bacteria because of its low water content. The water content is more preferably κ% or less, still more preferably 2% or less, and most preferably 1% or less. Too high water content is not preferred since feeling of dryness of eyes of patients may increase or risk of the growth of bacteria may become higher.

Tensile elastic modulus of the medical device of the present invention is 100 kPa or more, preferably 200 kPa or more, more preferably 250 kPa or more, and still more preferably 300 kPa or more. Tensile elastic modulus of the medical device of the present invention is 2,000 kPa or less, preferably 1,200 kPa or less, more preferably 1,000 kPa or less, still more preferably 800 kPa or less, yet more preferably 700 kPa or less, and most preferably 600 kPa or less. When the tensile elastic modulus is too small, it may become difficult to handle since the lens is too soft. When the tensile elastic modulus is too large, comfort may become worse since the device is too hard. Since satisfactory comfort is obtained when the tensile elastic modulus becomes 2,000 kPa, and preferably 1,200 kPa or less, the tensile elastic modulus is within a range of 100 kPa or more and 2,000 kPa or less, and preferably 200 kPa or more and 1,200 kPa or less. The tensile elastic modulus is measured by a specimen in a state of being wetted with a borate buffer.

Tensile elongation (elongation at break) of the medical device of the present invention is 50% or more, preferably 150% or more, more preferably 170% or more, still more preferably 200% or more, even more preferably 300% or more, and yet more preferably 400% or more. Tensile elongation of the medical device of the present invention is 3,000% or less, preferably 2,500% or less, still more preferably 2,000% or less, even more preferably 1,500% or less, and most preferably 1,000% or less. It is not preferred that the tensile elongation is too small since the medical device is likely to be broken. It is not preferred that the tensile elongation is too large since the medical device tends to be deformed. The tensile elongation is measured by a specimen in a state of being wetted with a borate buffer.

It is preferable that medical device of the present invention is excellent in wettability of a surface, from the viewpoint of compatibility with the living body (biocompatibility), and dynamic contact angle (advancing angle, immersion rate of 0.1 mm/sec) is preferably 80° or less, more preferably 75° or less, and still more preferably 70° or less. From the viewpoint of preventing adhesion to the cornea of the patient, the dynamic contact angle is preferably lower, and is preferably 65° or less, more preferably 60° or less, still more preferably 55° or less, even more preferably 50° or less, yet more preferably 45° or less, and most preferably 40° or less. The dynamic contact angle is measured relative to a borate buffer using a specimen in a state of being wetted with the borate buffer.

It is preferable that the medical device of the present invention is excellent in wettability of a surface, from the viewpoint of compatibility with the living body. From the viewpoint of preventing adhesion to a surface of the living body (cornea in the case of a lens for eye) of the patient, liquid film retention time of a surface of a medical device is preferably long. As used herein, the liquid film retention time is the time during which a liquid film on a surface of a medical device (a diameter direction in the case of a lens for eye) is held without being broken, when the medical device immersed in a borate buffer is pulled up from the borate buffer and then held in air so that a diameter direction becomes vertical. The liquid film retention time is preferably 5 seconds or more, more preferably 10 seconds or more, and most preferably 20 seconds or more. As used herein, the diameter is the diameter of a circle composed of an edge portion of a lens. The liquid film retention time is measured using a sample in a state of being wetted with a borate buffer.

From the viewpoint of preventing adhesion to a surface of the living body (cornea in the case of a lens for eye) of the patient, the surface of the medical device preferably has excellent lubricity. As an indicator representing the lubricity, the below-mentioned surface friction coefficient ratio (Qa and Qb) measured by the method mentioned in Examples of the present description are preferably smaller.

In the above-mentioned friction, the surface friction coefficient ratio (Qa) in a state of being wetted with a borate buffer of the medical device of the present invention is preferably 2 or less, more preferably 1.6 or less, and still more preferably 1 or less, provided that Qa=MIUa/MIUo: where MIUa represents a coefficient of surface friction between the medical device and a smooth quartz glass plate in a state of being wetted with the borate buffer; and MIUo represents a coefficient of surface friction between "ACUVUE® OASYS", which is a commercially available contact lens, and a smooth quartz glass plate in a state of being wetted with the borate buffer.

The smaller the surface friction coefficient ratio Qa becomes, the better since surface friction decreases, leading to a smaller influence exerted on the living body in the case of generating rubbing with the living body (for example, cornea or palpebral conjunctiva in the case of a contact lens). In that sense, the surface friction coefficient ratio Qa is preferably 1 or less, more preferably 0.8 or less, and most preferably 0.6 or less.

The surface friction coefficient ratio (Qb) in a state of being wetted with a saline is preferably 3 or less, more preferably 2 or less, and still more preferably 1.5 or less, provided that Qb=MIUb/MIUo:
where MIUb represents a coefficient of surface friction between the medical device and a smooth quartz glass plate in a state of being wetted with the saline.

It has been found that, in a medical device in which a layer made of an acidic polymer and a basic polymer is formed on at least a part of a surface of a base material, which is one of preferred aspects of the present invention, Qb tends to become larger than Qa and Qb, and Qb sometimes becomes significantly larger. However, the saline is a liquid which resembles a body fluid (for example, lacrimal fluid in the case of a contact lens). From the viewpoint of preventing adhesion of the medical device to a surface of the living body (cornea in the case of a lens for eye), a surface friction coefficient ratio (Qb) in a state of being wetted with a saline is also preferably small.

The smaller the surface friction coefficient ratio Qb becomes, the better since surface friction decreases, leading to a smaller influence exerted on the living body in the case of generating rubbing with the living body (for example, cornea or palpebral conjunctiva in the case of a contact lens). In that sense, the surface friction coefficient ratio Qb is preferably 1.5 or less, more preferably 1.0 or less, and most preferably 0.8 or less.

In the medical device of the present invention, a difference (Qb−Qa) between a surface friction coefficient ratio Qb in a state of being wetted with a saline and a surface friction coefficient ratio Qa in a state of being wetted with a borate buffer is preferably 1.6 or less, more preferably 1.3 or less, and still more preferably 1.0 or less. It is preferred that the difference between a surface friction coefficient ratio Qb and a surface friction coefficient ratio Qa is small since a difference between lubricity when the medical device is applied to the living body and lubricity before application (for example, upon opening) tends to decrease.

Anti-fouling property of the medical device of the present invention can be evaluated by adhesion of mucin, adhesion of lipid (methyl palmitate), and an artificial lacrimal fluid immersion test. The amount of adhesion determined by these evaluations is preferably as small as possible since the medical device is excellent in comfort, and also a risk of the growth of bacteria is reduced. The amount of adhesion of mucin is preferably 5 $\mu g/cm^2$ or less, more preferably 4 $\mu g/cm^2$ or less, and most preferably 3 $\mu g/cm^2$ or less.

From the viewpoint of supply of oxygen from atmospheric air to the living body of the patient using the medical device, the medical device preferably has high oxygen permeability. The oxygen permeability [$\times 10^{-11}$ ($cm^2$/sec) $mLO_2$/(mL·hPa)] is preferably 50 or more, more preferably 100 or more, still more preferably 200 or more, and most preferably 300 or more. The oxygen permeability [$\times 10^{-11}$ ($cm^2$/sec) $mLO_2$/(mL·hPa)] is preferably 2,000 or less, more preferably 1,500 or less, still more preferably 1,000 or less, and most preferably 700 or less. It is not preferred that the oxygen permeability is excessively increased since an adverse influence may be sometimes exerted on other physical properties such as mechanical properties. The oxygen permeability is measured using a specimen in a dry state.

Since the medical device of the present invention has the above-mentioned characteristics, it is possible to maintain mechanical properties and low water content and to significantly reduce or avoid a phenomenon of adhesion to a surface when contacted with a surface outside or inside the body.

It is preferred that the medical device of the present invention is a medical device which includes a base material, a layer made of an acidic polymer and a basic polymer being formed on at least a part of a surface of the base material.

The base material preferably contains 5% by mass or more of silicon atoms in order to have high oxygen permeability, and to obtain strong adhesion with a polymer to be coated on a surface without involving in a covalent bond. The content (% by mass) of silicon atoms is calculated based on the mass of the base material in a dry state (100% by mass). The content of silicon atoms of the base material is preferably 5% by mass or more, more preferably 7% by mass or more, still more preferably 10% by mass or more, and most preferably 12% by mass or more. The content of silicon atoms of the base material is preferably 36% by mass or less, more preferably 30% by mass or less, and still more preferably 26% by mass or less. It is not preferred that the content of silicon atoms is too large since tensile elastic modulus may sometimes increase.

The content of silicon atoms in the base material can be measured by the following method. After weighing sufficiently dried base material in a platinum crucible, sulfuric acid is added then the base material is incinerated by heating using a hot plate and a burner. The obtained ash is melted with sodium carbonate and water is added. After dissolving by heating, nitric acid is added and the volume is fixed by water. Regarding this solution, silicon atoms are measured by ICP emission spectrometry and the content in the base material is determined.

The base material preferably contains, as a main component, a polymer of a component A: a polysiloxane compound which has a plurality of polymerizable functional groups per molecule, and also has a number average molecular weight of 6,000 or more, or a copolymer of the above component A and a compound which has a polymerizable functional group and is different from the component A. As used herein, the main component means a component which is contained in the amount of 50% by mass or more based on the mass of the base material in a dry state (100% by mass). As used herein, the polysiloxane compound is a compound having a Si—O—Si—O—Si bond.

Number average molecular weight of the component A is preferably 6,000 or more. The present inventors have found that it is possible to obtain a medical device, which is flexible and is excellent in comfort, and is also excellent in mechanical properties such as folding resistance, when the number average molecular weight of the component A is within the above range. The number average molecular weight of the polysiloxane compound as the component A is preferably 8,000 or more, more preferably 9,000 or more, and still more preferably 10,000 or more, since it is possible to obtain a medical device, which is more excellent in mechanical properties such as folding resistance. The number average molecular weight of the component A is preferably 100,000 or less, more preferably 70,000 or less, and still more preferably 50,000 or less. When the number average molecular weight of the component A is too small, mechanical properties such as folding resistance may deteriorate. In particular, when the number average molecular weight is less than 6,000, folding resistance deteriorates. It is not preferred that the number average molecular weight of the component A is too large since flexibility and transparency of the medical device may deteriorate.

It is preferred that the medical device (particularly, lens for eye) of the present invention has high transparency. Regarding criteria of transparency, it is preferred that the medical device is transparent with no turbidity when visually observed. Furthermore, when the lens for eye is observed by a lens projector, it is preferred that turbidity is scarcely or not observed, and it is most preferred that no turbidity is observed.

In the medical device (particularly, lens for eye), dispersion degree (value obtained by dividing mass average molecular weight by number average molecular weight) of the component A is preferably 6 or less, more preferably 3 or less, still more preferably 2 or less, and most preferably 1.5 or less. In the lens for eye, when the dispersion degree of the component A is low, it is possible to achieve such benefits that compatibility with other components is improved and thus transparency of the obtained lens for eye is improved; extractable components contained in the obtained lens reduce; and a ratio of shrinkage associated with lens molding decreases. The ratio of shrinkage associated with lens molding can be evaluated by a molding ratio of lens=[diameter of lens]/[diameter of cavity portion of mold]. As the molding ratio of lens approaches 1, it becomes easier to stably produce a high-quality lens. The molding ratio is preferably 0.85 or more, more preferably 0.9 or more, and most preferably 0.91 or more. The molding ratio is preferably 2.0 or less, more preferably 1.5 or less, and most preferably 1.3 or less.

In the present invention, number average molecular weight of the component A is polystyrene-equivalent number average molecular weight to be measured by a gel permeation chromatographic method (GPC method) using chloroform as a solvent. Mass average molecular weight and dispersion degree (value obtained by dividing mass average molecular weight by number average molecular weight) are also measured by a similar method.

In the present description, the mass average molecular weight is sometimes represented by Mw, and the number average molecular weight is sometimes represented by Mn. The molecular weight of 1,000 is sometimes written as 1 kD. For example, the notation "Mw 33 kD" means "mass average molecular weight of 33,000".

The component A is a polysiloxane compound which has plurality of polymerizable functional groups. The number of polymerizable functional groups of the component A may be 2 or more per molecule, and preferably 2 per molecule from the viewpoint of easily obtaining more flexible (low elastic modulus) medical device. The component A may have a polymerizable functional group at any position of a polymerizable functional group. Particularly preferred is a structure having a polymerizable functional group at both ends of the molecular chain.

The polymerizable functional group of the component A is preferably a radical polymerizable functional group, and more preferably a radical polymerizable functional group having a carbon-carbon double bond. Examples of preferable polymerizable functional group include a vinyl group, an allyl group, a (meth)acryloyl group, an α-alkoxymethylacryloyl group, a maleic acid residue, a fumaric acid residue, an itaconic acid residue, a crotonic acid residue, an isocrotonic acid residue, an citraconic acid residue and the like. Among these polymerizable functional groups, a (meth)acryloyl group is most preferable since it has high polymerizability. Two or more polymerizable functional groups may be the same or different.

As used herein, the term "(meth)acryloyl" represents both methacryloyl and acryloyl, and the same shall apply to terms such as (meth)acryl and (meth)acrylate.

The component A preferably has a structure of the following formula (A1).

[Chemical Formula 2]

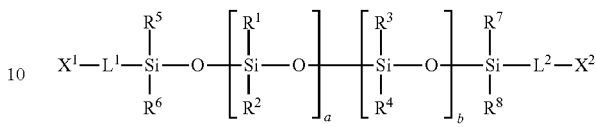

In the formula (A1), $X^1$ and $X^2$ each independently represents a polymerizable functional group. $R^1$ to $R^8$ each independently represents a substituent selected from hydrogen, an alkyl group having 1 to 20 carbon atoms, a phenyl group, and a fluoroalkyl group having 1 to 20 carbon atoms. $L^1$ and $L^2$ each independently represents a divalent group. a and b each independently represents an integer of 0 to 1,500, provided that a and b are not simultaneously 0.

$X^1$ and $X^2$ are preferably radical polymerizable functional groups, and radical polymerizable functional groups having a carbon-carbon double bond are preferable. Examples of preferable polymerizable functional group include a vinyl group, an allyl group, a (meth)acryloyl group, an α-alkoxymethylacryloyl group, a maleic acid residue, a fumaric acid residue, an itaconic acid residue, a crotonic acid residue, an isocrotonic acid residue, a citraconic acid residue and the like. Among these polymerizable functional groups, a (meth)acryloyl group is most preferable since it has high polymerizability.

Suitable specific examples of $R^1$ to $R^8$ include hydrogen; an alkyl group having 1 to 20 carbon atoms, such as a methyl group, an ethyl group, a propyl group, an isopropyl group, a butyl group, a t-butyl group, a decyl group, a dodecyl group, or an octadecyl group; a phenyl group; and a fluoroalkyl group having 1 to 20 carbon atoms, such as a trifluoromethyl group, a trifluoroethyl group, a trifluoropropyl group, a tetrafluoropropyl group, a hexafluoroisopropyl group, a pentafluorobutyl group, a heptafluoropentyl group, a nonafluorohexyl group, a hexafluorobutyl group, a heptafluorobutyl group, an octafluoropentyl group, a nonafluoropentyl group, a dodecafluoroheptyl group, a tridecafluoroheptyl group, a dodecafluorooctyl group, a tridecafluorooctyl group, a hexadecafluorodecyl group, a heptadecafluorodecyl group, a tetrafluoropropyl group, a pentafluoropropyl group, a tetradecafluorooctyl group, a pentadecafluorooctyl group, an octadecafluorodecyl group, or a nonadecafluorodecyl group. Among these groups, hydrogen and a methyl group are more preferable from the viewpoint of imparting satisfactory mechanical properties and high oxygen permeability to the medical device, and a methyl group is most preferable.

$L^1$ and $L^2$ are preferably divalent groups having 1 to 20 carbon atoms. Among these groups, groups represented by the following formulas (LE1) to (LE12) are preferable since a compound of the formula (A1) has an advantage of easily obtaining with high purity. Among these, $L^1$ and $L^2$ are more preferably groups represented by the following formulas (LE1), (LE3), (LE9) and (LE11), still more preferably groups represented by the following formulas (LE1) and (LE3), and most preferably a group represented by the following formula (LE1). In the following formulas (LE1) to (LE12), left side is drawn as an end which is bonded to a polymerizable functional group $X^1$ or $X^2$, while right side is drawn as an end which is bonded to a silicon atom.

[Chemical Formula 3]

| | |
|---|---|
| OCH$_2$CH$_2$CH$_2$ | (LE1) |
| NHCH$_2$CH$_2$CH$_2$ | (LE2) |
| OCH$_2$CH$_2$NHCOOCH$_2$CH$_2$CH$_2$ | (LE3) |
| OCH$_2$CH$_2$NHCONHCH$_2$CH$_2$CH$_2$ | (LE4) |
| OCH$_2$CH$_2$CH$_2$CH$_2$ | (LE5) |
| NHCH$_2$CH$_2$CH$_2$CH$_2$ | (LE6) |
| OCH$_2$CH$_2$NHCOOCH$_2$CH$_2$CH$_2$CH$_2$ | (LE7) |
| OCH$_2$CH$_2$NHCONHCH$_2$CH$_2$CH$_2$CH$_2$ | (LE8) |
| OCH$_2$CH$_2$OCH$_2$CH$_2$CH$_2$ | (LE9) |
| NHCH$_2$CH$_2$OCH$_2$CH$_2$CH$_2$ | (LE10) |
| OCH$_2$CH$_2$NHCOOCH$_2$CH$_2$OCH$_2$CH$_2$CH$_2$ | (LE11) |
| OCH$_2$CH$_2$NHCONHCH$_2$CH$_2$OCH$_2$CH$_2$CH$_2$ | (LE12) |

In the formula (A1), a and b each independently represents an integer of 0 to 1,500, provided that a and b are not simultaneously 0. Preferably, a and b each independently within a range from 0 to 1,500. The total value of a and b (a+b) is preferably 80 or more, more preferably 100 or more, still more preferably from 100 to 1,400, even more preferably from 120 to 950, and yet more preferably from 130 to 700.

When all of $R^1$ to $R^8$ are methyl groups, b=0, and a is preferably from 80 to 1,500, more preferably from 100 to 1,400, still more preferably from 120 to 950, and even more preferably from 130 to 700. In this case, the value of a is determined by the molecular weight of the polysiloxane compound as the component A.

The component A of the present invention may be used alone, or two or more kinds may be used in combination.

The other compound to be copolymerized with the component A is preferably a component B which is a polymerizable monomer having a fluoroalkyl group. The component B has properties of water and oil repellency due to a decrease in critical surface tension caused by a fluoroalkyl group, thereby exerting the effect of suppressing a surface of a mechanical device from being contaminated with components such as protein and lipid in a body fluid (lacrimal fluid in the case of a lens for eye). The component B also has the effect of giving a medical device, which is flexible and is excellent in comfort, and is also excellent in mechanical properties such as folding resistance. Suitable specific examples of the fluoroalkyl group of the component B include fluoroalkyl groups having 1 to 20 carbon atoms, such as a trifluoromethyl group, a trifluoroethyl group, a trifluoropropyl group, a tetrafluoropropyl group, a hexafluoroisopropyl group, a pentafluorobutyl group, a heptafluoropentyl group, a nonafluorohexyl group, a hexafluorobutyl group, a heptafluorobutyl group, an octafluoropentyl group, a nonafluoropentyl group, a dodecafluoroheptyl group, a tridecafluoroheptyl group, a dodecafluorooctyl group, a tridecafluorooctyl group, a hexadecafluorodecyl group, a heptadecafluorodecyl group, a tetrafluoropropyl group, a pentafluoropropyl group, a tetradecafluorooctyl group, a pentadecafluorooctyl group, an octadecafluorodecyl group, and a nonadecafluorodecyl group. The fluoroalkyl group is more preferably a fluoroalkyl group having 2 to 8 carbon atoms, for example, a trifluoroethyl group, a tetrafluoropropyl group, a hexafluoroisopropyl group, an octafluoropentyl group or a dodecafluorooctyl group, and most preferably a trifluoroethyl group.

The polymerizable functional group of the component B is preferably a radical polymerizable functional group, and more preferably a radical polymerizable functional group having a carbon-carbon double bond. Examples of preferable polymerizable functional group include a vinyl group, an allyl group, a (meth)acryloyl group, an α-alkoxymethylacryloyl group, a maleic acid residue, a fumaric acid residue, an itaconic acid residue, a crotonic acid residue, an isocrotonic acid residue, a citraconic acid residue and the like. Among these polymerizable functional groups, a (meth)acryloyl group is most preferable since it has high polymerizability.

The component B also has the effect of giving a medical device, which is flexible and is excellent in comfort, and is also excellent in mechanical properties such as folding resistance. The component B is most preferably a (meth)acrylic acid fluoroalkyl ester. Specific examples of the (meth)acrylic acid fluoroalkyl ester include trifluoroethyl(meth)acrylate, tetrafluoroethyl(meth)acrylate, trifluoropropyl(meth)acrylate, tetrafluoropropyl(meth)acrylate, pentafluoropropyl(meth)acrylate, hexafluorobutyl(meth)acrylate, hexafluoroisopropyl(meth)acrylate, heptafluorobutyl(meth)acrylate, octafluoropentyl(meth)acrylate, nonafluoropentyl(meth)acrylate, dodecafluoropentyl(meth)acrylate, dodecafluoroheptyl(meth)acrylate, dodecafluorooctyl(meth)acrylate, and tridecafluoroheptyl(meth)acrylate. Trifluoroethyl(meth)acrylate, tetrafluoroethyl(meth)acrylate, hexafluoroisopropyl(meth)acrylate, octafluoropentyl(meth)acrylate, and dodecafluorooctyl(meth)acrylate are preferably used. Trifluoroethyl(meth)acrylate is most preferable.

The component B of the present invention may be used alone, or two or more kinds may be used in combination.

The content of the component B in the copolymer is preferably from 10 to 500 parts by mass, more preferably from 20 to 400 parts by mass, and still more preferably from 20 to 200 parts by mass, based on 100 parts by mass of the component A. When the use amount of the component B is too small, white turbidity may arise in the base material, or mechanical properties such as folding resistance may become insufficient.

It is possible to use, as the copolymer to be used in the base material, a copolymer obtained by copolymerizing a component which is different from the components A and B (hereinafter referred to as a component C), in addition to the components A and B.

The component C may be a component which decreases a glass transition point of a copolymer to room temperature or 0° C. or lower. The component decreases cohesive energy and therefore exerts the effect of imparting rubber elasticity and flexibility to the copolymer.

The polymerizable functional group as the component C is preferably a radical polymerizable functional group, and more preferably a radical polymerizable functional group having a carbon-carbon double bond. Examples of preferable polymerizable functional group include a vinyl group, an allyl group, a (meth)acryloyl group, an α-alkoxymethylacryloyl group, a maleic acid residue, a fumaric acid residue, an itaconic acid residue, a crotonic acid residue, an isocrotonic acid residue, a citraconic acid residue and the like. Among these polymerizable functional groups, a (meth)acryloyl group is most preferable since it has high polymerizability.

The component C, which is suitable for the improvement of mechanical properties such as flexibility and folding resistance, is a (meth)acrylic acid alkyl ester, and preferably a (meth)acrylic acid alkyl ester whose alkyl group has 1 to 20 carbon atoms, and specific examples thereof include methyl (meth)acrylate, ethyl (meth)acrylate, n-propyl(meth)acrylate, n-butyl (meth)acrylate, tert-butyl (meth)acrylate, isobutyl (meth)acrylate, n-hexyl(meth)acrylate, n-octyl (meth)acrylate, 2-ethylhexyl(meth)acrylate, n-heptyl(meth)acrylate, n-nonyl(meth)acrylate, n-decyl(meth)acrylate, iso-decyl(meth)acrylate, n-lauryl(meth)acrylate, tridecyl(meth)acrylate, n-dodecyl(meth)acrylate, cyclopentyl(meth)acrylate, cyclohexyl(meth)acrylate, n-stearyl(meth)acrylate and the like. The (meth)acrylic acid alkyl ester is more preferably n-butyl (meth)acrylate, n-octyl(meth)acrylate, n-lauryl(meth)acrylate, or n-stearyl(meth)acrylate. Among these, a (meth)acrylic acid alkyl ester whose alkyl group has 1 to 10 carbon atoms is more preferable. It is not preferred that the number of carbon atoms of the alkyl group is too large since transparency of the obtained medical device may sometimes deteriorate.

Furthermore, in order to improve mechanical properties, surface wettability, dimensional stability of the medical device and the like, the below-mentioned monomer can be optionally copolymerized.

Examples of the monomer for the improvement of mechanical properties include an aromatic vinyl compound such as styrene, tert-butylstyrene, and α-methylstyrene.

Examples of the monomer for the improvement of surface wettability include methacrylic acid, acrylic acid, itaconic acid, 2-hydroxyethyl methacrylate, 2-hydroxyethyl acrylate, 2-hydroxypropylmethacrylate, 2-hydroxypropyl acrylate, glycerol methacrylate, polyethylene glycol methacrylate, N,N-dimethylacrylamide, N-methylacrylamide, dimethylaminoethyl methacrylate, methylenebisacrylamide, diacetoneacrylamide, N-vinylpyrrolidone, N-vinylcaprolactam, N-vinylacetamide, N-vinyl-N-methylacetamide and the like. Among these monomers, a monomer having an amide group, such as N,N-dimethylacrylamide, N-methylacrylamide, dimethylaminoethyl methacrylate, methylenebisacrylamide, diacetoneacrylamide, N-vinylpyrrolidone, N-vinylcaprolactam, N-vinylacetamide, or N-vinyl-N-methylacetamide is preferable.

Examples of the monomer for the improvement of dimensional stability of the medical device include ethylene glycol dimethacrylate, diethylene glycol dimethacrylate, triethylene glycol dimethacrylate, polyethylene glycol dimethacrylate, trimethylolpropane trimethacrylate, pentaerythritol tetramethacrylate, bisphenol A dimethacrylate, vinyl methacrylate, acryl methacrylate, and acrylates corresponding to these methacrylates, divinylbenzene, triallyl isocyanurate and the like.

The component C may be used alone, or two or more kinds may be used in combination.

The use amount of the component C is preferably from 0.001 to 400 parts by mass, more preferably from 0.01 to 300 parts by mass, still more preferably from 0.01 to 200 parts by mass, and most preferably from 0.01 to 30 parts by mass, based on 100 parts by mass of the component A. When the use amount of the component C is too small, it may become difficult to obtain the effect which is expected to the component C. When the use amount of the component C is too large, white turbidity may arise in the obtained medical device, or mechanical properties such as folding resistance may become insufficient.

It is also possible to use, as the copolymer used in the base material, a copolymer obtained by copolymerizing with a component M, in addition to the component A. The component M is a "monofunctional monomer having one polymerizable functional group and one siloxanyl group per molecule". As used herein, the siloxanyl group means a group having a Si—O—Si bond.

The siloxanyl group of the component M is preferably linear. When the siloxanyl group is linear, shape recovery properties of the obtained medical device are improved. As used herein, linear structure refers to a structure indicated by one linear discrete Si—(O—Si)$_{n-1}$—O—Si bond (provided that n represents an integer of 2 or more) with silicon atoms bonded to a group having a polymerizable group as a starting point. In order that the obtained medical device obtains sufficient shape recovery properties, n is preferably an integer of 3 or more, more preferably 4 or more, still more preferably 5 or more, and most preferably 6 or more. The phrase "the siloxanyl group is linear" means that the siloxanyl group has the linear structure, and is also free from a Si—O—Si bond which does not satisfy the conditions of the linear structure.

The umber average molecular weight of the component M is preferably from 300 to 120,000. When the number average molecular weight of the component M is within the above range, it is possible to obtain a base material, which is flexible (low elastic modulus) and is excellent in comfort, and is also excellent in mechanical properties such as folding resistance. Number average molecular weight of the component M is more preferably 500 or more since it is possible to obtain a base material which is excellent in mechanical properties such as folding resistance and is also excellent in shape recovery properties. The number average molecular weight of the component M is more preferably within a range from 1,000 to 25,000, and still more preferably from 5,000 to 15,000. When the number average molecular weight of the component M is too small, mechanical properties such as folding resistance may deteriorate. In particular, when the number average molecular weight is less than 500, folding resistance and shape recovery properties may deteriorate. It is not preferred that the number average molecular weight of the component M is too large since flexibility and transparency may deteriorate.

The polymerizable functional group of the component M is preferably a radical polymerizable functional group, and more preferably a radical polymerizable functional group having a carbon-carbon double bond. Examples of preferable polymerizable functional group include a vinyl group, an allyl group, a (meth)acryloyl group, an α-alkoxymethylacryloyl group, a maleic acid residue, a fumaric acid residue, an itaconic acid residue, a crotonic acid residue, an isocrotonic acid residue, a citraconic acid residue and the like. Among these polymerizable functional groups, a (meth)acryloyl group is most preferable since it has high polymerizability.

The component M preferably has a structure of the following formula (ML1).

[Chemical Formula 4]

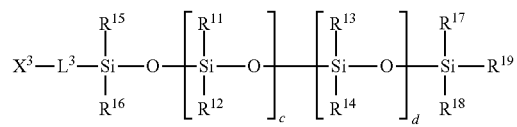

(ML1)

In the formula, $X^3$ represents a polymerizable functional group. $R^{11}$ to $R^{19}$ each independently represents a substituent selected from hydrogen, an alkyl group having 1 to 20 carbon atoms, a phenyl group, and a fluoroalkyl group having 1 to 20 carbon atoms. $L^3$ represents a divalent group. c and d each independently represents an integer of 0 to 700, provided that c and d are not simultaneously 0.

$X^3$ is preferably a radical polymerizable functional group, and more preferably a radical polymerizable functional group having a carbon-carbon double bond. Examples of preferable polymerizable functional group include a vinyl group, an allyl group, a (meth)acryloyl group, an α-alkoxymethylacryloyl group, a maleic acid residue, a fumaric acid residue, an itaconic acid residue, a crotonic acid residue, an isocrotonic acid residue, a citraconic acid residue and the like. Among these polymerizable functional groups, a (meth)acryloyl group is most preferable since it has high polymerizability.

The polymerizable functional group of the component M is more preferably copolymerizable with the polymerizable functional group of the component A since a medical device having satisfactory mechanical properties is easily obtained. When the component Di is uniformly copolymerized with the component A, a medical device having satisfactory surface properties is easily obtained. The polymerizable functional group of the component M is still more preferably identical with the polymerizable functional group of the component A.

Suitable specific examples of $R^{11}$ to $R^{19}$ include hydrogen; an alkyl group having 1 to 20 carbon atoms, such as a methyl group, an ethyl group, a propyl group, an isopropyl group, a butyl group, a t-butyl group, a decyl group, a dodecyl group, or an octadecyl group; a phenyl group; and a fluoroalkyl group having 1 to 20 carbon atoms, such as a trifluoromethyl group, a trifluoroethyl group, a trifluoropropyl group, a tetrafluoropropyl group, a hexafluoroisopropyl group, a pentafluorobutyl group, a heptafluoropentyl group, a nonafluorohexyl group, a hexafluorobutyl group, a heptafluorobutyl group, an octafluoropentyl group, a nonafluoropentyl group, a dodecafluoroheptyl group, a tridecafluoroheptyl group, a dodecafluorooctyl group, a tridecafluorooctyl group, a hexadecafluorodecyl group, a heptadecafluorodecyl group, a tetrafluoropropyl group, a pentafluoropropyl group, a tetradecafluorooctyl group, a pentadecafluorooctyl group, an octadecafluorodecyl group, or a nonadecafluorodecyl group. Among these groups, hydrogen and a methyl group are still more preferable from the viewpoint of imparting satisfactory mechanical properties and high oxygen permeability to the medical device, and a methyl group is most preferable.

$L^3$ is preferably a divalent group having 1 to 20 carbon atoms. Among these groups, groups represented by the following formulas (LE1) to (LE12) are preferable since a compound of the formula (ML1) has an advantage of easily obtaining with high purity. Among these, $L^3$ are more preferably groups represented by the following formulas (LE1), (LE3), (LE9) and (LE11), still more preferably groups represented by the following formulas (LE1) and (LE3), and most preferably a group represented by the following formula (LE1). In the following formulas (LE1) to (LE12), left side is drawn as an end which is bonded to a polymerizable functional group $X^3$, while right side is drawn as an end which is bonded to a silicon atom.

[Chemical Formula 5]

$OCH_2CH_2CH_2$ (LE1)

$NHCH_2CH_2CH_2$ (LE2)

$OCH_2CH_2NHCOOCH_2CH_2CH_2$ (LE3)

$OCH_2CH_2NHCONHCH_2CH_2CH_2$ (LE4)

$OCH_2CH_2CH_2CH_2$ (LE5)

$NHCH_2CH_2CH_2CH_2$ (LE6)

$OCH_2CH_2NHCOOCH_2CH_2CH_2CH_2$ (LE7)

$OCH_2CH_2NHCONHCH_2CH_2CH_2CH_2$ (LE8)

$OCH_2CH_2OCH_2CH_2CH_2$ (LE9)

$NHCH_2CH_2OCH_2CH_2CH_2$ (LE10)

$OCH_2CH_2NHCOOCH_2CH_2OCH_2CH_2CH_2$ (LE11)

$OCH_2CH_2NHCONHCH_2CH_2OCH_2CH_2CH_2$ (LE1

In the formula (ML1), c and d each independently represents an integer of 0 to 700, provided that c and d are not simultaneously 0. The total value of c and d (c+d) is preferably 3 or more, more preferably 10 or more, still more preferably from 10 to 500, even more preferably from 30 to 300, and yet more preferably from 50 to 200.

When all of $R^{11}$ to $R^{18}$ are methyl groups, d=0, and c is preferably from 3 to 700, more preferably from 10 to 500, still more preferably from 30 to 300, and even more preferably from 50 to 200. In this case, the value of c is determined by the molecular weight of the component M.

In the base material of the medical device of the present invention, the component M of the present invention may be used alone, or two or more kinds may be used in combination.

When the base material of the medical device of the present invention contains an appropriate amount of the component M, crosslinking density may decrease leading to an increase in the degree of freedom of a polymer, thus enabling realization of a base material having moderately flexible low elastic modulus. In contrast, when the content of the component M is too small, crosslinking density may increase leading to a hard base material. It is not preferred that since the content of the component M is too large, the base material may become too soft and thus it is likely to be broken.

In the base material of the medical device of the present invention, regarding a mass ratio of the component M and the component A, the content of the component M is preferably from 5 to 200 parts by mass, more preferably from 7 to 150 parts by mass, and most preferably from 10 to 100 parts by mass, based on 100 parts by mass of the component A. When the content of the component M is less than 5 parts by mass based on 100 parts by mass of the component A, crosslinking density may increase lading to a hard base material. When the content of the component M is more than 200 parts by mass based on 100 parts by mass of the component A, the base material may become too soft and thus it is likely to be broken, and thus both cases are not preferred.

The medical device of the present invention may further contain a component such as an ultraviolet absorber, a pigment, a colorant, a humectant, a slip agent, a pharmaceutical and a nutritional supplementary component, a compatibilizing component, an antibacterial component, a mold release agent and the like. Any of the above-mentioned components can be contained in a non-reactive form or a copolymerization form.

In the case of containing an ultraviolet absorber, it is possible to protect body tissue (eye in the case of a lens for eye) of patients using a medical device from harmful ultraviolet rays. In the case of containing a colorant, the medical device is colored, results in easy identification and an improvement in convenience during handling.

Any of the above-mentioned components can be contained in a non-reactive form or a copolymerization form. It is preferred that the above components are copolymerized, that is, an ultraviolet absorber having a polymerizable group or a colorant having a polymerizable group is used since the component is copolymerized with a base material and immobilized, and thus elution may scarcely occur.

The base material is preferably composed of components to be selected from an ultraviolet absorber and a colorant, and two or more kinds of components C other than these components (hereinafter referred to as a component Ck). In that case, it is preferred that at least one of the component Ck is selected from a (meth)acrylic acid alkyl ester having 1 to 10 carbon atoms, and at least one of the component Ck is selected from a monomer for the improvement of surface wettability. Use of two or more kinds of components Ck enhances affinity with an ultraviolet absorber or a colorant, and thus it becomes possible to obtain a transparent base material.

In the case of using an ultraviolet absorber, the use amount thereof is preferably from 0.01 to 20 parts by mass, more preferably from 0.05 to 10 parts by mass, and still more preferably from 0.1 to 2 parts by mass, based on 100 parts by mass of the component A. In the case of using a colorant, the use amount thereof is preferably from 0.00001 to 5 parts by mass, more preferably from 0.0001 to 1 part by mass, and still more preferably from 0.0001 to 0.5 part by mass, based on 100 parts by mass of the component A. When the content of the ultraviolet absorber or colorant is too small, it may become difficult to obtain the ultraviolet absorption effect or coloration effect. In contrast, when the content is too large, it may become difficult to dissolve these components in the base material. The use amount of the component Ck is preferably from 0.1 to 100 parts by mass, more preferably from 1 to 80 parts by mass, and still more preferably from 2 to 50 parts by mass, based on 100 parts by mass of the component A. When the use amount of the component Ck is too small, it may become difficult to obtain a transparent base material because of lack of affinity with the ultraviolet absorber or colorant. It is not preferred that the use amount of the component Ck is too large since white turbidity may arise in the obtained medical device, or mechanical properties such as folding resistance may become insufficient.

Crosslinking degree of the base material of the medical device of the present invention is preferably within a range from 2.0 to 18.3. The crosslinking degree is represented by the following equation (Q1).

[Equation 1]

$$\text{Crosslinking degree} = \frac{\sum_{n=1}^{\infty} \{Qn \times (n-1)\}}{\sum_{n=1}^{\infty} Wn} \quad (Q1)$$

In the formula (Q1), Qn represents a total millimolar amount of a monomer having n polymerizable groups per molecule, and Wn represents a total mass (kg) of a monomer having n polymerizable groups per molecule. When molecular weight of the monomer has distribution, the millimolar amount is calculated using number average molecular weight.

It is not preferred that the crosslinking degree of the base material of the present invention is less than 2.0 since it may become difficult to handle because of being too soft. It is not preferred that the crosslinking degree of the base material is more than 18.3 since comfort may become worse because of being too hard. The crosslinking degree is more preferably within a range from 3.5 to 16.0, still more preferably from 8.0 to 15.0, and most preferably from 9.0 to 14.0.

It is possible to use, as a method for producing a base material of a medical device, a known method. For example, it is possible to use a method in which a round bar- or plate-shaped polymer is once obtained and then processed into a desired shape by cutting or the like, a mold polymerization method, a spin-cast polymerization method and the like. In the case of obtaining a medical device by cutting, freeze-cutting at low temperature is suitable.

A method of polymerizing a raw material composition containing a component A by a mold polymerization method to produce a lens for eye will be described below as an example. First, a gap between two mold members each having a fixed shape is filled with a raw material composition. Examples of the material of the mold member include resin, glass, ceramics, metal and the like. In the case of performing photopolymerization, since an optically transparent material is preferable, the resin or glass is preferably used. Depending on the shape of the mold member or properties of the raw material composition, a gasket may be used so as to impart a fixed thickness to the lens for eye, and to prevent liquid leakage of the raw material composition filled in the gap. The mold with the gap filled with raw material composition is subsequently irradiated with active rays such as ultraviolet rays, visible rays or a combination thereof, or heating in an oven or a liquid bath, thereby polymerizing the raw material composition filled in the mold. It is also possible to employ a method using two types of polymerization methods. That is, it is also possible to perform heat polymerization after photopolymerization, or perform photopolymerization after heat polymerization. In a specific aspect of photopolymerization, for example, light including ultraviolet rays such as light of a mercury lamp or an ultraviolet lamp (for example, FL15BL, Toshiba Corporation) are irradiated within a short time (usually 1 hour or less). In the case of performing heat polymerization, conditions of gradually raising a temperature of the composition from about room temperature and raising to the temperature of 60° C. to 200° C. over several hours to several tens of hours are preferably used so as to maintain optical uniformity and grade of a lens for eye, and to enhance reproducibility.

In the polymerization, a heat polymerization initiator typified by a peroxide or an azo compound, or a photopolymerization initiator is preferably added so as to facilitate the polymerization. In the case of performing heat polymerization, an initiator having optimum decomposition characteristics at a desired reaction temperature is selected. Commonly, an azo-based initiator and a peroxide-based initiator, each having a ten-hour half-life temperature of 40 to 120° C., are suitable. Examples of the photoinitiator in the case of performing photopolymerization include a carbonyl compound, a peroxide, an azo compound, a sulfur compound, a halogen compound, a metal salt and the like. These polymerization initiators are used alone or in combination. The amount of the polymerization initiator is preferably up to 5% by mass based on a polymerization mixture.

In the case of performing polymerization, a polymerization solvent can be used. Organic and inorganic various solvents can be applied as the solvent. Examples of the solvent include water; alcohol-based solvents such as methyl alcohol, ethyl alcohol, normal propyl alcohol, isopropyl alcohol, normal butyl alcohol, isobutyl alcohol, t-butyl alcohol, t-amyl alcohol, tetrahydrolinalool, ethylene glycol, diethylene glycol, triethylene glycol, tetraethylene glycol, and polyethylene glycol; glycol ether-based solvents such as methyl cellosolve, ethyl cellosolve, isopropyl cellosolve, butyl cellosolve, propylene glycol monomethyl ether, diethylene glycol monomethyl ether, triethylene glycol monomethyl ether, polyethylene glycol monomethyl ether, ethylene glycol dimethyl ether, diethylene glycol dimethyl ether, triethylene glycol dimethyl ether, and polyethylene glycol dimethyl ether; ester-based solvents such as ethyl acetate, butyl acetate, amyl acetate, ethyl lactate, and methyl benzoate; aliphatic hydrocarbon-based solvents such as normal hexane, normal heptane, and normal octane; alicyclic hydrocarbon-based solvents such as cyclohexane and ethylcyclohexane; ketone-based solvents such as acetone, methyl ethyl ketone, and methyl isobutyl ketone; aromatic hydrocarbon-based solvents such as benzene, toluene, and xylene; and petroleum-based solvents. These solvent may be used alone, or two or more kinds may be used in combination.

It is preferred that a layer made of an acidic polymer and a basic polymer (hereinafter referred to as a coating layer) is formed on at least a part of a surface of a base material in the medical device of the present invention. Inclusion of a coating layer imparts satisfactory wettability and lubricity to the surface of the lens, and thus imparting excellent comfort.

The present inventors have found that, even if the medical device of the present invention has low water content and is soft, and also the base material is neutral, it is possible to impart sufficient wettability, lubricity and anti-fouling property to the surface of the medical device by forming a coating layer made of an acidic polymer and a basic polymer on the surface. Thereby, according to the medical device of the present invention, it is possible to significantly reduce or avoid a phenomenon of adhesion to the cornea during wear (a phenomenon of adhesion to a surface when contacted with a surface outside or inside the body), which has hitherto been regarded as a problem in a conventional medical device.

It is not necessary to have a covalent bond between the coating layer and the base material. It is preferred to have no covalent bond between the coating layer and the base material since it become possible to produce by a simple and easy step. The coating layer has practical durability even in the case of having no covalent bond between the coating layer and the base material.

The coating layer is formed by treating a surface of a base material with an acidic polymer solution ("solution" means an aqueous solution) and a basic polymer solution ("solution" means an aqueous solution) which will be described in detail below. The aqueous solution means a solution containing water as a main component.

The coating layer is preferably made of one or more kinds of acidic polymers and one or more kinds of basic polymers. Use of two or more kinds of acidic polymers or two or more kinds of basic polymers are more preferable since it is easy to develop properties such as lubricity and anti-fouling property to the surface of the medical device. In particular, use of two or more kinds of acidic polymers and one or more kinds of basic polymers are more preferable since this tendency is to be further increased.

One kind of a polymer means a polymer group produced by one synthesis reaction. Even if the kind of the composing monomer is the same, a polymer synthesized by varying a mixing ratio is not one kind.

The coating layer is preferably formed by performing a treatment with one or more kinds of acidic polymer solutions one or more times, and a treatment with one or more kinds of basic polymer solutions one or more times.

The coating layer is preferably formed on a surface of the base material by the treatment with one or more kinds of acidic polymer solutions and the treatment with one or more kinds of basic polymer solutions 1 to 5 times, more preferably 1 to 3 times, and still more preferably 1 to 2 times, respectively. The number of times of the treatment with an acidic polymer solution may be different from the number of times of the treatment with a basic polymer solution.

The present inventors have found that excellent wettability and lubricity can be imparted by very small number of times of the treatment with one or more kinds of acidic polymer solutions and the treatment with one or more kinds of basic polymer solutions (2 or 3 in total) in the medical device of the present invention. This fact is crucially important for industry from the viewpoint of shortening of the production process. In that sense, in the medical device of the present invention, the total number of the treatments with acidic polymer solutions and basic polymer solutions for forming a coating layer is preferably 2 or 3.

The coating layer is preferably formed by performing a treatment with one or more kinds of an acidic polymer solution once, a treatment with two kinds of acidic polymer solution twice (each once), and a treatment with a basic polymer solution once.

The present inventors have also confirmed that wettability and lubricity are scarcely developed only by containing either an acidic polymer solution or a basic polymer solution in the coating layer.

It is possible to suitably use, as the basic polymer, a homopolymer or copolymer having a plurality of groups having basicity along a polymer chain. An amino group and salts thereof are suitable as the group having basicity. Suitable examples of the basic polymer include an amino group-containing (meth)acrylate polymer such as poly(allylamine), poly(vinylamine), poly(ethyleneimine), poly(vinylbenzyltrimethylamine), polyaniline, poly(aminostyrene) or poly(N,N-dialkylaminoethyl methacrylate); an amino group-containing (meth)acrylamide polymer such as poly (N, N-dimethylaminopropylacrylamide); and salts thereof. Although the followings are examples of a homopolymer, these copolymers (i.e., a copolymer of basic monomers composing the basic polymer, or a copolymer of a basic monomer and the other monomer) can also be suitably used.

When the basic polymer is a copolymer, the basic monomer composing the copolymer is preferably a monomer having an allyl group, a vinyl group, and a (meth)acryloyl group from the viewpoint of high polymerizability, and most preferably a monomer having a (meth)acryloyl group. Suitable examples of the basic monomer composing the copolymer include allylamine, vinylamine (N-vinylcarboxylic acid amide as a precursor), vinylbenzyltrimethylamine, amino group-containing styrene, amino group-containing (meth)acrylate, amino group-containing (meth)acrylamide, and salts thereof. Among these monomers, amino group-containing (meth)acrylate, amino group-containing (meth)acrylamide, and salts thereof are more preferably from the viewpoint of high polymerizability, and N,N-dimethylaminoethyl methacrylate, N,N-dimethylaminopropyl acrylamide, and salts thereof are most preferable.

The basic polymer may be a polymer having a quaternary ammonium structure. The polymer having a quaternary ammonium structure compound can impart antimicrobial properties to a medical device when used for coating of the medical device.

It is possible to suitably use, as the acidic polymer, a homopolymer or copolymer having a plurality of groups having acidity along a polymer chain. The group having acidity is suitably a carboxyl group, a sulfonic acid group and salts thereof, and most suitably a carboxyl group, and salts thereof. Examples of suitable acidic polymer include polymethacrylic acid, polyacrylic acid, poly(vinylbenzoic acid), poly(thiophene-3-acetic acid), poly(4-styrenesulfonic acid), polyvinylsulfonic acid, poly(2-acrylamide-2-methylpropanesulfonic acid), and salts thereof. Although the above polymers are examples of a homopolymer, these copolymers (i.e., a copolymer of basic monomers composing the basic polymer, or a copolymer of a basic monomer and the other monomer) can also be suitably used.

When the acidic polymer is a copolymer, the acidic monomer composing the copolymer is preferably a monomer having an allyl group, a vinyl group, and a (meth)acryloyl group from the viewpoint of high polymerizability, and most preferably a monomer having a (meth)acryloyl group. Suitable examples of the acidic monomer composing the copolymer include (meth)acrylic acid, vinylbenzoic acid, styrenesulfonic acid, vinylsulfonic acid, 2-acrylamide-2-methylpropanesulfonic acid, and salts thereof. Among these monomers, (meth)acrylic acid, 2-acrylamide-2-methylpropanesulfonic acid, and salts thereof are more preferable, and (meth)acrylic acid, and salts thereof are most preferable.

It is preferred that at least one kind of basic and acidic polymers is a polymer having a group selected from an amide bond and a hydroxyl group. It is preferred that a basic polymer and/or an acidic polymer has/have an amide bond since a surface having not only wettability but also lubricity can be formed. It is preferred that a basic polymer and/or an acidic polymer has/have a hydroxyl group since a surface having not only excellent wettability but also excellent anti-fouling property against a lacrimal fluid can be formed.

More preferably, two or more kinds of the acidic polymer and basic polymer are polymers having a group selected from a hydroxyl group and an amide bond. That is, the medical device preferably contains two or more kinds selected from an acidic polymer having a hydroxyl group, a basic polymer having a hydroxyl group, an acidic polymer having an amide bond, and a basic polymer having an amide bond. In this case, it is preferred since the effect of forming a surface having lubricity, or the effect capable of forming a surface having excellent anti-fouling property against a lacrimal fluid can be more significantly exerted.

More preferably, the coating layer contains at least one kind selected from an acidic polymer having a hydroxyl group and a basic polymer having a hydroxyl group, and at least one kind selected from an acidic polymer having an amide bond, and a basic polymer having an amide bond. In this case, it is preferred since both the effect of forming a surface having lubricity, and the effect capable of forming a surface having excellent anti-fouling property against a lacrimal fluid can be exerted.

Examples of the basic polymer having an amide bond include polyamides having an amino group, partially hydrolyzed chitosan, a copolymer of a basic monomer and a monomer having an amide bond and the like.

Examples of the acidic polymer having an amide bond include polyamides having a carboxyl group, a copolymer of an acidic monomer and a monomer having an amide bond and the like.

Examples of the basic polymer having a hydroxyl group include amino-polysaccharides such as chitin, a copolymer of a basic monomer and a monomer having a hydroxyl group and the like.

Examples of the acidic polymer having a hydroxyl group include polysaccharides having an acidic group, such as hyaluronic acid, chondroitin sulfate, carboxymethyl cellulose, and carboxypropyl cellulose; a copolymer of an acidic monomer and a monomer having an amide bond and the like.

The monomer having an amide bond is preferably a monomer having a (meth)acrylamide group and N-vinylcarboxylic acid amide (including a cyclic monomer) from the viewpoint of ease of polymerization. Suitable examples of the monomer include vinylpyrrolidone, N-vinylcaprolactam, N-vinylacetamide, N-methyl-N-vinylacetamide, N-vinylformamide, N,N-dimethylacrylamide, N,N-diethylacrylamide, N-isopropylacrylamide, N-(2-hydroxyethyl) acrylamide, acryloylmorpholine, and acrylamide. Among these monomers, N-vinylpyrrolidone and N,N-dimethylacrylamide are preferable from the viewpoint of lubricity, and N,N-dimethylacrylamide is most preferable.

Suitable examples of the monomer having a hydroxyl group include hydroxyethyl (meth)acrylate, hydroxypropyl (meth)acrylate, hydroxybutyl (meth)acrylate, hydroxyethyl (meth)acrylamide, glycerol(meth)acrylate, caprolactone-modified 2-hydroxyethyl (meth)acrylate, N-(4-hydroxyphenyl)maleimide, hydroxystyrene, and vinyl alcohol (carboxylic acid vinyl ester as a precursor). The monomer having a hydroxyl group is preferably a monomer having a (meth) acryloyl group from the viewpoint of ease of polymerization, and more preferably a (meth)acrylic acid ester monomer. Among these monomers, hydroxyethyl (meth)acrylate, hydroxypropyl(meth)acrylate and glycerol(meth)acrylate are preferable from the viewpoint of anti-fouling property against a lacrimal fluid, and hydroxyethyl (meth)acrylate is most preferable.

Specific examples of preferable copolymer of a basic monomer and a monomer having an amide bond include an N,N-dimethylaminoethyl methacrylate/N-vinylpyrrolidone copolymer, an N,N-dimethylaminoethyl methacrylate/N,N-dimethylacrylamide copolymer, an N,N-dimethylaminopropyl acrylamide/N-vinylpyrrolidone copolymer, and an N,N-dimethylaminopropyl acrylamide/N,N-dimethylacrylamide copolymer. N,N-dimethylaminopropyl acrylamide/N,N-dimethylacrylamide copolymer is most preferable.

Specific examples of preferable copolymer of an acidic monomer and a monomer having an amide bond include a (meth)acrylic acid/N-vinylpyrrolidone copolymer, a (meth) acrylic acid/N,N-dimethylacrylamide copolymer, a 2-acrylamide-2-methylpropanesulfonic acid/N-vinylpyrrolidone copolymer, and a 2-acrylamide-2-methylpropanesulfonic acid/N,N-dimethylacrylamide copolymer. A (meth)acrylic acid/N,N-dimethylacrylamide copolymer is most preferable.

Specific examples of preferable copolymer of a basic monomer and a monomer having a hydroxyl group include an N,N-dimethylaminoethyl methacrylate/hydroxyethyl (meth)acrylate copolymer, an N,N-dimethylaminoethyl methacrylate/glycerol(meth)acrylate copolymer, an N,N-dimethylaminopropyl acrylamide/hydroxyethyl (meth)acrylate, and an N,N-dimethylaminopropyl acrylamide/glycerol (meth)acrylate copolymer. An N,N-dimethylaminoethyl methacrylate/hydroxyethyl (meth)acrylate copolymer is most preferable.

Specific examples of preferable copolymer of an acidic monomer and a monomer having an amide bond include a (meth)acrylic acid/hydroxyethyl (meth)acrylate copolymer, a (meth)acrylic acid/glycerol(meth)acrylate copolymer, a 2-acrylamide-2-methylpropanesulfonic acid/hydroxyethyl (meth)acrylate copolymer, and a 2-acrylamide-2-methylpropanesulfonic acid/glycerol(meth)acrylate copolymer. A (meth)acrylic acid/hydroxyethyl (meth)acrylate copolymer is most preferable.

In the case of using a copolymer of the basic monomer or acidic monomer and the other monomer, the copolymerization ratio [mass of basic monomer or acidic monomer]/[mass of the other monomer] is preferably from 1/99 to 99/1, more preferably from 2/98 to 90/10, and still more preferably from 10/90 to 80/20. When the copolymerization ratio is within the above range, functions such as lubricity and anti-fouling property against a lacrimal fluid are likely to be developed.

In order to change various characteristics, for example, thickness of the coating layer, it is possible to change molecular weights of an acidic polymer and a basic polymer. Specifically, when the molecular weight is increased, the thickness of the coating layer commonly increases. However, when the molecular weight is too large, it may become difficult to handle due to an increase in viscosity. Therefore, acidic polymers and basic polymers to be used in the present invention preferably have a molecular weight of 2,000 to 150,000. The molecular weight is more preferably from 5,000 to 100,000, and still more preferably from 75,000 to 100,000. The molecular weight of the acidic polymers and basic polymers is a polyethylene glycol-equivalent mass average molecular weight measured by a gel permeation chromatographic method (aqueous solvent).

Coating of the coating layer can be achieved by various methods disclosed, for example, in WO 99/35520, WO 01/57118, or U.S. Patent No. 2001-0045676.

In the medical device according to an embodiment of the present invention, a layer made of an acidic polymer and a basic polymer (hereinafter referred to as a coating layer) is formed, while at least a part inside the layer may be crosslinked. In the medical device of the present invention, at least a part may be crosslinked between the base material and the layer. Crosslinking means that polymers are bonded together by forming a crosslinking structure using their own functional group or crosslinking agent.

The above-mentioned crosslinking can be generated by irradiating with radiation in a case where at least an acidic polymer and a basic polymer are adhered to a base material. Radiations are preferably various ion beams, electron beams, positron beams, X-rays, γ rays, and neutron beams, more preferably electron beams and γ rays, and most preferably γ rays.

As mentioned above, satisfactory wettability and lubricity are imparted to a surface of a medical device by generating crosslinking inside a coating layer, or the space between a coating layer and a base material, and thus excellent comfort can be imparted. Meanwhile, crosslinking is also generated inside a base material by irradiating with radiation, and thus the medical device may become too hard. In that case, it is possible to suppress excess crosslinking inside the base material by appropriately replacing a component A in the base material by a component M, followed by copolymerization.

The present inventors have found a specific phenomenon, that is, when a coating liquid, used in so-called LbL coating of noncovalently applying plurality of polymers to a base material, is applied to a quartz resonator sensor (resonance frequency 9 MHz, AT-cut, gold electrode) in place of the base material in a device (including a medical device of the present invention) which is preferably used in a wet state or a semi-wet state, resonance frequency of each polymer to be measured increases (becomes larger). The present inventors have also found that a coating layer can form a surface which is satisfactory as a device (for example, medical device) in the case where a rate of increase in resonance frequency is large. Such device is preferably a soft resin device (tensile elastic modulus of 10 MPa or less). Such device preferably has low water content (water content of 10% by mass or less).

When AC voltage is applied to an electrode, the quartz resonator causes resonance vibration by the piezoelectric effect. However, when a substance adheres to a surface of the electrode surface to cause an increase in mass, the resonance frequency decreases (becomes smaller). In this case, a change in mass of the electrode surface is proportional to a change in resonance frequency to be measured. A method of detecting a change in mass due to adhesion of a substance, reaction or the like by a change in resonance frequency utilizing this principal is a quartz crystal microbalance (QCM).

For example, a resonance frequency measured by the above-mentioned QCM to a quartz resonator sensor obtained by bringing the above-mentioned quartz resonator sensor into contact with a first solution containing a first polymer is regarded as $F_1$; subsequently, a resonance frequency measured to a quartz resonator sensor obtained by bringing the this quartz resonator sensor into contact with a second solution containing a second polymer is regarded as $F_2$; and, furthermore, a resonance frequency measured to a quartz resonator sensor obtained by bringing the this quartz resonator sensor into contact with a third solution containing a third polymer is regarded as $F_3$. At this time, as a coating layer which satisfactory composes a surface, a value obtained by subtracting $F_1$ from $F_2$ ($F_2-F_1$, a rate of an increase in resonance frequency) or a value ($F_3-F_2$) obtained by subtracting $F_2$ from $F_3$ is preferably 1,500 or more, more preferably 2,000 or more, still more preferably 3,000 or more, and most preferably 4,000 or more. It is particularly preferred to satisfy the above conditions when the first solution or second solution is poly(meth)acrylic acid or polyethyleneimine. Since it is considered that an outermost surface portion exerts a large influence on characteristics of the surface, when the third polymer composes an outermost surface, $F_3-F_2$ is preferably 1,500 or more, more preferably 2,000 or more, still more preferably 3,000 or more, and most preferably 4,000 or more.

Even in the case of LbL coating including n steps (in total) of noncovalently applying first to nth polymers, not limiting to the above-mentioned first to third polymer, onto the base material, the same effects can be obtained. At this time, in a method for producing a medical device in which LbL coating is applied to a base material through n steps in total from a first step of bringing a base material into contact with a first solution containing a first polymer to thereby noncovalently apply the first polymer onto the base material to an nth step (n is an integer of 2 or more) of bringing the base material into contact with an nth solution containing an nth polymer to thereby noncovalently apply the nth polymer onto the base material, thus obtaining the medical device, in the case of bringing any one (k−1)th solution (k is an integer of 2 or more and n or less) of the first solution to the nth solution into contact with a quartz resonator sensor for quartz crystal microbalance (QCM), and quickly washing the quartz resonator sensor with pure water, followed by drying and further the measurement of a resonance frequency using the QCM to obtain a measured value $F_{k-1}$, subsequently bringing a kth solution into contact with this quartz resonator sensor, and quickly washing the quartz resonator sensor with pure water, followed by drying and further the measurement of a resonance frequency using the QCM to obtain a measured value $F_k$, a value ($F_k-F_{k-1}$) obtained by subtracting $F_{k-1}$ from $F_k$ is preferably 1,500 or more, more preferably 2,000 or more, still more preferably 3,000 or more, and even more preferably 4,000 or more. In the below-mentioned Examples, particularly satisfactory results are shown when ($F_k-F_{k-1}$) is 4,000 or more 6,000 or less. Since it is considered that an outermost surface portion exerts a large influence on characteristics of the surface, ($F_n-F_{n-1}$) is preferably 1,500 or more, more preferably 2,000 or more, still more preferably 3,000 or more, and most preferably 4,000 or more.

$F_k-F_{k-1}$ is preferably 30,000 or less, more preferably 20,000 or less, and still more preferably 10,000 or less.

Since it is considered that an outermost surface portion exerts a large influence on characteristics of the surface, it is preferred to apply an nth solution in which a value ($F_n-F_{n-1}$) obtained by subtracting $F_{n-1}$ from $F_n$ is preferably 1,500 or more, more preferably 2,000 or more, still more preferably 3,000 or more, and most preferably 4,000 or more.

In a combination of coating solutions for applying LbL coating to a medical device, including a first solution to an nth solution, wherein a coating solution containing a first polymer for noncovalently applying the first polymer onto a base material is used as a first solution, and a coating solution containing a kth polymer for noncovalently applying the kth polymer onto a base material is used as a kth solution (k is an integer of 2 or more and n or less, n is an integer of 2 or more), any one $F_k-F_{k-1}$ is preferably 1,500 or more, more preferably 2,000 or more, still more preferably 3,000 or more, and most preferably 4,000 or more. $F_k F_{k-1}$ is preferably 30,000 or less, more preferably 20,000 or less, and still more preferably 10,000 or less. Since it is considered that an outermost surface portion exerts a large influence on characteristics of the surface, regarding a combination of coating solutions, it is preferred to apply an (n−1)th solution and an nth solution in which $F_n-F_{n-1}$ is preferably 1,500 or more, more preferably 2,000 or more, still more preferably 3,000 or more, and most preferably 4,000 or more. The coating liquid is preferably the above-mentioned acidic polymer or basic polymer solution, or a combination thereof. The coating layer is preferably the above-mentioned layer made of an acidic polymer and a basic polymer. Furthermore, the solution containing the polymer preferably has high concentration of the polymer.

There is not necessarily clear understanding of a mechanism in which significant increase in resonance frequency in the case of applying LbL coating to a quartz resonator sensor serves as an indicator for formation of a satisfactory surface on a base material. However, as is apparent from the below-mentioned Examples, it is the verified fact that significant increase in resonance frequency in the case of applying LbL coating to a quartz resonator sensor serves as an indicator for formation of a satisfactory surface on a base material.

The method for producing a medical device of the present invention will be described below. The medical device of an embodiment of the present invention is obtained by coating a surface of a molding (base material) with each of an acidic polymer solution and a basic polymer solution 1 to 5 times, more preferably 1 to 3 times, and still more preferably 1 to 2 times, to form a coating layer. The number of times of the coating step of an acidic polymer solution may be different from that of the coating step of a basic polymer solution.

The present inventors have found that excellent wettability and lubricity can be imparted by very small number of times of the coating steps (total number of coating steps with one or more kinds of acidic polymer solutions and coating steps with one or more kinds of basic polymer solutions is 2 or 3) in the method for producing a medical device of the present invention. This fact is crucially important for industry from the viewpoint of shortening of the production process. In that sense, the total number of coating steps of acidic polymer solutions and coating steps of basic polymer solutions is preferably 2 or 3, and more preferably 2.

The present inventors have also confirmed that wettability and lubricity are scarcely developed only by performing either the coating step of an acidic polymer solution or the coating step of a basic polymer solution once in the medical device of the present invention.

From the viewpoint of wettability, lubricity and shortening of the production process, coating of the coating layer is preferably performed with any constitution selected from the following constitutions 1 to 4. The following notation shows that the respective coating steps are sequentially applied to a surface of a molding from left to right.

Constitution 1: Coating of basic polymer solution/coating of acidic polymer solution Constitution 2: Coating of acidic polymer solution/coating of basic polymer solution Constitution 3: Coating of basic polymer solution/coating of acidic polymer solution/coating of basic polymer solution Constitution 4: Coating of acidic polymer solution/coating of basic polymer solution/coating of acidic polymer solution Among these constitutions, constitution 4 is more preferable since the obtained medical device exhibits particularly excellent wettability.

In the above constitution 1 to constitution 4, at least one of an acidic polymer and a basic polymer used in each coating step is preferably a polymer having a group selected from a hydroxyl group and an amide group. At least one kind of an acidic polymer and a basic polymer is particularly preferably a polymer having a hydroxyl group. At least two kinds of acidic polymers and basic polymers are more preferably polymers having a group selected from a hydroxyl group and an amide group.

In the above constitution 1 to constitution 4, it is possible to use one or more kinds of basic polymer solutions and/or one or more kinds of acidic polymer solutions. For example, an acidic polymer solution used in a solution to be applied first or last in constitution 4 may be an acidic polymer solution of the same kind and the same concentration (or different concentration), or different kinds of acidic polymer solutions may be used.

In the case of coating an acidic polymer solution and a basic polymer solution, a surface of a base material may be untreated or already treated. As used herein, the phrase "surface of a base material is already treated" means that a surface of a base material is subjected to a surface treatment or surface modification by a known method. Suitable examples of the surface treatment or surface modification include a plasma treatment, a chemical modification, a chemical functionalization, a plasma coating and the like.

One of preferred aspects of the method for producing a medical device of the present invention includes the following steps 1 to 4 in this order:

<Step 1>

Step of polymerizing a mixture of a component A which is a polysiloxane compound having a plurality of polymerizable functional groups per molecule, and also having a number average molecular weight of 6,000 or more, and a component B which is a polymerizable monomer having a fluoroalkyl group to obtain a molding;

<Step 2>

Step of bringing the molding into contact with an acidic polymer solution, and then washing the molding to remove the surplus acidic polymer solution;

<Step 3>

Step of bringing the molding into contact with a basic polymer solution, and then washing the molding to remove the surplus basic polymer solution; and <Step 4>

Step of bringing the molding into contact with an acidic polymer solution, and then washing the molding to remove the surplus acidic polymer solution.

As mentioned above, a layer made of an acidic polymer and a basic polymer can be formed on a molding by sequentially bringing the molding into contact with an acidic polymer solution and a basic polymer solution. Thereafter, surplus polymer is preferably removed by sufficiently washing.

It is possible to apply, as the method of bringing the molding into contact with an acidic polymer solution or a basic polymer solution, various coating methods such as an immersion method (dipping method), a brush coating method, a spray coating method, a spin coating method, a die coating method and a squeegee method.

When contact with a solution is performed by an immersion method, immersion time can vary depending on various factors. Immersion of a molding in an acidic polymer solution or a basic polymer solution is preferably performed for 1 to 30 minutes, more preferably 2 to 20 minutes, and most preferably 1 to 5 minutes.

The concentration of an acidic solution and a basic polymer solution can vary depending on properties of an acidic polymer or a basic polymer, thickness of a desired coating layer, and other various factors. The concentration of the acidic or basic polymer is preferably 0.001% by mass or more and 10% by mass or less, more preferably 0.6% by mass or more and 5% by mass or less, and most preferably 1% by mass or more and 3% by mass or less.

The pH of an acidic polymer solution and a basic polymer solution is preferably maintained within a range from 2 to 5, and more preferably from 2.5 to 4.5.

Removal of surplus acidic polymer and basic polymer by washing is commonly performed by rinsing a molding after coating using clean water or an organic solvent. Rinsing is preferably performed by immersing the molding in water or an organic solvent or exposing to a water flow or an organic solvent flow. Rinsing may be completed in one step. However, it was recognized that it is efficient that a rinsing step is performed plural times. Rinsing is preferably performed in 2 to 5 steps. Immersion of each molding in a rinsing solution is preferably performed for 1 to 3 minutes.

Pure water is also preferably used as the rinsing solution. In order to increase adhesion of a coating layer, it is preferred to use an aqueous buffered solution having pH adjusted within a range from 2 to 7, more preferably from 2 to 5, and still more preferably from 2.5 to 4.5.

The step of drying or removing an excess rinsing solution may also be included. A molding can be dried to some extent by merely being left to stand under air atmosphere. Drying is preferably accelerated by supplying a mild air flow to the surface. Flow rate of the air flow can be adjusted as a function of the strength of a material to be dried, and mechanical fixturing of a material. There is no need to completely dry a molding. Herein, it is important to remove droplets of a solution adhered onto a surface of the molding as compared with drying of the molding. Therefore, the molding is only dried until a film of water or a solution on the surface of the mold is removed, leading to shortening of the process time, favorably.

It is preferred that an acidic polymer and a basic polymer are alternately coated. It is possible to obtain a medical device, which has excellent wettability and lubricity that cannot be obtained by one of these polymers, and also has excellent comfort, by alternately coating the polymers.

The coating layer can be asymmetric. As used herein, "asymmetric" refers to the fact that a coating layer formed on a first side of a medical device is different from that formed on a second side opposite the first side. As used herein, "different coating layers" refer to the fact that a coating layer formed on a first side and a coating layer formed on a second side each has different surface characteristics or functionalities.

The thickness of the coating layer can be controlled by adding one or more salts such as sodium chloride to an acidic polymer solution or a basic polymer solution. The concentration of the salt is preferably from 0.1 to 2.0% by mass. As the concentration of the salt increases, a polyelectrolyte exhibits a more spherical spatial structure. However, when the concentration becomes too high, even if the polyelectrolyte is deposited on a surface of a molding, it is not satisfactorily deposited. More preferably, the concentration of the salt is from 0.7 to 1.3% by mass.

One of other preferred aspects of the method for producing a medical device of the present invention further includes the following step 5;

<Step 5>

Step of irradiating the molding, obtained by the method including the above steps 1 to 4 in this order, with radiation.

Irradiation with radiation may be carried out in a state where a molding is immersed in a coating liquid, or may be carried out after pulling up the molding from the coating liquid and further washing. Irradiation with radiation may also be preferably carried out in a state where a molding is immersed in a liquid other than the coating liquid. In this case, it is preferred that radiation acts more efficiently. In this case, it is possible to apply, as a solvent for a liquid in which the coated molding is immersed, various organic and inorganic solvents, and there is no particular limitation. Examples thereof include various alcohol-based solvents such as water, methanol, ethanol, propanol, 2-propanol, butanol, tert-butanol, tert-amyl alcohol, and 3,7-dimethyl-3-octanol; various aromatic hydrocarbon-based solvents such as benzene, toluene, and xylene; various aliphatic hydrocarbon-based solvents such as hexane, heptane, octane, decane, petroleum ether, kerosene, ligroin, and paraffin; various ketone-based solvents such as acetone, methyl ethyl ketone, and methyl isobutyl ketone; various ester-based solvents such as ethyl acetate, butyl acetate, methyl benzoate, dioctyl phthalate, and ethylene glycol diacetate; and various glycol ether-based solvents such as diethylether, tetrahydrofuran, dioxane, ethylene glycol dialkyl ether, diethylene glycol dialkyl ether, triethylene glycol dialkyl ether, tetraethylene glycol dialkyl ether, polyethylene glycol dialkyl ether, a polyethylene glycol-polypropylene glycol block copolymer, and a polyethylene glycol-polypropylene glycol random copolymer; and these solvents can be used alone or in combination. Among these, water is most preferable. When irradiation with radiation is carried out in a state where a molding is immersed in an aqueous liquid, an aqueous liquid is suitably, in addition to pure water, saline, a phosphate-based buffer (preferably pH of 7.1 to 7.3), or a borate-based buffer (preferably pH of 7.1 to 7.3).

Irradiation with radiation in a state where a molding is sealed in a container has a merit capable of simultaneously performing sterilization of the molding.

γ rays are preferably used as radiations. In this case, too small γ dose may fail to obtain sufficient bonding between a molding and a coating layer, while too large γ dose may cause deterioration of physical properties of a molding. Therefore, the dose is preferably from 0.1 to 100 kGy, more preferably from 15 to 50 kGy, and most preferably from 20 to 40 kGy. Thereby, at least a part inside a coating layer and at least a part of the space between a coating layer and a molding are crosslinked, thus enabling an improvement in resistance (for example, scrubbing resistance) of the coating layer.

The medical device of the present invention is useful as lenses for eye, such as low water content soft contact lens, intraocular lens, an artificial cornea, a corneal inlay, a corneal onlay, and a spectacle lens. The medical device is particularly suited for a low water content soft contact lens. It is also possible to apply as the above-mentioned medical device only by changing the shape of the medical device of the present invention.

Embodiments of the low water content soft device for eye according to the present invention will be described below. The present embodiment is directed to a low water content soft device for eye to be worn in the eye, having a medical device having an elastic modulus of 100 kPa or more and 2,000 kPa or less, a water content of 10% by mass or less, a tensile elongation of 50% or more and 3,000% or less, and a dynamic contact angle (advancing angle) relative to a borate buffer of 80° or less, an iris-like pattern being formed on at least a part of the low water content soft device for eye.

Another embodiment of the low water content soft device for eye according to the present invention is directed to a low water content soft device for eye, wherein a layer made of an acidic polymer and a basic polymer is formed on at least a part of the low water content soft device for eye, an iris-like pattern being formed on at least a part of the low water content soft device for eye.

As used herein, low water content means that the water content is 10% by mass or less. Soft means that the tensile elastic modulus is 10,000 kPa or less.

The iris pattern may be formed on a surface of a base material, or formed inside a base material, or formed inside a coating layer. In other words, the iris pattern can be formed at the position where it is not exposed on an outer surface of a low water content soft lens for eye.

When the above-mentioned iris pattern is applied to a lens for eye which is a hydrous lens as usual and has low oxygen permeability, the oxygen permeability is further decreased by printing or interposing the iris pattern. Wear of a lens having low oxygen permeability for a long time may cause ocular hyperemia and impart feeling of fatigue to wearers. Meanwhile, since the low water content soft device for eye according to the present invention has high oxygen permeability, it exerts the effect of maintaining high oxygen permeability even if the iris pattern is imparted, thus imparting no feeling of fatigue to wearers, and also preventing the cornea from causing serious lacking of oxygen.

Since the low water content soft device for eye according to the present invention has low water content, a lens tends to cause less movement during wear as compared with a hydrous lens to thereby prevent an iris pattern from shifting during wear, and thus the device can be used as a lens for eye, which is excellent in aesthetics. It is not preferred that the lens significantly moves in the eye during wear since the iris of wearers may shift from the iris pattern and, for example, wearers look like as if they have an elliptic, iris, or the white portion is exposed from the space between the iris pattern and iris, resulting in deterioration of aesthetics.

First Embodiment

A low water content soft contact lens as one of embodiments of the low water content soft device for eye according to the present invention will be described below. In the present embodiment, an iris-like pattern covers a surface of an iris to thereby pseudo-color the iris.

In the low water content soft lens for eye according to present first embodiment, an iris pattern, which is a pattern replicating an iris, is formed.

Figure 4:
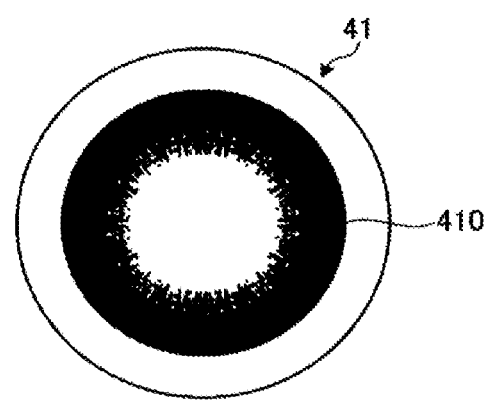
FIG. 4 is a schematic view showing an example of an iris pattern of a low water content soft device for eye according to an embodiment of the present invention.

To the low water content soft lens for eye according to the present first embodiment, an iris pattern as shown in FIG. 4 is imparted by printing as an example. It is also possible to impart the iris pattern by a method other than printing. Preferred example thereof includes a method of imparting a film-like product having an iris pattern on or in a base material of a low water content soft lens for eye. An iris pattern 410 of a low water content soft lens for eye 41 shown in FIG. 4 is a pattern which has an approximately circular ring shape whose periphery has a diameter identical to or larger than that of the iris, light permeability increasing toward the center. In the case of wearing a lens on the eye, the iris pattern 410 locates on an iris and covers at least a part of the iris to thereby pseudo-color the iris. Accordingly, formation of the iris pattern 410 enables pseudo change in color or size of the iris portion of lens wearers, and thus excellent aesthetics can be imparted to lens wearers. The iris pattern 410 also enables an improvement in design properties of the low water content soft lens for eye 41 per se.

The diameter of the periphery side of the iris pattern 410 is preferably from 9.0 to 11.0 mm. From the viewpoint of imparting satisfactory visual sense to wearers, the iris pattern preferably include an optically transparent portion at the center portion of the lens. This optically transparent portion is preferably a whole area inside a circle of 1 mm in diameter, which has the center of the lens as a center. The optically transparent portion is more preferably a whole area inside a circle of 1.5 mm in diameter, which has the center of the contact lens as a center, still more preferably a whole area inside a circle of 2 mm in diameter, and most preferably a whole area inside a circle of 2.5 mm in diameter. The optically transparent portion may be colored, and preferably substantially colorless.

Second Embodiment

A low water content soft contact lens as one of other embodiments of a low water content soft device for eye according to the present invention will be described below. In the present embodiment, an iris-like pattern is a light shielding pattern having a circular ring shape in which an optical pupil having a diameter of 2.0 mm or less is formed in the center of the pattern.

Figure 5:
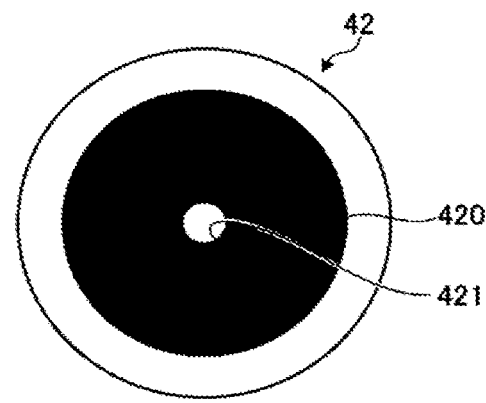
FIG. 5 is a schematic view showing an example of an iris pattern of a low water content soft contact lens for eye according to an embodiment of the present invention.

FIG. 5 is a schematic view showing an example of an iris pattern of a low water content soft device for eye according to the present second embodiment of the present invention. An iris pattern 420 of a low water content soft lens for eye 42 shown in FIG. 5 is a light shielding pattern having a circular ring shape in which an optical pupil 421 (pinhole) having a diameter 2.0 mm or less is formed in the center portion. Formation of a diaphragm (hole) like the optical pupil 421 in the iris pattern 420 enables continuous clear vision of objects which are any distance away, irrespective of hyperopia, myopia, astigmatism, and presbyopia. Therefore, it becomes possible to continuously follow the object in a clear state with the center of the eye without exchanging the lens.

The shape of the optical pupil 421 is preferably approximately circle, and most preferably perfect circle, so as to obtain clear visual sense. The diameter of the optical pupil 421 is preferably from 1.0 to 1.6 mm. The diameter of the optical pupil 421 is a maximum value of lengths of a line segment joining any two points on a periphery (circumference in the case of a circle) of the optical pupil.

The diameter of the outer periphery side of the iris pattern 420 is preferably from 4.0 to 9.0 mm. The iris pattern may be formed on a surface of a base material, or formed inside a base material, or formed inside a coating layer. In other words, the iris pattern can be formed at the position where it is not exposed on an outer surface of a low water content soft lens for eye.

The low water content soft contact lens as another aspect of the present invention is a low water content soft contact lens to be worn in the eye, in which a lacrimal fluid exchange-promoting pattern for promoting exchange of a lacrimal fluid between the lens and the eye is formed. The lacrimal fluid exchange-promoting pattern is formed to a base material. Thereafter, the above-mentioned coating layer is preferably formed to the base material to which the lacrimal fluid exchange-promoting pattern has been formed.

The low water content soft contact lens in which the lacrimal fluid exchange-promoting pattern has been formed to the base material, followed by coating with the above-mentioned coating layer (a layer made of an acidic polymer and a basic polymer) enables a reduction in a surface area in contact with the cornea during wear and a reduction in retention of a lacrimal fluid containing a sticky substance (mucin), and thus the effect of more reducing adhesion to the cornea can be expected. It is also possible to expect the effect of maintaining soundness of the eye by enabling satisfactory lacrimal fluid exchange.

In the present invention, the lacrimal fluid exchange-promoting pattern is suitably at least one selected from a hole (hereinafter referred to as a through hole) which penetrate trough through a contact lens from a back surface (eyeball side) to a front surface (eyelid side) during wear, a groove, or a pleats structure, or a combination thereof. The shape of the through hole is preferably a shape selected from polygon, circle, and ellipse, and more preferably a shape selected from circle and ellipse.

It is not preferred that the diameter of the through hole is too small since the lacrimal fluid exchange-promoting effect may be degraded and also the through hole may be closed when components in the lacrimal fluid adhere as stains. The diameter of the through hole is preferably 0.1 mm or more, more preferably 0.2 mm or more, still more preferably 0.5 mm or more, and most preferably 0.8 mm or more. It is not preferred that the diameter of the through hole is too large since the contact lens tends to be damaged. The diameter of the through hole is preferably 5 mm or less, more preferably 4 mm or less, still more preferably 3 mm or less, and most preferably 2 mm or less. The diameter of the through hole is a maximum value of lengths of a line segment joining any two points on a periphery (for example, circumference in the case of a circle) of the through hole.

It is not preferred that the number of through holes is too small since the lacrimal fluid exchange-promoting effect tends to be degraded. The number of through holes is preferably 2 or more, more preferably 3 or more, still more preferably 6 or more, and most preferably 8 or more, per contact lens. It is not preferred that the number of through holes is too large since the contact lens tends to be damaged. The number of through holes is preferably 1,000 or less, more preferably 240 or less, still more preferably 120 or less, and most preferably 60 or less.

The groove is preferably formed on a back surface of a molding. It is also preferred that a part of the groove penetrates a front surface of the molding. It is preferred that the groove is formed along a diameter direction of the contact lens. It is preferred to dispose a plurality of grooves, and it is also possible to form a structure in which grooves are connected with another groove.

It is not preferred that the width of the groove is too small since the lacrimal fluid exchange-promoting effect tends to be degraded. The width of the groove is preferably 0.1 mm or more, more preferably 0.2 mm or more, still more preferably 0.5 mm or more, and most preferably 0.8 mm or more. It is not preferred that the width of the groove is too large since a contact lens tends to be damaged. The diameter of a through hole is preferably 5 mm or less, more preferably 4 mm or less, and still more preferably 3 mm or less, and most preferably 2 mm or less.

It is not preferred that the number of grooves (countable) is too small since the lacrimal fluid exchange-promoting effect tends to be degraded. The number of through holes is preferably 2 or more, more preferably 3 or more, still more preferably 6 or more, and most preferably 8 or more, per contact lens. It is not preferred that the number of grooves (countable) is too large since a contact lens tends to be damaged. The number of grooves is preferably 1,000 or less, more preferably 240 or less, still more preferably 120 or less, and most preferably 60 or less.

From the viewpoint of imparting satisfactory visual sense to wearers, it is preferred that a lacrimal fluid exchange-promoting pattern is not formed in the center portion of a low water content soft contact lens. The region where a lacrimal fluid exchange-promoting pattern is to be formed is preferably outside a circle of 1 mm in diameter, which has the center of a contact lens as a center, more preferably outside a circle of 2 mm in diameter, and still more preferably outside a circle of 3 mm in diameter.

From the viewpoint of disposing a lacrimal fluid exchange-promoting pattern while avoiding a region of sensitive tactile sensation to obtain a low water content soft contact lens which is excellent in comfort, the region where a lacrimal fluid exchange-promoting pattern is to be formed is preferably outside a circle of 3.5 mm in diameter, which has the center of a contact lens as a center, more preferably outside a circle of 4 mm in diameter, and still more preferably outside a circle of 4.5 mm in diameter.

Figure 6:
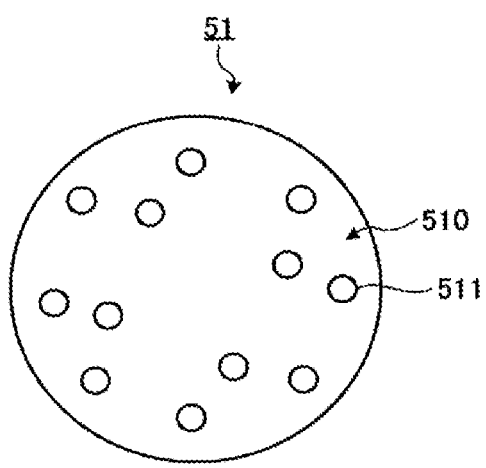
FIG. 6 is a schematic view showing an example of a lacrimal fluid exchange-promoting pattern of a low water content soft contact lens for eye according to an embodiment of the present invention.

For example, a lacrimal fluid exchange-promoting pattern 510 of a low water content soft contact lens 51 shown in FIG. 6 is provided with a plurality of through holes 511 formed between a center portion and an outer edge in a diameter direction of the low water content soft contact lens 51.

It is possible to maintain soundness of the eye by promoting exchange of lacrimal fluid between the low water content soft contact lens 51 and the eye through the through hole 511 of the above-mentioned lacrimal fluid exchange-promoting pattern 510. Since the low water content soft contact lens 51 in which the lacrimal fluid exchange-promoting pattern 510 has been formed can promote lacrimal fluid exchange, excellent comfort can be obtained.

Figure 7:
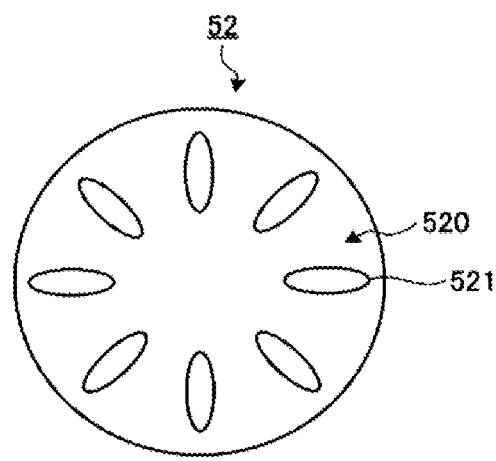
FIG. 7 is a schematic view showing an example of a lacrimal fluid exchange-promoting pattern of a low water content soft contact lens for eye according to Variation 1 of an embodiment of the present invention.

FIG. 7 is a schematic view showing an example of a lacrimal fluid exchange-promoting pattern of a low water content soft contact lens for eye according to Variation 1 of the embodiment of the present invention. A lacrimal fluid exchange-promoting pattern 520 of a low water content soft contact lens 52 shown in FIG. 7 is provided by arranging a plurality of through holes 521, each having an approximately elliptical shape, so that a major axis direction of this ellipse corresponds to a diameter direction of the low water content soft contact lens 52.

Figure 8:
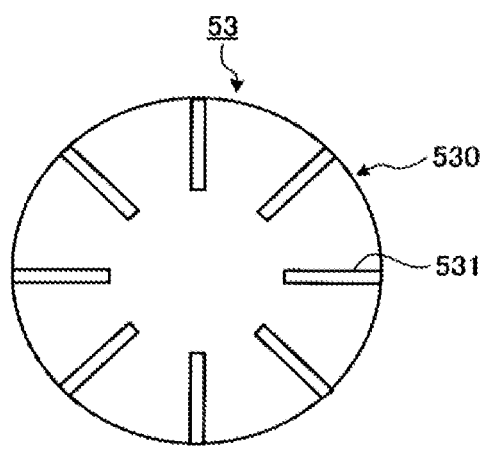
FIG. 8 is a schematic view showing an example of a lacrimal fluid exchange-promoting pattern of a low water content soft contact lens for eye according to Variation 2 of an embodiment of the present invention.

FIG. 8 is a schematic view showing an example of a lacrimal fluid exchange-promoting pattern of a low water content soft contact lens for eye according to Variation 2 of the embodiment of the present invention. A lacrimal fluid exchange-promoting pattern 530 of a low water content soft contact lens 53 shown in FIG. 8 is provided by arranging a plurality of groove 531, each having an approximately rectangular shape, so that one end portion of a major axis runs along with an outer edge of the low water content soft contact lens 53, and also a major axis direction corresponds to a diameter direction of the low water content soft contact lens 3.

The lacrimal fluid exchange-promoting patterns 510 to 530 shown in the above-mentioned FIGS. 6 to 8 are formed to a base material. Thereafter, the above-mentioned coating layer is formed to a base material on which the lacrimal fluid exchange-promoting pattern has been formed. The lacrimal fluid exchange-promoting pattern to be formed on the base material may be composed of a combination of the lacrimal fluid exchange-promoting patterns 510 to 530 shown in the above-mentioned FIGS. 6 to 8.

One (aspect P1) of preferred aspects of the method for producing a low water content soft contact lens of the present aspect includes the following steps 1 to 3 in this order:
<Step 1>
Step of polymerizing a mixture of monomers to obtain a lens-shaped molding having a lacrimal fluid exchange-promoting pattern;
<Step 2>
Step of bringing the molding into contact with a basic polymer solution, and then washing the molding to remove the surplus basic polymer solution; and
<Step 3>
Step of bringing the molding into contact with an acidic polymer solution, and then washing the molding to remove the surplus acidic polymer solution.

As mentioned above, a layer made of an acidic polymer and a basic polymer can be formed on a lens-shaped molding by sequentially bringing the molding into contact with an acidic polymer solution and a basic polymer solution. Thereafter, surplus polymer is preferably removed by sufficiently washing.

It is preferred that a lens-shaped molding having a lacrimal fluid exchange-promoting pattern is obtained using a mold having a shape which imparts a lacrimal fluid exchange-promoting pattern in the step 1.

One (aspect P2) of another preferred aspect of the method for producing a low water content soft contact lens of the present invention includes the following steps 1 to 4 in this order:
<Step 1>
Step of polymerizing a mixture of monomers to obtain a lens-shaped molding;
<Step 2>
Step of forming a lacrimal fluid exchange-promoting pattern to the molding;
<Step 3>
Step of bringing the molding into contact with a basic polymer solution, and then washing the molding to remove the surplus basic polymer solution; and
<Step 4>
Step of bringing the molding into contact with an acidic polymer solution, and then washing the molding to remove the surplus acidic polymer solution.

When the lacrimal fluid exchange-promoting pattern is a through hole, in the step of forming a lacrimal fluid exchange-promoting pattern to a lens-shaped molding in the aspect P2 (step 2), the lacrimal fluid exchange-promoting pattern is preferably formed before separating from a mold made of a resin used for molding the molding. Thereby, it is possible to stably perforate a hole (lacrimal fluid exchange-promoting pattern) in a state where the molding is fixed. It is possible to apply, as a method of forming a through hole, a method of chemically perforating using a drill, a punch, a die cutting blade or the like, a method of perforating using a laser, and a method of perforate using a chemical.

EXAMPLES

The present invention will be specifically described below by way of Examples, but the present invention is not limited thereto.

<Borate Buffer>
As used herein, a borate buffer is a "salt solution" disclosed in Example 1 of Kohyo (National Publication of Translated Version) No. 2004-517163. Specifically, it is an aqueous solution in which 8.48 g of sodium chloride, 9.26 g of boric acid, 1.0 g of sodium borate (sodium tetraborate decahydrate), and 0.10 g of ethylenediaminetetraacetic acid are dissolved in pure water to make 1,000 mL.

<Saline>
As used herein, saline means an aqueous solution in which sodium chloride is dissolved in pure water to thereby control the concentration to 0.9% by mass.

<Wet State>
As used herein, wet state means a state where a specimen is immersed in pure water or a predetermined aqueous solution at room temperature (25° C.) for 24 hours or more. The measurement of mechanical properties in a wet state is carried out as soon as possible after pulling out the specimen from pure water or a predetermined aqueous solution.

<Dry State>
As used herein, dry state means a state where a specimen in a wet state is vacuum-dried at 40° C. for 16 hours. The degree of vacuum in the vacuum drying is set at 2 hPa or less. The measurement of mechanical properties in a dry state is carried out as soon as possible after the vacuum drying.

<Analysis Method and Evaluation Method>
(1) Molecular Weight
Polystyrene-equivalent mass average molecular weight and number average molecular weight of each component used for abase material were measured by a GPC method under the following conditions.
Pump: TOSOH DP-8020
Detector: TOSOH RI-8010
Column oven: Shimadzu CTO-6A
Auto-sampler: TOSOH AS-8010
Column: TOSOH TSKgel GMHHR-M (7.8 mm in inner diameter×30 cm, 5 μm in particle diameter)×two columns
Column temperature: 35° C.
Mobile phase: chloroform
Flow rate: 1.0 mL/minute
Sample concentration: 0.4% by mass
Injection amount: 100 μL
Standard sample: polystyrene (having a molecular weight of 1,010 to 1,090,000)
(2) Transparency A specimen in a state of being wetted with a borate buffer was visually observed and transparency was evaluated by the following criteria.
A: Transparent with no turbidity
B: White turbidity with about intermediate degree between A and C
C: Semi-transparent with white turbidity
D: White turbidity with about intermediate degree between C and E
E: White turbidity with no transparency
(3) Water Content A contact lens-shaped specimen or a film-shaped specimen was used. After hydrating the specimen by immersing in a borate buffer and being left to stand at room temperature for 24 hours or more, water on a surface was wiped off by a wiping cloth ("Kimwipe®)", manufactured by NIPPON PAPER CRECIA Co., LTD.) and the mass (Ww) was measured. Then, the specimen was dried by a vacuum drying oven at 40° C. for 16 hours and the mass (Wd) was measured. Then, water content was determined by the following equation. In the case the obtained value is less than 1%, it was written as "less than 1%".

Water content (%)=100×($Ww$−$Wd$)/$Ww$ (4) Water Wettability

A specimen was immersed in a borate buffer in a beaker at room temperature for 24 hours or more. The beaker containing the specimen and the borate buffer was exposed to ultrasonic using an ultrasonic cleaner (for 1 minute). The specimen was pulled up from the borate buffer and the specimen was held in air so that a surface (diameter direction in the case that the specimen has a contact lens shape) becomes vertical. A state of the surface of the specimen was visually observed, and then judged by the following criteria. The diameter is a diameter of a circle formed by an outer edge portion of a contact lens.
A: A liquid film on a surface is held for 20 seconds or more.
B: A liquid film on a surface is broken within 10 to 20 seconds.
C: A liquid film on a surface is broken within 5 to 10 seconds.
D: A liquid film on a surface is broken within 1 to 5 seconds.
E: A liquid film on a surface is broken instantly (within 1 second).
(5) Measurement of Dynamic Contact Angle Using samples in a state of being wetted with a borate buffer, the measurement was carried out. Using, as dynamic contact angle samples, film-shaped specimens each measuring about 5 mm×10 mm×0.1 mm cut out from samples molded into a film, or strip-shaped specimens of 5 mm in width cut out from contact lens-shaped samples, advancing dynamic contact angle relative to a borate buffer was measured. A dynamic wettability tester WET-6000 manufactured by RHESCA Corporation was used as a measurement apparatus. An immersion rate was set at 0.1 mm/second, and an immerse depth was set at 7 mm.
(6) Tensile Elastic Modulus, Tensile Elongation (Elongation at Break)

Figure 2:
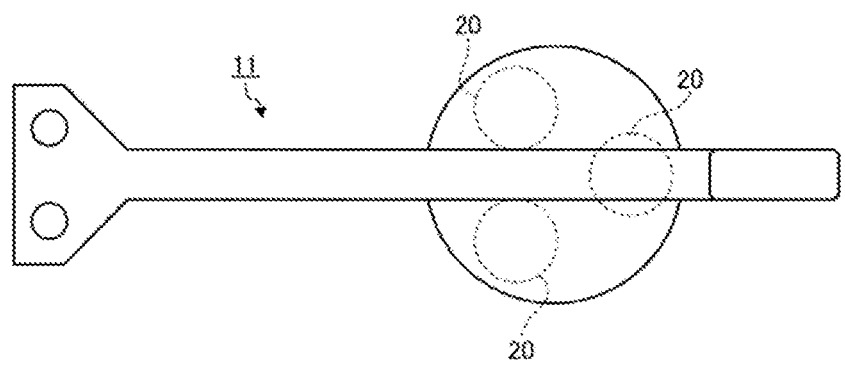
FIG. 2 is a schematic view showing the constitution of the main part of a measurement jig and a friction block for measuring a coefficient of surface friction of a sample of a medical device according to Example of the present invention, as seen from a direction A shown in FIG. 1.
Figure 3:
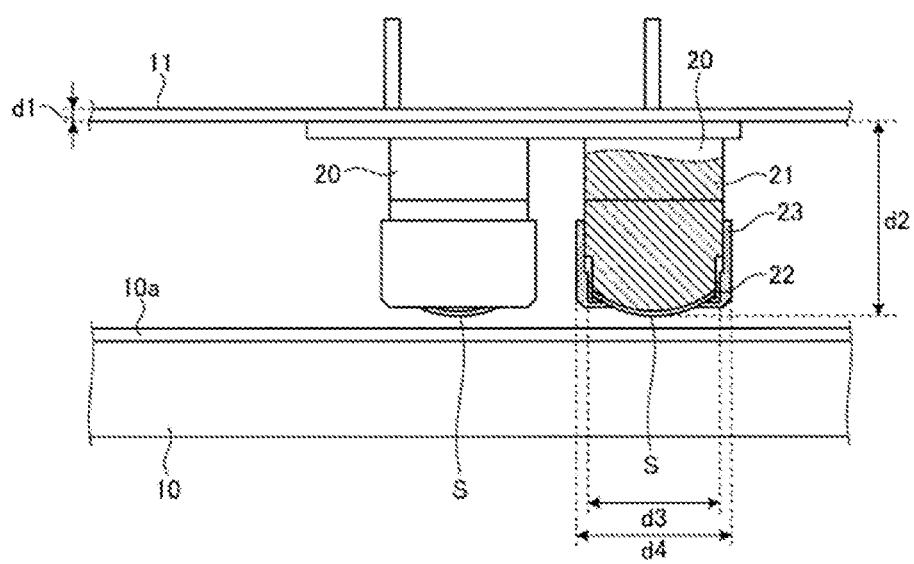
FIG. 3 is a partial cross-sectional view showing the constitution of the main part of a measurement jig and a friction block for measuring a surface friction coefficient of a sample of a medical device according to Example of the present invention.

Using samples in a state of being wetted with a borate buffer, the measurement was carried out. Using a prescribed blanking die, specimens each measuring 5 mm in width (minimum portion), 14 mm in length and 0.2 mm in thickness were cut out from contact lens-shaped samples. Using the specimens, a tensile test was carried out by a tester Model RTG-1210, manufactured by ORIENTEC Co., Ltd. (load cell Model UR-10N-D). A testing speed was 100 mm/minute, and a distance between grips (initial) was 5 mm. In the case of film-shaped samples, the measurement was carried out in the same manner using specimens each measuring about 5 mm×20 mm×0.1 mm.
(7) Lubricity Lubricity was subjected to sensory evaluation after rubbing samples (contact lens shape or film shape) in a state of being wetted with a borate buffer five times with a finger of a person.
A: Excellent lubricity
B: About intermediate lubricity between A and C
C: Moderate lubricity
D: Little lubricity (about intermediate lubricity between C and E)
E: No lubricity
(8) Adhesion of Mucin Mucin, Bovine Submaxillary Gland (Catalog No. 499643) manufactured by CALBIOCHEM Corporation was used as mucin. Contact lens-shaped samples were immersed in an aqueous mucin solution having a concentration of 0.1% under the conditions of 37° C. for 20 hours, and then the amount of mucin adhered to samples was determined by a bicinchoninic acid (BCA) protein assay method.
(9) Adhesion of Lipid In a 500 ml beaker, a stirring bar (36 mm) was placed, and 1.5 g of methyl palmitate and 500 g of pure water were charged. A temperature of a water bath was set at 37° C. and the above beaker was placed in the center of the water bath, followed by stirring for one hour using a magnetic stirrer. A rotation speed was set at 600 rpm. Contact lens-shaped samples were put in a lens basket one by one and then put in the above beaker, followed by stirring. After 1 hour, stirring was stopped and samples in the lens basket were subjected to rubbing cleaning using city water at 40° C. and a liquid detergent for domestic use ("Mamalemon®", manufactured by Lion Corporation). After cleaning, samples were put in a screw tube containing a borate buffer and then immersed in an ice bath for 1 hour. After pulling out the screw tube from the ice bath, white turbidity of samples was visually observed and the amount of methyl palmitate adhered to samples was judged by the following criteria.
A: Transparent with no white turbidity
B: Slight white turbidity is observed
C: Considerable white turbidity is observed
D: White turbidity accounts for most part
E: White turbidity accounts for entirety
(10) Artificial Lacrimal Fluid Immersion Test A tear-like fluid (TLF) buffer solution, which was prepared in accordance with the method disclosed in lines 5 to 36 on page 32 of WO 2008/127299 pamphlet, except that oleic acid is used in place of the oleic acid propyl ester, was used as an artificial lacrimal fluid. In 1 well of a multiplate for culture (24-well model, material: polystyrene, radiosterilized), 2 mL of an artificial lacrimal fluid was charged and then one sample (with contact lens shape) was immersed. Shaking was carried out at 100 rpm and 37° C. for 24 hours. After pulling out the sample, the sample was lightly washed with a phosphate buffer solution (PBS; pH of about 7.2) and then immersed in the well in which the artificial lacrimal fluid was replaced by 2 mL of an artificial lacrimal fluid. Furthermore, after shaking at 100 rpm and 37° C. for 24 hours, the sample was lightly washed with PBS and the amount of deposits was observed by visually evaluating the degree of white turbidity of the sample. The evaluation was carried out according to the following criteria.
A: No white turbidity is observed.
B: Slight white turbidity (less than 10% of area) is observed
C: Considerable white turbidity (10 to 50% of area) is observed
D: White turbidity accounts for most part (50 to 100% of area), while back side can be seen through
E: Thick white turbidity accounts for entirety, while back side cannot be easily seen through
(11) Degree of Pigmentation Degree of pigmentation (depth of blue color) of samples in a state of being wetted with a borate buffer was visually observed and then evaluated according to the following criteria.
A: Coloration is recognized at a glance
B: About intermediate degree between A and C of pigmentation
C: Slight coloration is recognized
D: About intermediate degree between C and D of pigmentation
E: No coloration is recognized
(12) Surface Friction Coefficient Using contact lens-shaped samples or film-shaped samples cut into a circle shape having a diameter of 14 mm, the measurement was carried out. Friction feeling tester KES-SE (Kato Tech Co., Ltd.) was used as a measurement apparatus. FIG. 1 is a schematic view showing an apparatus for measuring a surface friction coefficient. FIG. 2 is a schematic view showing the constitution of the main part of a measurement jig 11 and a friction block 20, as seen from a direction A shown in FIG. 1. FIG. 3 is a partial cross-sectional view showing the constitution of the main part of a measurement jig 11 and a friction block 20. First, a plate made of Teflon® (measuring 65 mm×100 mm×1.0 mm, omitted in FIG. 3) was horizontally disposed on a sample stand 10 of an apparatus 1, and then a quartz glass plate 10a having a smooth surface (measuring 55 mm×90 mm×1.0 mm) was horizontally disposed and fixed thereon. Plates having sufficiently high flatness were used as the plate made of Teflon® and the quartz glass plate. The quartz glass plate 10a is adjusted to a clean and dry by wiping off the surface with "Kimwipe" every measurement. In the measurement, three samples S were attached to a friction block 20 of a measurement jig 11 (weight of 62 g=W) shown in FIG. 2 and FIG. 3. At this time, the sample S were placed on tip of a mount holder 21 of the friction block 20, and then pressed by a packing 22 and fixed by a nut 23. In a state where the sample S is fixed while protruding from the end portion of the friction block 20, a borate buffer (each 0.1 mL) was dropped on each center portion of three samples under the following condition A, while a saline (each 0.1 mL) was dropped under the following condition B. Thereafter, the measurement jig 11 was quickly attached to the apparatus 1 and then stress (F) in a horizontal direction when the sample stand 10 is moved to a horizontal direction (arrow Y) at a rate of 1.0 mm/second in a state where all three samples are contacted with the quartz glass plate 10a is detected by a friction detection unit 12 and measured by a dynamometer 13. The surface friction coefficient (MIU) was determined by the following equation.

$$MIU=F/W$$

A move distance was set at 30 mm and the measurement of MIU was carried out every 0.1 second.

The surface friction coefficient was an average value (value obtained by dividing the total of MIU in each time within a section by the number of data of MIU) of MIU in the section (at least 5 mm) where MIU at a move distance of 5 to 25 mm became stable. At this time, a surface friction coefficient under the conditions A was MIUa, while a surface friction coefficient under the conditions B was MIUb.
Condition A: The measurement was carried out using samples in a state of being wetted with a borate buffer.
Condition B: The measurement was carried out using samples in a state of being wetted with a saline.

In FIG. 3, a thickness of a supporting plate which supports the friction block 20 of the measurement jig 11 is set at d1. In the friction block 20, when a protrusion length from the measurement jig 11 is d2, a diameter of the portion contacted with a lens of a mount holder 21 is d3, and a diameter of a periphery of a nut 23 is d4, d1=1.5 (mm), d2=22.4 (mm), d3=14 (mm), and d4=(mm).
(13) Surface Friction Coefficient Ratio Surface friction coefficient (MIUo) of "ACUVUE® OASYS" (Johnson & Johnson Company) was measured by the method mentioned in (12) was measured under condition A. Surface friction coefficient ratios Qa and Qb were determined by the following equations.

$$Qa=MIUa/MIUo$$

$$Qb=MIUb/MIUo$$

(14) Boiling Resistance

Samples immersed in clean borate buffer were put in a closed vial bottle. Autoclave sterilization was carried out at 121° C. for 30 minutes, and then samples were cooled to room temperature. Five cycles were repeated, one cycle including a series of the above operations. Thereafter, the above-mentioned water wettability was evaluated.
(15) Scrubbing Resistance A. Samples (with contact lens shape) in a state of being wetted with a borate buffer were placed in the recess formed in the center of the flat of the hand and a cleaning solution ("OPTI FREE®", ALCON JAPAN LTD.) was added. After scrubbing front and back sides (each 10 times) by ball of the forefinger of another hand, samples were put in a screw tube containing clean "OPTI FREE®" and then left to stand for 4 hours or more. Fifteen cycles were repeated, provided that one cycle includes a series of the above operations. Samples were then washed with pure water and immersed in a borate buffer. Thereafter, the above-mentioned water wettability was evaluated.

B. Samples (with contact lens shape) in a state of being wetted with a borate buffer were placed in the recess formed in the center of the flat of the hand and a cleaning solution ("ReNU®", Bausch & Lomb Incorporated) was added. After scrubbing front and back sides (each 10 times) by ball of the forefinger of another hand, samples were grasped by the thumb and forefinger and then both sides were further scrubbed 20 times while sprinkling the cleaning solution on the samples. The samples thus scrubbed were immersed in a borate buffer. Thereafter, the above-mentioned lubricity was evaluated. If there is a need to distinguish from other evaluation methods, this evaluation method was written as "scrubbing resistance-RN".

(16) Comfort

Two subjects wore contact lens-shaped samples in a state of being wetted with a borate buffer for 6 hours. The evaluation was carried out according to the following criteria. Feeling of foreign matter (so-called sandy feeling) associated with drying was also included in feeling of dryness.
A: Both two subjects did not feel dry
B: Only one subject felt dry
C: Both two subjects felt dry
D: Wearing was stopped since one subject felt dry or felt strongly sticky to eyes
E: Wearing was stopped since two subjects felt dry or felt strongly sticky to eyes

(17) Oxygen Permeability

Two film-shaped samples (measuring 20 mm×20 mm×0.1 mm) laid one upon another, or a film-shaped sample (measuring 20 mm×20 mm×0.2 mm) were/was used for the measurement. Using an oxygen permeability measuring device, model OX-TRAN2/21 (Hitachi High-Technologies Corporation), oxygen permeability was measured. A mixed gas of nitrogen (98%)/hydrogen (2%) was used as a carrier gas, and a mixed gas of nitrogen (79.3%)/oxygen (20.7%) was used as a measuring gas. Humidification of the gas was not carried out.

(18) Quartz Crystal Microbalance (QCM)

Using a quartz crystal resonator biosensing system QCM934 (SEIKO EG&G CO., LTD.) and a QCM measurement software WinQCM (Ver1.05, SEIKO EG&G CO., LTD.), the measurement was carried out. QA-A9M-AU (E) (SEIKO EG&G CO., LTD.) was used as a quartz resonator sensor.

QA-A9M-AU (E) Specification
Resonance frequency: 9 MHz
Cut type: AT-cut
Electrode material: Gold
Electrode thickness: formed by sputtering an electrode material (about 300 nm) on base titanium (about 100 nm)
Electrode diameter: 5 mmφ
Shape: Square type measuring 7.9 mm×7.9 mm Using QCM, the measurement was carried out at room temperature (about 25° C.) and a fundamental frequency of 27 MHz (input value to QCM measurement software is 26.95 MHz).

(19) Comfort

Two subjects wore contact lens-shaped samples in a state of being wetted with a borate buffer for 6 hours. The evaluation was carried out according to the following criteria. Feeling of foreign matter (so-called sandy feeling) associated with drying was also included in feeling of dryness.
A: Both two subjects did not feel dry
B: Only one subject felt dry
C: Both two subjects felt dry
D: Wearing was stopped since one subject felt dry or felt strongly sticky to eyes
E: Wearing was stopped since two subjects felt dry or felt strongly sticky to eyes

(20) Lacrimal Fluid Dynamics

One subject wore contact lenses. Using a Flores test paper (manufactured by SHOWA YAKUHIN KAKO CO., LTD.), a lacrimal fluid was cooled, and then an operation of lightly pressing a surface of the contact lens worn using a dry cotton swab while observing with a slit lamp SL-203 type (manufacturer Co. Ohira) was slowly repeated several times. In this case, the case where lacrimal fluid exchange (flow of lacrimal fluid) due to a lacrimal fluid exchange-promoting pattern could be reconfirmed was rated "A", whereas, the case where lacrimal fluid exchange (flow of lacrimal fluid) due to a lacrimal fluid exchange-promoting pattern cannot be reconfirmed was rated "B". It is considered that a lacrimal fluid is exchanged by receiving a pressure from the eyelid during wear if rated as "A".

Reference Example 1

Preparation of Acid Type UniBlue A

In a 50 mL screw bottle, 20 g of pure water was charged. UniBlue A (product number 298409, Sigma-Aldrich Corporation) (0.5 g) was added and dissolved in an incubator at 37° C. After dissolution, 4 g of 1N hydrochloric acid was added and the pH of about 1 to 2 was confirmed by a pH indicator paper. Ethyl acetate (24 g) was added, followed by slight stirring. The mixture was transferred to a 100 mL recovery flask and left to stand. Since UniBlue A transfers to an ethyl acetate side, the aqueous layer as the lower layer was discarded. The ethyl acetate layer was transferred to a 100 mL recovery flask and then vaporized in an evaporator at 20° C., followed by drying in a vacuum dryer at 40° C. for 16 hours to obtain an acid type UniBlue A [estimated structural formula (M1)].

[Chemical Formula 6]

(M1)

Reference Example 2

Preparation of Base Material A and Base Material $A_F$

Polydimethylsiloxane having a methacryloyl group at both ends (FM7726, JNC, a compound of the formula (M2), mass average molecular weight of 29 kD, number average molecular weight of 26 kD) (48 parts by mass) as a component A, trifluoroethyl acrylate (Viscoat 3F, Osaka Organic Chemical Industry Ltd.) (45 parts by mass) as a component B, polydimethylsiloxane having a methacryloyl group at one end (FM0725, JNC, a compound of the formula (M3), mass average molecular weight of 13.3 kD, number average molecular weight of 12.8 kD) (2 parts by mass) as a component C, 2-ethylhexyl acrylate (3 parts by mass) as a component C, dimethylaminoethyl acrylate (1 part by mass) as a component C, an ultraviolet absorber having a polymerizable group (RUVA-93, Otsuka Chemical Co., Ltd.) (1 part by mass) as a component C, an acid type UniBlue A (Reference Example 1) (0.04 part by mass) as a component C, a polymerization initiator "IRGACURE®" 819 (Ciba Specialty Chemicals Inc., 0.75 part by mass), and t-amyl alcohol (5 parts by mass) were mixed and then stirred. This mixture was filtered through a membrane filter (0.45 µm) to remove an insoluble matter, thus obtaining a monomer mixture. This monomer mixture was charged in a test tube and degassing was carried out under reduced pressure of 20 Torr (27 hPa) while stirring using a touch mixer, and then the pressure was returned to atmospheric pressure using an argon gas. This operation was repeated three times. In a glove box under a nitrogen atmosphere, the monomer mixture was injected into a mold for contact lens made of a transparent resin (polypropylene on a base curve side, Zeonor on a front curve side) and then polymerized by irradiating with light (1.71 mW/cm$^2$, 20 minutes) using a fluorescent lamp (Toshiba Corporation, FL-6D, quasi-daylight, 6 W, 4 lamps). After polymerization, the whole mold was immersed in isopropyl alcohol and a contact lens-shaped molding was removed from the mold. The obtained molding was immersed in a large excess amount of isopropyl alcohol at 60° C. for 2 hours. Furthermore, the obtained molding was immersed in clean isopropyl alcohol at room temperature for 1 minute, and then the molding was taken out and air-dried at room temperature for 12 hours or more. This molding was regarded as a base material A. The base material A includes an edge portion having a diameter of about 13 mm and a center portion having a thickness of about 0.07 mm. Using two glass plates and a gasket as a mold, a film-shaped sample measuring 30 mm×30 mm×0.1 mm was obtained by performing the same operation. This film-shaped sample was regarded as a base material $A_F$.

[Chemical Formula 7]

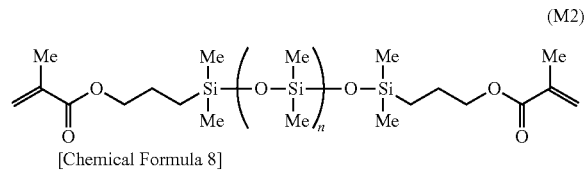

(M2)

[Chemical Formula 8]

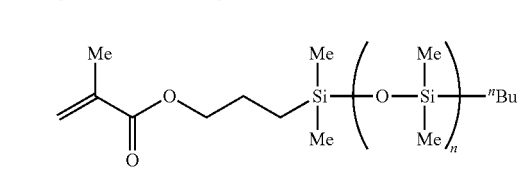

(M3)

Reference Example 3

Preparation of Base Material B

Polydimethylsiloxane having a methacryloyl group at both ends, (FM7726, JNC, a compound of the formula (M2), mass average molecular weight of 29 kD, number average molecular weight of 26 kD) (48 parts by mass) as a component A, trifluoroethyl acrylate (Viscoat 3F, Osaka Organic Chemical Industry Ltd.) (48.5 parts by mass) as a component B, methyl (meth)acrylate (0.5 part by mass) as a component C, an ultraviolet absorber having a polymerizable group (RUVA-93, Otsuka Chemical Co., Ltd.) (1 part by mass) as a component C, a polymerization initiator "IRGACURE®" 819 (Ciba Specialty Chemicals Inc., 0.75 part by mass), and t-amyl alcohol (5 parts by mass) were mixed and then stirred. Thereafter, the same operation as in Reference Example 2 was carried out to produce a lens. This lens was regarded as a base material B. The base material B includes an edge portion having a diameter of about 13 mm and a center portion having a thickness of about 0.07 mm.

Reference Example 4

Preparation of Base Material C

A silicone monomer represented by the formula (M4) (13.4 parts by mass), N,N-dimethylacrylamide (37.0 parts by mass), a silicone monomer represented by the formula (M5) (36.6 parts by mass), a photoinitiator IRGACURE 1850 (1.26 parts by mass), an ultraviolet absorber (RUVA-93, Otsuka Chemical Co., Ltd.) (1.26 parts by mass), 2-hydroxyethyl methacrylate (9.2 parts by mass), triethylene glycol dimethacrylate (1.26 parts by mass), UniBlue A (product number 298409, Sigma-Aldrich Corporation, a structure of the formula (M6), 0.02 part by mass), and tetrahydrolinalool (23.9 parts by mass) were mixed and then stirred. This mixture was filtered through a membrane filter (0.45 µm) to remove an insoluble matter, thus obtaining a monomer mixture. This monomer mixture was charged in a test tube and degassing was carried out under reduced pressure of 20 Torr (27 hPa) while stirring using a touch mixer, and then the pressure was returned to atmospheric pressure using an argon gas. This operation was repeated three times. In a glove box under a nitrogen atmosphere, the monomer mixture was injected into a mold for contact lens made of a transparent resin (polypropylene on a base curve side, Zeonor on a front curve side) and then polymerized by irradiating with light (1.71 mW/cm$^2$, 20 minutes) using a fluorescent lamp (Toshiba Corporation, FL-6D, quasi-daylight, 6 W, 4 lamps). After polymerization, the whole mold was immersed in an aqueous 60% by mass isopropyl alcohol solution and a contact lens-shaped molding was removed from the mold. The obtained molding was immersed in a large excess amount of an aqueous 80% by mass isopropyl alcohol solution at 60° C. for 2 hours. Furthermore, the obtained molding was immersed in a large excess amount of an aqueous 50% by mass isopropyl alcohol solution at room temperature for 30 minutes, followed by immersion in a large excess amount of an aqueous 25% by mass isopropyl alcohol solution at room temperature for 30 minutes and further immersion in a large excess amount of pure water at room temperature for 30 minutes. This molding was regarded as a base material C. The base material C includes an edge portion having a diameter of about 14 mm and a center portion having a thickness of about 0.07 mm.

[Chemical Formula 9]

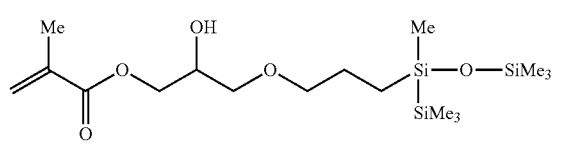

(M4)

[Chemical Formula 10]

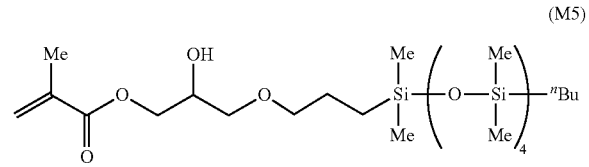

(M5)

[Chemical Formula 11]

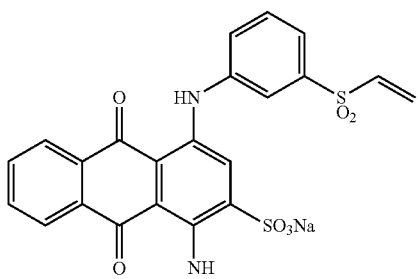

(M6)

(Synthesis of Polymer for Coating)

Synthesis Examples of copolymers used for coating in Examples are shown. In Synthesis Examples, molecular weight of each copolymer was measured under the following conditions to thereby determine polyethylene oxide-equivalent molecular weight.
Apparatus: Prominence GPC system, manufactured by Shimadzu Corporation
Pump: LC-20AD
Auto-sampler: SIL-20AHT
Column oven: CTO-20A
Detector: RID-10A
Column: manufactured by TOSOH CORPORATION GMP-WXL (7.8 mm in inner diameter×30 cm, 13 μm in particle diameter)
Solvent: water/methanol=1/1 (addition of 0.1N lithium nitrate)
Flow rate: 0.5 mL/minute
Measurement time: 30 minutes
Sample concentration: 0.1% by mass
Injection amount: 100 μL
Standard sample: Polyethylene oxide standard sample, manufactured by Agilent (0.1 kD to 1,258 kD)

Synthesis Example 1

<CPVPA: N-Vinylpyrrolidone/Acrylic Acid (Molar Ratio of 9/1)>

In a 500 mL three-necked flask, N-vinylpyrrolidone (NVP, 90.02 g, 0.81 mol), acrylic acid (6.49 g, 0.09 mol), dimethyl sulfoxide (386.8 g), and a polymerization initiator VA-061 (Wako Pure Chemical Industries, Ltd., 0.1408 g, 0.562 mmol), 2-mercaptoethanol (2-ME, 43.8 μL, 0.63 mmol) were charged, and equipped with a three-way stop-cock, a reflux condenser tube, a thermometer, and a mechanical stirrer. The concentration of the monomer was 20% by mass. After degassing inside the three-necked flask using a vacuum pump and repeating replacement by argon three times, stirring was carried out at 50° C. for 0.5 hour, followed by temperature rise to 70° C. and further stirring for 6.5 hours. After completion of the polymerization, the polymerization reaction solution was cooled to room temperature and 100 mL of water was added, and then the solution was poured into 500 mL of acetone and the mixed solution was left to stand overnight. Then, 200 mL of acetone and 100 mL of hexane were further added and the supernatant was removed by decantation. The obtained solid component was washed seven times with acetone/water (=500 mL/100 mL). The solid component was dried overnight by a vacuum drying oven at 60° C. Liquid nitrogen was charged and the solid component was crushed by a spatula, and then dried by a vacuum drying oven at 60° C. for 3 hours. The thus obtained copolymer had a molecular weight of Mn: 35 kD, Mw: 130 kD (Mw/Mn=3.8).

Synthesis Example 2

<CPDA: N,N-Dimethylacrylamide/Acrylic Acid (Molar Ratio of 2/1)>

In a 500 mL three-necked flask, N,N-dimethylacrylamide (59.50 g, 0.600 mol), acrylic acid (21.62 g, 0.300 mol), pure water (325.20 g), a polymerization initiator VA-061 (Wako Pure Chemical Industries, Ltd., 0.1408 g, 0.562 mmol), and 2-mercaptoethanol (43.8 μL, 0.63 mmol) were charged, and then equipped with a three-way stop-cock, a reflux condenser tube, a thermometer, and a mechanical stirrer. The concentration of the monomer was 20% by mass. After degassing inside the three-necked flask using a vacuum pump and repeating replacement by argon three times, stirring was carried out at 50° C. for 0.5 hour, followed by temperature rise to 70° C. and further stirring for 6.5 hours. After completion of the polymerization, the polymerization reaction solution was concentrated to 400 g by an evaporator and poured into a 2-propanol/n-hexane (=500 mL/500 mL). The mixed solution was left to stand, and then the supernatant was removed by decantation. The obtained solid component was washed three times with 2-propanol/n-hexane (=250 mL/250 mL). The solid component was dried overnight by a vacuum drying oven at 60° C. Liquid nitrogen was charged and the solid component was crushed by a spatula, and then dried by a vacuum drying oven at 60° C. for 3 hours. The thus obtained copolymer had a molecular weight of Mn: 55 kD, Mw: 192 kD (Mw/Mn=3.5).

Synthesis Example 3

<CPHA: 2-Hydroxyethyl Methacrylate/Acrylic Acid (Molar Ratio of 3/1)>

In a 300 mL three-necked flask, 2-hydroxyethyl methacrylate (HEMA, 10.3 g, 0.09 mol), acrylic acid (AA, 2.2 g, 0.03 mol), dimethyl sulfoxide (49.8 g), a polymerization initiator VA-061 (Wako Pure Chemical Industries, Ltd., 0.009 g, 0.038 mmol), and 2-mercaptoethanol (2-ME, 7.8 μL, 0.111 mmol) were charged, and then equipped with a three-way stop-cock, a reflux condenser tube, a thermometer, and a mechanical stirrer. The concentration of the monomer was 20% by mass. After degassing inside the three-necked flask using a vacuum pump and repeating replacement by argon three times, stirring was carried out at 60° C. for 0.5 hour, followed by temperature rise to 70° C. and further stirring for 4.5 hours. After completion of the polymerization, the polymerization reaction solution was cooled to room temperature and 20 mL of ethanol was added, and then the solution was poured into 500 mL of water and the mixed solution was left to stand overnight. Then, the supernatant was discarded and the obtained solid component was washed twice with 500 mL of water. The solid component was dried overnight by a vacuum drying oven at 60° C. Liquid nitrogen was charged and the solid component was crushed by a spatula, and then dried by a vacuum drying oven at 60° C. for 3 hours. The thus obtained copolymer had a molecular weight of Mn: 50 kD, Mw: 96 kD (Mw/Mn=1.9).

Reference Example 5

Preparation of Coating Solution

Hereinafter, pure water means water purified by filtering through a reverse osmosis membrane.

<PEI Solution>

Polyethyleneimine (P3143, Sigma-Aldrich Corporation, molecular weight of 750,000) was dissolved in pure water to obtain an aqueous 1.1% by mass solution.

<PAA Solution>

Polyacrylic acid (169-18591, Wako Pure Chemical Industries, Ltd., molecular weight 250,000) was dissolved in pure water to obtain an aqueous 1.2% by mass solution.

<CPVPA Solution>

CPVPA obtained in Synthesis Example 1 was dissolved in pure water to obtain an aqueous 1.1% by mass solution.

<CPDA Solution>

CPDA obtained in Synthesis Example 2 was dissolved in pure water to obtain an aqueous 1.1% by mass solution.

<CPHA Solution>

CPHA obtained in Synthesis Example 3 was dissolved in pure water to obtain an aqueous 0.01% by mass solution.

<PAA1 Solution>

An aqueous polyacrylic acid solution (Sigma-Aldrich Corporation, catalog number 52392-5, molecular weight of 100,000) was diluted with pure water to thereby control to 0.001M, and then 1M hydrochloric acid was added to thereby adjust the pH to about 2.5. The concentration of polyacrylic acid was calculated based on a repeating unit (acrylic acid).

<PAA2 Solution>

An aqueous polyacrylic acid solution (Sigma-Aldrich Corporation, catalog number 52392-5, molecular weight of 100,000) was diluted with pure water to thereby control to 0.0001M, and then 1M hydrochloric acid was added to thereby adjust the pH to about 2.5. The concentration of polyacrylic acid was calculated based on a repeating unit (acrylic acid).

<PAH1 Solution>

Poly(allylamine hydrochloride) (Sigma-Aldrich Corporation, catalog number 28322-3, molecular weight of 56,000) was dissolved in pure water to thereby control to 0.0001M, and then 1M hydrochloric acid was added to thereby adjust the pH to about 2.5. The concentration of poly(allylamine hydrochloride) was calculated based on a repeating unit (allylamine hydrochloride).

<CPDA1 Solution>

A CPDA solution was diluted with pure water to give a 0.01M solution, and then 1M hydrochloric acid was added to thereby adjust the pH to about 2.5. The concentration of CPDA was calculated based on mol average molecular weight of a repeating unit.

<CPDA2 Solution>

A CPDA solution was diluted with pure water to thereby control to 0.0001M, and then 1M hydrochloric acid was added to thereby adjust the pH to about 2.5. The concentration of CPDA was calculated based on mol average molecular weight of a repeating <AcOH>

Glacial acetic acid was dissolved in pure water to obtain an aqueous 1.1% by mass solution.

<P(DMAA/AA) Solution>

CPDA obtained in Synthesis Example 2 was dissolved in pure water to obtain an aqueous 1% by mass solution.

Example 1

The base material A (Reference Example 2) was immersed in a first solution (PAA solution) for 30 minutes and then respectively immersed in three pure water baths for 5 minutes. Next, the base material was immersed in a second solution (PEI solution) for 30 minutes and then respectively immersed in three pure water baths for 5 minutes. Next, the base material was immersed in a third solution (PAA solution) for 30 minutes and then respectively immersed in three pure water baths for 5 minutes. The coated base material A was put in a glass bottle filled with a borate buffer, followed by sealing. After subjecting to an autoclave treatment (at 121° C. for 30 minutes), a low water content soft contact lens was obtained. The evaluation results of the obtained low water content soft contact lens are shown in Table 1.

TABLE 1

| | Example 1 | Example 2 | Example 3 | Example 4 | Example 5 | Example 6 | Example 7 | Example 8 | Example 9 |
|---|---|---|---|---|---|---|---|---|---|
| Base material | Base material A | Base material A | Base material A | Base material A | Base material B | Base material B | Base material B | Base material B | Base material A |
| First solution | PAA solution | PAA solution | PAA solution | PAA solution | PAA solution | PAA solution | PAA solution | PAA solution | CPDA1 solution |
| Second solution | PEI solution | PEI solution | PEI solution | PEI solution | PEI solution | PEI solution | PEI solution | PEI solution | PAH1 solution |
| Third solution | PAA solution | CPDA solution | CPVPA solution | CPHA solution | PAA solution | CPDA solution | CPVPA solution | CPHA solution | CPDA2 solution |
| Fourth solution | — | — | — | — | — | — | — | — | PAH1 solution |
| Fifth solution | — | — | — | — | — | — | — | — | CPDA2 solution |
| Sixth solution | — | — | — | — | — | — | — | — | PAH1 solution |
| Seventh solution | — | — | — | — | — | — | — | — | CPDA2 solution |
| Eighth solution | — | — | — | — | — | — | — | — | PAH1 solution |
| Ninth solution | — | — | — | — | — | — | — | — | CPDA2 solution |
| Transparency | A | A | A | A | A | A | A | A | A |
| Water content (%) | <1 | <1 | <1 | <1 | <1 | <1 | <1 | <1 | <1 |
| Water wettability | B | A | B | — | — | — | — | — | — |
| Dynamic contact angle (Advancing angle) | 31 | 29 | 54 | 77 | 33 | 32 | 45 | 79 | 56 |
| Tensile elastic modulus (kPa) | 728 | 745 | 771 | 799 | 837 | 861 | 880 | 785 | 758 |
| Tensile elongation (%) | 529 | 545 | 379 | 426 | 595 | 632 | 532 | 550 | 520 |

TABLE 1-continued

|  | Example 1 | Example 2 | Example 3 | Example 4 | Example 5 | Example 6 | Example 7 | Example 8 | Example 9 |
|---|---|---|---|---|---|---|---|---|---|
| Lubricity | — | A | — | — | — | — | — | — | — |
| Adhesion of mucin | — | 2.0 | — | — | — | — | — | — | — |
| Adhesion of lipid | — | B | — | — | — | — | — | — | — |
| Artificial lacrimal fluid immersion test | — | C | — | — | — | — | — | — | — |
| Degree of pigmentation | A | A | A | A | E | E | E | E | A |
| Surface friction coefficient (MIUa) | 0.023 | 0.010 | 0.152 | 0.101 | 0.010 | 0.015 | 0.032 | 0.269 | 0.192 |
| Surface friction coefficient (MIUb) | 0.038 | 0.005 | 0.069 | 0.069 | 0.083 | 0.060 | 0.353 | 1.609 | 0.715 |
| Surface friction coefficient ratio (Qa) | 0.075 | 0.033 | 0.498 | 0.498 | 0.033 | 0.050 | 0.104 | 0.883 | 0.629 |
| Surface friction coefficient ratio (Qb) | 0.124 | 0.018 | 0.227 | 0.227 | 0.273 | 0.197 | 1.158 | 5.275 | 2.344 |
| Qb − Qa | 0.048 | −0.015 | −0.272 | −0.272 | 0.240 | 0.146 | 1.054 | 4.392 | 1.715 |
| Boiling resistance | — | A | — | — | — | — | — | — | — |
| Scrubbing resistance | — | A | — | — | — | — | — | — | — |
| Comfort | — | A | — | — | — | — | — | — | — |
| Oxygen permeability $[10^{-11}$ (cm$^2$/sec) (mL · hPa)] | — | — | — | — | — | — | — | — | — |

Examples 2 to 8

The base materials shown in Table 1 were immersed in a first solution (PAA solution) shown in Table 1 for 30 minutes, and then respectively immersed in three pure water baths for 5 minutes. Next, the base materials were immersed in a second solution (PEI solution) shown in Table 1 for 30 minutes, and then respectively immersed in three pure water baths for 5 minutes. Next, the base materials were immersed in a third solution shown in Table 1 for 30 minutes, and then respectively immersed in three pure water baths for 5 minutes. The coated base materials were put in a glass bottle filled with a borate buffer, followed by sealing. After subjecting to an autoclave treatment (at 121° C. for 30 minutes), low water content soft contact lenses were obtained. The evaluation results of the obtained low water content soft contact lenses are shown in Table 1. The third solution is selected from among the above-mentioned PAA solution, CPVPA solution, CPDA solution, and CPHA solution.

Example 9

The base material A (Reference Example 2) was subjected to coating E disclosed in Example 4 of Kohyo (National Publication of Translated Version) No. 2005-538418. Coating E means that coating is carried out in the order of PAA/PAH/PAA/PAH/PAA/PAH/PAA/PAH/PAA when polyacrylic acid is written as PAA and poly(allylamine hydrochloride) is written as PAH. In place of the PAA solution (PAA1 solution, 0.01M, pH 2.5), a CPDA1 solution (0.01M, pH 2.5) and a CPDA2 solution (0.0001M, pH 2.5) were used. Namely, coating was carried out in the order of CPDA/PAH/CPDA/PAH/CPDA/PAH/CPDA/PAH/CPDA. Specifically, (a) the base material A is immersed in a CPDA1 solution (0.01M, pH 2.5) for 30 minutes to form an innermost layer. Then, (b) the base material A is immersed in a PAH1 solution (0.0001M, pH 2.5) for 5 minutes without subjecting to rinsing. Furthermore, (c) the obtained base material A is immersed in a CPDA2 solution (0.0001M, pH 2.5) for 5 minutes without subjecting to rinsing. (d) The obtained base material A is further repeatedly subjected to the steps (b) and (c) three times to obtain a base material A coated by coating E. The base material A coated by coating E is put in a glass bottle filled with a borate buffer. After sealing, an autoclave treatment (121° C., 30 minutes) was carried out to obtain a low water content soft contact lens. The evaluation results of the obtained low water content soft contact lens are shown in Table 1.

Example 10

The base material B (Reference Example 3) was subjected to coating E disclosed in Example 4 of Kohyo (National Publication of Translated Version) No. 2005-538418. In place of the PAA solution (PAA1 solution, 0.01M, pH 2.5), a CPDA1 solution (0.01M, pH 2.5) and a CPDA2 solution (0.0001M, pH 2.5) were used. Namely, coating was carried out in the order of CPDA/PAH/CPDA/PAH/CPDA/PAH/CPDA/PAH/CPDA. Specifically, (a) the base material A is immersed in a CPDA1 solution (0.01M, pH 2.5) for 30 minutes to form an innermost layer. Then, (b) the base material A is immersed in a PAH1 solution (0.0001M, pH 2.5) for 5 minutes without subjecting to rinsing. Furthermore, (c) the obtained base material A is immersed in a CPDA2 solution (0.0001M, pH 2.5) for 5 minutes without subjecting to rinsing. (d) The obtained base material A is further repeatedly subjected to the steps (b) and (c) three times to obtain a base material A coated by coating E. The base material A coated by coating E is put in a glass bottle filled with a borate buffer. After sealing, an autoclave treatment (121° C., 30 minutes) was carried out to obtain a low water content soft contact lens. The evaluation results of the obtained low water content soft contact lens are shown in Table 2.

TABLE 2

| | Example 10 | Example 11 | Comparative Example 1 | Comparative Example 2 | Reference Example 12 | Comparative Example 3 | Comparative Example 4 |
|---|---|---|---|---|---|---|---|
| Base material | Base material B | Base material $A_F$ | Base material A | Base material A | Base material A | Base material A | Base material A |
| First solution | CPDA1 solution | PAA solution | PAA2 solution | PAA2 solution | CPA2 solution | PAA1 solution | PAA1 solution |
| Second solution | PAH1 solution | PEI solution | PAH1 solution | PAH1 solution | PAH1 solution | PAH1 solution | PAH1 solution |
| Third solution | CPDA2 solution | CPDA solution | PAA2 solution | PAA2 solution | CPDA2 solution | PAA2 solution | PAA2 solution |
| Fourth solution | PAH1 solution | — | PAH1 solution | PAH1 solution | PAH1 solution | PAH1 solution | PAH1 solution |
| Fifth solution | CPDA2 solution | — | PAA2 solution | PAA2 solution | CPDA2 solution | PAA2 solution | PAA2 solution |
| Sixth solution | PAH1 solution | — | PAH1 solution | PAH1 solution | PAH1 solution | PAH1 solution | PAH1 solution |
| Seventh solution | CPDA2 solution | — | PAA2 solution | PAA2 solution | CPDA2 solution | PAA2 solution | PAA2 solution |
| Eighth solution | PAH1 solution | — | PAH1 solution | PAH1 solution | PAH1 solution | PAH1 solution | PAH1 solution |
| Ninth solution | CPDA2 solution | — | PAA2 solution | CPDA2 solution | CPDA2 solution | PAA2 solution | CPDA2 solution |
| Transparency | A | A | A | A | A | A | A |
| Water content (%) | <1 | <1 | <1 | <1 | <1 | <1 | <1 |
| Water wettability | — | A | E | — | — | — | — |
| Dynamic contact angle (Advancing angle) | — | 30 | 93 | 99 | — | 83 | 98 |
| Tensile elastic modulus (kPa) | — | 738 | 758 | 745 | 772 | 772 | 786 |
| Tensile elongation (%) | — | 480 | 512 | 525 | 495 | 513 | 542 |
| Lubricity | — | A | D | — | — | — | — |
| Adhesion of mucin | — | — | 3.9 | — | — | — | — |
| Adhesion of lipid | — | B | D | — | — | — | — |
| Artificial lacrimal fluid immersion test | — | C | E | — | — | — | — |
| Degree of pigmentation | E | A | A | A | A | A | A |
| Surface friction coefficient (MIUa) | — | 0.010 | 0.574 | 1.742 | — | 1.224 | 0.452 |
| Surface friction coefficient (MIUb) | — | 0.007 | 1.643 | — | — | — | — |
| Surface friction coefficient ratio (Qa) | — | 0.033 | 1.882 | 5.710 | — | 4.014 | 1.483 |
| Surface friction coefficient ratio (Qb) | — | 0.023 | 5.388 | — | — | — | — |
| Qb − Qa | — | −0.010 | 3.505 | — | — | — | — |
| Boiling resistance | — | A | E | — | — | — | — |
| Scrubbing resistance | — | A | E | — | — | — | — |
| Comfort | — | — | E | — | — | — | — |
| Oxygen permeability $[10^{-11} (cm^2/sec)(mL \cdot hPa)]$ | — | 375 | — | — | — | — | — |

Example 11

The base material $A_F$ (Reference Example 2) was immersed in a first solution (PAA solution) for 30 minutes, and then respectively immersed in three pure water baths for 5 minutes. Next, the base material was immersed in a second solution (PEI solution) for 30 minutes, and then respectively immersed in three pure water baths for 5 minutes. Next, the base material was immersed in a third solution (CPDA solution) for 30 minutes, and then respectively immersed in three pure water baths for 5 minutes. The coated base materials were put in a glass bottle filled with a borate buffer, followed by sealing. After subjecting to an autoclave treatment (at 121° C. for 30 minutes), a medical device was obtained. The evaluation results of the medical device are shown in Table 2.

Comparative Example 1

The base material A (Reference Example 2) was subjected to coating C disclosed in Example 4 of Kohyo (National Publication of Translated Version) No. 2005-538418. Coating C means that coating is carried out in the order of PAA/PAH/PAA/PAH/PAA/PAH/PAA/PAH/PAA when polyacrylic acid is written as PAA and poly(allylamine hydrochloride) is written as PAH. Specifically, (a) the base material A is immersed in a PAA2 solution (0.0001M, pH 2.5) for 30 minutes to form an innermost layer. Then, (b) the obtained base material A is immersed in a PAH1 solution (0.0001M, pH 2.5) for 5 minutes without subjecting to rinsing. Furthermore, (c) the obtained base material A is immersed in a PAA2 solution (0.0001M, pH 2.5) for 5 minutes without subjecting to rinsing. (d) The obtained base material A is further repeatedly subjected to the steps (b) and (c) three times to obtain a base material A coated by coating C. The base material A coated by coating C is put in a glass bottle filled with a borate buffer. After sealing, an autoclave treatment (121° C., 30 minutes) was carried out to obtain a low water content soft contact lens. The evaluation results of the obtained low water content soft contact lens are shown in Table 2.

Comparative Example 2

In the same manner as in Comparative Example 1, the base material A (Reference Example 2) was subjected to coating C disclosed in Example 4 of Kohyo (National Publication of Translated Version) No. 2005-538418. In the coating of a final layer, a CPDA2 solution (0.0001M, pH 2.5) was used in place of a PAA2 solution (0.0001M, pH 2.5). Namely, coating was carried out in the order of PAA/PAH/PAA/PAH/PAA/PAH/PAA/PAH/CPDA. The obtained base material was put in a glass bottle filled with a borate buffer. After sealing, an autoclave treatment (at 121° C. for 30 minutes) was carried out to obtain a low water content soft contact lens. The evaluation results of the obtained low water content soft contact lens are shown in Table 2.

Reference Example 12

In the same manner as in Comparative Example 1, the base material A (Reference Example 2) was subjected to coating C disclosed in Example 4 of Kohyo (National Publication of Translated Version) No. 2005-538418. In place of the PAA2 solution (0.0001M, pH 2.5), a CPDA2 solution (0.0001M, pH 2.5) was used. Namely, coating was carried out in the order of CPDA/PAH/CPDA/PAH/CPDA/PAH/CPDA/PAH/CPDA. The obtained base material was put in a glass bottle filled with a borate buffer. After sealing, an autoclave treatment (at 121° C. for 30 minutes) was carried out to obtain a low water content soft contact lens. The evaluation results of the obtained low water content soft contact lens are shown in Table 2.

Comparative Example 3

The base material A (Reference Example 2) was subjected to coating E disclosed in Example 4 of Kohyo (National Publication of Translated Version) No. 2005-538418. Coating E means that coating is carried out in the order of PAA/PAH/PAA/PAH/PAA/PAH/PAA/PAH/PAA when polyacrylic acid is written as PAA and poly(allylamine hydrochloride) is written as PAH. Specifically, (a) the base material A is immersed in a PAA1 solution (0.01M, pH 2.5) for 30 minutes to form an innermost layer. Then, (b) the obtained base material A is immersed in a PAH1 solution (0.0001M, pH 2.5) for 5 minutes without subjecting to rinsing. Furthermore, (c) the obtained base material A is immersed in a PAA2 solution (0.0001M, pH 2.5) for 5 minutes without subjecting to rinsing. (d) The obtained base material A is further repeatedly subjected to the steps (b) and (c) three times to obtain a base material A coated by coating E. This base material A coated by coating E was put in a glass bottle filled with a borate buffer. After sealing, an autoclave treatment (at 121° C. for 30 minutes) was carried out to obtain a low water content soft contact lens. The evaluation results of the obtained low water content soft contact lens are shown in Table 2.

Comparative Example 4

In the same manner as in Reference Example 12, the base material A (Reference Example 2) was subjected to coating E disclosed in Example 4 of Kohyo (National Publication of Translated Version) No. 2005-538418. In the coating of a final layer, a CPDA2 solution (0.0001M, pH 2.5) was used in place of the PAA2 solution (0.0001M, pH 2.5). Namely, coating was carried out in the order of PAA/PAH/PAA/PAH/PAA/PAH/PAA/PAH/CPDA. The obtained base material was put in a glass bottle filled with a borate buffer. After sealing, an autoclave treatment (at 121° C. for 30 minutes) was carried out to obtain a low water content soft contact lens. The evaluation results of the obtained low water content soft contact lens are shown in Table 2.

TABLE 3

|  | Comparative Example 5 | Comparative Example 6 | Comparative Example 7 | Comparative Example 8 |
|---|---|---|---|---|
| Base material | Commercially available product | Base material C | Base material C | Base material $A_F$ |
| First solution | — | PAA solution | PAA1 solution | PAA2 solution |
| Second solution | — | PEI solution | PAH1 solution | PAH1 solution |
| Third solution | — | CPDA solution | PAA2 solution | PAA2 solution |
| Fourth solution | — | — | PAH1 solution | PAH1 solution |
| Fifth solution | — | — | PAA2 solution | PAA2 solution |
| Sixth solution | — | — | PAH1 solution | PAH1 solution |
| Seventh solution | — | — | PAA2 solution | PAA2 solution |
| Eighth solution | — | — | PAH1 solution | PAH1 solution |
| Ninth solution | — | — | PAA2 solution | PAA2 solution |
| Transparency | A | A | A | A |
| Water content (%) | 36 | 37 | 37 | <1 |
| Water wettability | — | — | — | E |
| Dynamic contact angle (Advancing angle) | 38 | 41 | 53 | 95 |
| Tensile elastic modulus (kPa) | 825 | 657 | 593 | 740 |
| Tensile elongation (%) | 171 | 192 | 315 | 492 |
| Lubricity | — | — | — | D |
| Adhesion of mucin | — | — | — | — |
| Adhesion of lipid | — | — | — | D |
| Artificial lacrimal fluid immersion test | — | — | — | E |
| Degree of pigmentation | A | A | A | A |
| Surface friction coefficient (MIUa) | 0.305 | 0.781 | 0.968 | 0.601 |
| Surface friction coefficient (MIUb) | 0.350 | — | — | 1.680 |
| Surface friction coefficient ratio (Qa) | 1.000 | 2.560 | 3.175 | 1.970 |

TABLE 3-continued

|  | Comparative Example 5 | Comparative Example 6 | Comparative Example 7 | Comparative Example 8 |
|---|---|---|---|---|
| Surface friction coefficient ratio (Qb) | 1.148 | — | — | 5.508 |
| Qb − Qa | 0.148 | — | — | 3.538 |
| Boiling resistance | — | — | — | E |
| Scrubbing resistance | — | — | — | E |
| Comfort | B | B | C | — |
| Oxygen permeability [$10^{-11}$ (cm$^2$/sec) (mL · hPa)] | — | — | — | — |

Comparative Example 5

A commercially available silicone hydrogel soft contact lens product "ACUVUE® OASYS" (Johnson & Johnson Company) was evaluated. The evaluation results are shown in Table 3.

Comparative Example 6

The base material C (Reference Example 4) was immersed in a first solution (PAA solution) for 30 minutes and then respectively immersed in three pure water baths for 5 minutes. Next, the base material was immersed in a second solution (PEI solution) for 30 minutes and then respectively immersed in three pure water baths for 5 minutes. Next, the base material was immersed in a third solution (CPDA solution) for 30 minutes and then respectively immersed in three pure water baths for 5 minutes. The obtained base material was put in a glass bottle filled with a borate buffer. After sealing, an autoclave treatment (at 121° C. for 30 minutes) was carried out to obtain a low water content soft contact lens. The evaluation results of the obtained silicone hydrogel soft contact lens are shown in Table 3.

Comparative Example 7

The base material C (Reference Example 4) was subjected to coating E disclosed in Example 4 of Kohyo (National Publication of Translated Version) No. 2005-538418. Coating E means that coating is carried out in the order of PAA/PAH/PAA/PAH/PAA/PAH/PAA/PAH/PAA when polyacrylic acid is written as PAA and poly(allylamine hydrochloride) is written as PAH. Specifically, (a) the base material B is immersed in a PAA1 solution (0.01M, pH 2.5) for 30 minutes to form an innermost layer. Then, (b) the obtained base material C is immersed in a PAH1 solution (0.0001M, pH 2.5) for 5 minutes without subjecting to rinsing. Furthermore, (c) the obtained base material C is immersed in a PAA2' solution (0.0001M, pH 2.5) for 5 minutes without subjecting to rinsing. (d) The obtained base material C is further repeatedly subjected to the steps (b) and (c) three times to obtain a base material C coated by coating E. This base material C coated by coating E was put in a glass bottle filled with a borate buffer. After sealing, an autoclave treatment (at 121° C. for 30 minutes) was carried out to obtain a low water content soft contact lens. The evaluation results of the obtained silicone hydrogel soft contact lens are shown in Table 3.

Comparative Example 8

In the same manner as in Comparative Example 1, the base material $A_F$ (Reference Example 2) was subjected to coating C disclosed in Example 4 of Kohyo (National Publication of Translated Version) No. 2005-538418. Namely, coating was carried out in the order of PAA/PAH/PAA/PAH/PAA/PAH/PAA/PAH/PAA. The obtained base material was put in a glass bottle filled with a borate buffer. After sealing, an autoclave treatment (at 121° C. for 30 minutes) was carried out to obtain a medical device. The evaluation results of the obtained medical device are shown in Table 3.

Example 12

A quartz resonator sensor (resonance frequency 9 MHz, AT-cut, gold electrode) was immersed in a PAA solution for 30 minutes, respectively immersed in three pure water baths (each 100 mL) for 1 minute and dried by blowing a dry nitrogen gas, and then a resonance frequency ($F_1$) was measured by QCM (fundamental frequency of 27 MHz, at room temperature (about 25° C.)). Next, the quartz resonator sensor was immersed in a PEI solution for 30 minutes immersed, respectively immersed in (each 100 mL) for 1 minute and dried by blowing a dry nitrogen gas, and then a resonance frequency ($F_2$) was measured by QCM (fundamental frequency of 27 MHz, at room temperature (about 25° C.)). Next, the quartz resonator sensor was immersed in a PAA solution for 30 minutes, respectively immersed in three pure water baths (each 100 mL) for 1 minute and dried by blowing a dry nitrogen gas, and then a resonance frequency ($F_3$) was measured by QCM (fundamental frequency of 27 MHz, at room temperature (about 25° C.)). The measurement results are shown in Table 4.

TABLE 4

|  | Example 12 | Example 13 | Example 14 | Example 15 | Comparative Example 9 | Comparative Example 10 | Comparative Example 11 | Reference Example 13 |
|---|---|---|---|---|---|---|---|---|
| First solution | PAA solution | PAA solution | PAA solution | PAA solution | PAA2 solution | PAA1 solution | CPDA1 solution | PAA solution |
| Second solution | PEI solution | PEI solution | PEI solution | PEI solution | PAH1 solution | PAH1 solution | PAH1 solution | PEI solution |
| Third solution | PAA solution | CPDA solution | CPVPA solution | CPHA solution | PAA2 solution | PAA2 solution | CPDA2 solution | AcOH solution |
| Fourth solution | — | — | — | — | PAH1 solution | PAH1 solution | PAH1 solution | — |

TABLE 4-continued

| | Example 12 | Example 13 | Example 14 | Example 15 | Comparative Example 9 | Comparative Example 10 | Comparative Example 11 | Reference Example 13 |
|---|---|---|---|---|---|---|---|---|
| Fifth solution | — | — | — | — | PAA2 solution | PAA2 solution | CPDA2 solution | — |
| Sixth solution | — | — | — | — | PAH1 solution | PAH1 solution | PAH1 solution | — |
| Seventh solution | — | — | — | — | PAA2 solution | PAA2 solution | CPDA2 solution | — |
| Eighth solution | — | — | — | — | PAH1 solution | PAH1 solution | PAH1 solution | — |
| Ninth solution | — | — | — | — | PAA2 solution | PAA2 solution | CPDA2 solution | — |
| Resonance frequency ($F_1$) | 26878708 | 26903622 | 26912496 | 26916061 | 26888476 | 26891463 | 26907983 | 26879772 |
| Resonance frequency ($F_2$) | 26881050 | 26906193 | 26914575 | 26917831 | 26888432 | 26891505 | 26908198 | 26881631 |
| Resonance frequency ($F_3$) | 26884041 | 26911702 | 26919222 | 26923470 | 26888510 | 26891447 | 26908219 | 26881071 |
| Resonance frequency ($F_4$) | — | — | — | — | 26888559 | 26891433 | 26908365 | — |
| Resonance frequency ($F_5$) | — | — | — | — | 26888645 | 26891489 | 26908441 | — |
| Resonance frequency ($F_6$) | — | — | — | — | 26888593 | 26891507 | 26908746 | — |
| Resonance frequency ($F_7$) | — | — | — | — | 26889171 | 26891437 | 26908908 | — |
| Resonance frequency ($F_8$) | — | — | — | — | 26889155 | 26891382 | 26909054 | — |
| Resonance frequency ($F_9$) | — | — | — | — | 26889260 | 26891449 | 26909099 | — |
| $F_2 - F_1$ | 2342 | 2571 | 2079 | 1770 | −44 | 42 | 215 | 1859 |
| $F_3 - F_2$ | 2991 | 5509 | 4647 | 5639 | 78 | −58 | 21 | −620 |
| $F_4 - F_3$ | — | — | — | — | 49 | −14 | 146 | — |
| $F_5 - F_4$ | — | — | — | — | 86 | 56 | 76 | — |
| $F_6 - F_5$ | — | — | — | — | −52 | 18 | 305 | — |
| $F_7 - F_6$ | — | — | — | — | 578 | −70 | 162 | — |
| $F_8 - F_7$ | — | — | — | — | −16 | −55 | 146 | — |
| $F_9 - F_8$ | — | — | — | — | 105 | 67 | 45 | — |

Examples 13 to 15

Using the first to third solutions shown in Table 4, resonance frequencies $F_1$ to $F_3$ were measured in the same manner as in Example 12. The respective measurement results of Examples 13 to 15 are shown in Table 4.

Comparative Example 9

The method equivalent to coating C in Example 4 of Kohyo (National Publication of Translated Version) No. 2005-538418 as shown in Table 4 was carried out. Specifically, a quartz resonator sensor (resonance frequency 9 MHz, AT-cut, gold electrode) was immersed in a PAA2 solution for 30 minutes, respectively immersed in three pure water baths (each 100 mL) for 1 minute and dried by blowing a dry nitrogen gas, and then a resonance frequency ($F_1$) was measured by QCM (fundamental frequency of 27 MHz, at room temperature (about 25° C.)). Next, the quartz resonator sensor was immersed in a PAH1 solution for 5 minutes immersed, respectively immersed in (each 100 mL) for 1 minute and dried by blowing a dry nitrogen gas, and then a resonance frequency ($F_2$) was measured by QCM (fundamental frequency of 27 MHz, at room temperature (about 25° C.)). Next, the quartz resonator sensor was immersed in a PAA2 solution for 5 minutes, respectively immersed in three pure water baths (each 100 mL) for 1 minute and dried by blowing a dry nitrogen gas, and then a resonance frequency ($F_3$) was measured by QCM (fundamental frequency of 27 MHz, at room temperature (about 25° C.)). Hereinafter, in the same manner, the quartz resonator sensor was immersed in fourth to ninth solutions shown in Table 4 for 5 minutes, washed with pure water and dried by a dry nitrogen gas, and resonance frequencies $F_4$ to $F_9$ were measured. The measurement results are shown in Table 4.

Comparative Example 10

In the same manner as in Comparative Example 8, the method equivalent to coating C disclosed in Example 4 of Kohyo (National Publication of Translated Version) No. 2005-538418 was carried out. Using first to ninth solutions shown in Table 4, resonance frequencies $F_1$ to $F_9$ were measured in the same manner as in Comparative Example 9. The measurement results are shown in Table 4.

Comparative Example 11

In the same manner as in Comparative Example 8, the method equivalent to coating E disclosed in Example 4 of Kohyo (National Publication of Translated Version) No. 2005-538418 was carried out. Using first to ninth solutions shown in Table 4, resonance frequencies $F_1$ to $F_9$ were measured in the same manner as in Comparative Example 9. The measurement results are shown in Table 4.

Reference Example 13

Using first to third solutions shown in Table 4, resonance frequencies $F_1$ to $F_3$ were measured in the same manner as in Comparative Example 12. The measurement results are shown in Table 4.

Reference Example 6

Polydimethylsiloxane having a methacryloyl group at both ends (FM7726, JNC, mass average molecular weight of 29 kD, number average molecular weight of 26 kD) (50 parts by mass), as a component A, represented by the following formula (M2):

[Chemical Formula 12]

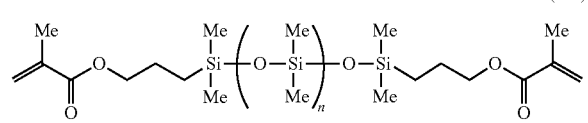

(M2)

trifluoroethyl acrylate (Viscoat 3F, Osaka Organic Chemical Industry Ltd.) (46 parts by mass) as a component B, methyl methacrylate (3 parts by mass) as a component C, an ultraviolet absorber having a polymerizable group (RUVA-93, Otsuka Chemical Co., Ltd.) (1 part by mass) as a component C, a polymerization initiator "IRGACURE®" 819 (Ciba Specialty Chemicals Inc., 0.75 part by mass) as a component C, and t-amyl alcohol (10 parts by mass) were mixed and then stirred to obtain a uniformly transparent monomer mixture.

This monomer mixture was charged in a test tube and degassing was carried out under reduced pressure of 20 Torr (27 hPa) while stirring using a touch mixer, and then the pressure was returned to atmospheric pressure using an argon gas. This operation was repeated three times. Then, in a glove box under a nitrogen atmosphere, the monomer mixture was injected into a mold for front curve (FC) made of a transparent resin (poly-4-methylpentene-1), and then a light shielding material composed of a black polyethylene terephthalate film, including a light shielding portion (diameter of 8.0 mm) and an opening (diameter of 1.5 mm) in the light shielding portion body was put therein. A monomer mixture was further added thereon, and the position of the light shielding material was adjusted to the center of the mold using tweezers.

A base curve (BC) mold was placed thereon and, when the light shielding material is shifted from the center of the mold, the position of BC mold was adjusted by rotation. Using a fluorescent lamp (Toshiba Corporation, FL-6D, quasi-daylight, 6 W, 4 lamps), the monomer mixture was polymerized by irradiation with light (8,000 lux, 20 minutes). After turning the mold over, the monomer mixture was further polymerized by irradiation with light for 20 minutes. After polymerization, the mold was removed using a jig and the mold was heated to 60° C. by immersing in an aqueous 100% by mass isopropyl alcohol solution. After 30 minutes, a contact lens-shaped molding was removed from the mold. The obtained molding was extracted by immersing in a large excess amount of an aqueous 100% by mass isopropyl alcohol solution at 60° C. for 2 hours. After extraction, the lens was placed on Kimwipe and transferred to a tray after drying. The obtained molding included an edge portion having a diameter of about 14 mm and a center portion having a thickness of about 0.07 mm.

Reference Example 7

Polydimethylsiloxane having a methacryloyl group at both ends (FM7726, CHISSO CORPORATION, the above-mentioned compound of the formula (M2), mass average molecular weight of 29 kD, number average molecular weight of 26 kD) (49 parts by mass) as a component A, trifluoroethyl acrylate (Viscoat 3F, Osaka Organic Chemical Industry Ltd.) (45 parts by mass) as a component B, 2-ethylhexyl acrylate (5 parts by mass) as a component C, N,N-dimethylacrylamide (1 part by mass) as a component C, an ultraviolet absorber having a polymerizable group (RUVA-93, Otsuka Chemical Co., Ltd.) (1 part by mass) as a component C, a colorant having a polymerizable group [(Uniblue A, Sigma-Aldrich Corporation, the formula (M3)] (0.1 part by mass) as a component C, a polymerization initiator "IRGACURE®" 819 (Ciba Specialty Chemicals Inc., 0.75 part by mass), and t-amyl alcohol (10 parts by mass) were mixed and then stirred. The mixture was filtered through a membrane filter (0.45 μm) to remove an insoluble matter, thus obtaining a monomer mixture.

This monomer mixture was charged in a test tube and degassing was carried out under reduced pressure of 20 Torr (27 hPa) while stirring using a touch mixer, and then the pressure was returned to atmospheric pressure using an argon gas. This operation was repeated three times. In a glove box under a nitrogen atmosphere, the monomer mixture was injected into a mold for contact lens made of a transparent resin (poly-4-methylpentene-1) and then polymerized by irradiating with light (8,000 lux, 20 minutes) using a fluorescent lamp (Toshiba Corporation, FL-6D, quasi-daylight, 6 W, 4 lamps). After polymerization, the whole mold was immersed in an aqueous 60% by mass isopropyl alcohol solution and a contact lens-shaped molding was removed from the mold. The obtained molding was immersed in a large excess amount of an aqueous 80% by mass isopropyl alcohol solution at 60° C. for 2 hours. After extraction, the lens was placed on Kimwipe and transferred to a tray after drying. The obtained molding included an edge portion having a diameter of about 14 mm and a center portion having a thickness of about 0.07 mm.

Furthermore, the molding was immersed in a large excess amount of an aqueous 50% by mass isopropyl alcohol solution at room temperature for 30 minutes, followed by immersion in a large excess amount of an aqueous 25% by mass isopropyl alcohol solution at room temperature for 30 minutes, and further immersion in a large excess amount of pure water at room temperature for 30 minutes. Finally, the molding immersed in clean pure water was put in a closed vial bottle, and then autoclave sterilization was carried out at 121° C. for 30 minutes. The obtained molding had a water content of less than 1%.

In order to measure oxygen permeability of this molding of Reference Example 7, a film-shaped sample measuring 60 mm×60 mm×0.25 mm was obtained in the same manner as mentioned above, except that two glass plates and a spacer (also serving as a gasket) are used in place of the above-mentioned mold. This sample has oxygen permeability of $380 \times 10^{-11}$ [(cm$^2$/sec) mLO$_2$/(mL·hPa)] (510 Barrer), which was a very high value as a material for a lens for eye.

Reference Example 8

An iris pattern 410 of FIG. 4 was printed on a front curve surface of the molding (contact lens) obtained in Reference Example 7 to obtain a contact lens-shaped sample. The printed iris pattern had a diameter of about 11 mm. An optically transparent portion of a center portion of the iris pattern had a maximum diameter of about 6.5 mm. The obtained molding includes an edge portion having a diameter of about 14 mm and a center portion having a thickness of about 0.07 mm.

Reference Example 9

An iris pattern 420 of FIG. 5 was printed on a front curve surface of the molding (contact lens) obtained in Reference Example 7 to obtain a contact lens-shaped sample. The printed iris pattern had a diameter of about 8.0 mm, and an optical pupil had a diameter of about 1.35 mm.

Reference Example 10

Polydimethylsiloxane having a methacryloyl group at both ends (FM7726, CRISSO CORPORATION, a compound of the above-mentioned formula (M2) as a component A, mass average molecular weight of 29 kD, number average molecular weight of 26 kD) (50 parts by mass), trifluoroethyl acrylate (Viscoat 3F, Osaka Organic Chemical Industry Ltd.) (46 parts by mass) as a component B, methyl (meth)acrylate (3 parts by mass) as a component C, an ultraviolet absorber having a polymerizable group (RUVA-93, Otsuka Chemical Co., Ltd.) (1 part by mass) as a component C, a polymerization initiator "IRGACURE®" 819 (Ciba Specialty Chemicals Inc., 0.75 part by mass) as a component C, and t-amyl alcohol (10 parts by mass) were mixed and then stirred to obtain a uniformly transparent monomer mixture.

This monomer mixture was charged in a test tube and degassing was carried out under reduced pressure of 20 Torr (27 hPa) while stirring using a touch mixer, and then the pressure was returned to atmospheric pressure using an argon gas. This operation was repeated three times. Thereafter, in a glove box under a nitrogen atmosphere, the monomer mixture was injected into a FC mold for contact lens made of a transparent resin (poly-4-methylpentene-1). A BC mold for contact lens was placed thereon. Using a fluorescent lamp (Toshiba Corporation, FL-6D, quasi-daylight, 6 W, 4 lamps), the monomer mixture was polymerized by irradiation with light (8,000 lux, 20 minutes). The BC mold was removed and an iris pattern 410 (which is the same as that of Reference Example 8) of FIG. 4 was printed on a lens surface. The monomer mixture was further charged thereon. The BC mold was placed, followed by polymerization by irradiating with light for 20 minutes. After polymerization, the mold was removed using a jig. The mold was warmed at 60° C. by immersing in an aqueous 100% by mass isopropyl alcohol solution. After 30 minutes, a contact lens-shaped molding was removed from the mold. The obtained molding was extracted by immersing in a large excess amount of an aqueous 100% by mass isopropyl alcohol solution at 60° C. for 2 hours. After extraction, the lens was placed on Kimwipe and transferred to a tray after drying. The obtained lens included an edge portion having a diameter of about 14 mm and a center portion having a thickness of about 0.07 mm.

Reference Example 11

The same operation as in Reference Example 10 was carried out, except for replacing by the iris pattern 420 (which is the same as that of Reference Example 9) of FIG. 5, a lens was produced. The obtained lens includes an edge portion having a diameter of about 14 mm and a center portion having a thickness of about 0.07 mm.

Example 16

The molding obtained in Reference Example 6 was immersed in a PAA solution at room temperature for 30 minutes and then lightly rinsed with pure water in a beaker. The molding was transferred to a beaker containing fresh pure water and then exposed to ultrasonic using a ultrasonic cleaner (for 30 seconds). Furthermore, the molding was lightly rinsed in a beaker containing fresh pure water. Then, the same operation was repeated in the order of a PEI solution and a p (DMAA/AA) solution. After completion of the coating operation, the coated lens was put in a closed vial bottle in a state of being wetted with a borate buffer, and then subjected to autoclave sterilization at 121° C. for 30 minutes, thus obtaining a lens which causes less feeling of dryness and includes pinholes, and also enable distal and proximal focusing. The evaluation results of physical properties of the obtained lens are shown in Table 5. The lens was left to stand at 23° C. under humidity condition of 60% for 24 hours. As a result, neither shrinkage nor deformation of the lens was recognized.

TABLE 5

| | | | | | Evaluation results | | | | | |
| | Molding | First solution | Second solution | Third solution | Lubricity | Water wettability | Water content (%) | Tensile elastic modulus (kPa) | Tensile elongation (%) | Scrubbing resistance-RN |
|---|---|---|---|---|---|---|---|---|---|---|
| Example 16 | Reference Example 6 | PAA solution | PEI solution | P(DMAA/AA) solution | A | B | Less than 1 | — | — | C |
| Example 17 | Reference Example 8 | PAA solution | PEI solution | P(DMAA/AA) solution | A | B | Less than 1 | 669 | 488 | C |
| Example 18 | Reference Example 9 | PAA solution | PEI solution | P(DMAA/AA) solution | A | B | Less than 1 | 662 | 490 | C |
| Example 19 | Reference Example 10 | PAA solution | PEI solution | P(DMAA/AA) solution | A | B | Less than 1 | 641 | 502 | C |
| Example 20 | Reference Example 11 | PAA solution | PEI solution | P(DMAA/AA) solution | A | B | Less than 1 | 676 | 493 | C |
| Comparative Example 13 | Reference Example 6 | — | — | — | E | E | Less than 1 | — | — | E |
| Comparative | Reference | — | — | — | E | E | Less | 641 | 456 | E |

TABLE 5-continued

| | Molding | First solution | Second solution | Third solution | Lubricity | Water wettability | Water content (%) | Tensile elastic modulus (kPa) | Tensile elongation (%) | Scrubbing resistance-RN |
|---|---|---|---|---|---|---|---|---|---|---|
| Example 14 | Example 8 | | | | | | than 1 | | | |
| Comparative Example 15 | Reference Example 9 | — | — | — | E | E | Less than 1 | 662 | 502 | E |
| Comparative Example 16 | Reference Example 10 | — | — | — | E | E | Less than 1 | 669 | 506 | E |
| Comparative Example 17 | Reference Example 11 | — | — | — | E | E | Less than 1 | 697 | 481 | E |

Example 17

The molding obtained in Reference Example 8 was immersed in a PAA solution at room temperature for 30 minutes, and then lightly rinsed with pure water in a beaker. The molding was transferred to a beaker containing fresh pure water and then exposed to ultrasonic using a ultrasonic cleaner (for 30 seconds). Furthermore, the molding was lightly rinsed in a beaker containing fresh pure water. Then, the same operation was repeated in the order of a PEI solution and a p (DMAA/AA) solution. After completion of the coating operation, the coated lens was put in a closed vial bottle in a state of being wetted with a borate buffer, and then subjected to autoclave sterilization at 121° C. for 30 minutes, thus obtaining a lens which causes less feeling of dryness and exaggerates the wearer's pupil, and also has satisfactory design properties. The evaluation results of physical properties of the obtained lens are shown in Table 5. The lens was left to stand under the conditions of 23° C. and 60% humidity for 24 hours. As a result, neither shrinkage nor deformation of the lens was recognized.

Example 18

The molding obtained in Reference Example 9 was immersed in a PAA solution at room temperature for 30 minutes, and then lightly rinsed with pure water in a beaker. The molding was transferred to a beaker containing fresh pure water and then exposed to ultrasonic using a ultrasonic cleaner (for 30 seconds). Furthermore, the molding was lightly rinsed in a beaker containing fresh pure water. Then, the same operation was repeated in the order of a PEI solution and a p (DMAA/AA) solution. After completion of the coating operation, the coated lens was put in a closed vial bottle in a state of being wetted with a borate buffer, and then subjected to autoclave sterilization at 121° C. for 30 minutes, thus obtaining a lens which causes less feeling of dryness and includes pinholes, and also enable distal and proximal focusing. The evaluation results of physical properties of the obtained lens are shown in Table 5. The lens was left to stand under the conditions of 23° C. and 60% humidity for 24 hours. As a result, neither shrinkage nor deformation of the lens was recognized.

Example 19

The molding (lens) obtained in Reference Example 10 was immersed in a PAA solution at room temperature for 30 minutes, and then lightly rinsed with pure water in a beaker. The molding was transferred to a beaker containing fresh pure water and then exposed to ultrasonic using a ultrasonic cleaner (for 30 seconds). Furthermore, the molding was lightly rinsed in a beaker containing fresh pure water. Then, the same operation was repeated in the order of a PEI solution and a p (DMAA/AA) solution. After completion of the coating operation, the coated lens was put in a closed vial bottle in a state of being wetted with a borate buffer, and then subjected to autoclave sterilization at 121° C. for 30 minutes, thus obtaining a lens which causes less feeling of dryness and exaggerates the wearer's pupil, and also has satisfactory design properties. The evaluation results of physical properties of the obtained lens are shown in Table 5. The lens was left to stand under the conditions of 23° C. and 60% humidity for 24 hours. As a result, neither shrinkage nor deformation of the lens was recognized.

Example 20

The molding (lens) obtained in Reference Example 11 was immersed in a PAA solution at room temperature for 30 minutes, and then lightly rinsed with pure water in a beaker. The molding was transferred to a beaker containing fresh pure water and then exposed to ultrasonic using a ultrasonic cleaner (for 30 seconds). Furthermore, the molding was lightly rinsed in a beaker containing fresh pure water. Then, the same operation was repeated in the order of a PEI solution and a p (DMAA/AA) solution. After completion of the coating operation, the coated lens was put in a closed vial bottle in a state of being wetted with a borate buffer, and then subjected to autoclave sterilization at 121° C. for 30 minutes, thus obtaining a lens which causes less feeling of dryness and includes pinholes, and also enable distal and proximal focusing. The evaluation results of physical properties of the obtained lens are shown in Table 5. The lens was left to stand under the conditions of 23° C. and 60% humidity for 24 hours. As a result, neither shrinkage nor deformation of the lens was recognized.

Reference Example 14

The molding obtained in Reference Example 7 was immersed in a PAA solution at room temperature for 30 minutes, and then lightly rinsed with pure water in a beaker. The molding was transferred to a beaker containing fresh pure water and then exposed to ultrasonic using a ultrasonic cleaner (for 30 seconds). Furthermore, the molding was lightly rinsed in a beaker containing fresh pure water. Then, the same operation was repeated in the order of a PEI solution and a p (DMAA/AA) solution. After completion of the coating operation, the coated lens was put in a closed vial bottle in a state of being wetted with a borate buffer, and then subjected to autoclave sterilization at 121° C. for 30 minutes. In Reference Example 14, a fixed focal length lens having poor design properties was obtained. The evaluation results of physical properties of the obtained lens are shown in Table 5. The lens was left to stand under the conditions of 23° C. and 60% humidity for 24 hours. As a result, neither shrinkage nor deformation of the lens was recognized.

Comparative Example 12

Subjects A and B wore a commercially available color contact lens (water content: 58%) for 6 hours. Both subjects A and B felt dryness of eyes and did not feel comfort. The lens was left to stand under the conditions of 23° C. and 60% humidity for 24 hours. As a result, the lens underwent shrinkage leading to generation of wrinkles, resulting in deformation because of vaporization of moisture.

Comparative Example 13

The molding obtained in Reference Example 6 was immersed in an aqueous 1% by mass PVP K90 solution (polyvinylpyrrolidone, Sigma-Aldrich Japan, molecular weight of 360,000) at room temperature for 30 minutes and taken out from the solution, followed by touch with a finger of a person. As a result, the molding had excellent lubricity. The lubricity was rated "A" according to criteria for evaluation of lubricity. Thereafter, the molding was lightly rinsed with pure water in a beaker, followed by touch with a finger of a person. As a result, the molding had no lubricity. The lubricity was rated "E" according to criteria for evaluation of lubricity. The evaluation results of other physical properties of this lens are shown in Table 5.

Comparative Example 14

The molding obtained in Reference Example 8 was immersed in an aqueous 1% by mass PVP K90 solution (polyvinylpyrrolidone, Sigma-Aldrich Japan, molecular weight of 360,000) at room temperature for 30 minutes and taken out from the solution, followed by touch with a finger of a person. As a result, the molding had excellent lubricity. The lubricity was rated "A" according to criteria for evaluation of lubricity. Thereafter, the molding was lightly rinsed with pure water in a beaker, followed by touch with a finger of a person. As a result, the molding had no lubricity. The lubricity was rated "E" according to criteria for evaluation of lubricity. The evaluation results of other physical properties of this lens are shown in Table 5.

Comparative Example 15

The molding obtained in Reference Example 9 was immersed in an aqueous 1% by mass PVP K90 solution (polyvinylpyrrolidone, Sigma-Aldrich Japan, molecular weight of 360,000) at room temperature for 30 minutes and taken out from the solution, followed by touch with a finger of a person. As a result, the molding had excellent lubricity. The lubricity was rated "A" according to criteria for evaluation of lubricity. Thereafter, the molding was lightly rinsed with pure water in a beaker, followed by touch with a finger of a person. As a result, the molding had no lubricity. The lubricity was rated "E" according to criteria for evaluation of lubricity. The evaluation results of other physical properties of this lens are shown in Table 5.

Comparative Example 16

The molding (lens) obtained in Reference Example 10 was immersed in an aqueous 1% by mass PVP K90 solution (polyvinylpyrrolidone, Sigma-Aldrich Japan, molecular weight of 360,000) at room temperature for 30 minutes and taken out from the solution, followed by touch with a finger of a person. As a result, the molding had excellent lubricity. The lubricity was rated "A" according to criteria for evaluation of lubricity. Thereafter, the molding was lightly rinsed with pure water in a beaker, followed by touch with a finger of a person. As a result, the molding had no lubricity. The lubricity was rated "E" according to criteria for evaluation of lubricity. The evaluation results of other physical properties of this lens are shown in Table 5.

Comparative Example 17

The molding (lens) obtained in Reference Example 11 was immersed in an aqueous 1% by mass PVP K90 solution (polyvinylpyrrolidone, Sigma-Aldrich Japan, molecular weight of 360,000) at room temperature for 30 minutes and taken out from the solution, followed by touch with a finger of a person. As a result, the molding had excellent lubricity. The lubricity was rated "A" according to criteria for evaluation of lubricity. Thereafter, the molding was lightly rinsed with pure water in a beaker, followed by touch with a finger of a person. As a result, the molding had no lubricity. The lubricity was rated "E" according to criteria for evaluation of lubricity. The evaluation results of other physical properties of this lens are shown in Table 5.

Examples 21 to 40 and Comparative Example 18

Using base materials mentioned in Table 6, imparting of an iris pattern and a surface treatment were carried out by the method disclosed in the respective Reference Examples in Table 6 to obtain contact lenses. The evaluation results are shown in Table 6.

TABLE 6

|  | Molding | Imparting of iris pattern | Surface treatment | Comfort |
| --- | --- | --- | --- | --- |
| Example 21 | Base material A | Reference Example 8 | Example 1 | A |
| Example 22 | Base material A | Reference Example 8 | Example 2 | A |
| Example 23 | Base material A | Reference Example 8 | Example 3 | A |
| Example 24 | Base material A | Reference Example 8 | Example 4 | B |
| Example 25 | Base material A | Reference Example 8 | Comparative Example 1 | — |
| Example 26 | Base material A | Reference Example 8 | Comparative Example 2 | — |
| Example 27 | Base material A | Reference Example 8 | Reference Example 12 | — |
| Example 28 | Base material A | Reference Example 8 | Comparative Example 3 | — |
| Example 29 | Base material A | Reference Example 8 | Comparative Example 4 | — |
| Example 30 | Base material A | Reference Example 8 | Example 9 | — |
| Example 31 | Base material A | Reference Example 9 | Example 1 | A |

TABLE 6-continued

| | Molding | Imparting of iris pattern | Surface treatment | Comfort |
|---|---|---|---|---|
| Example 32 | Base material A | Reference Example 9 | Example 2 | A |
| Example 33 | Base material A | Reference Example 9 | Example 3 | A |
| Example 34 | Base material A | Reference Example 9 | Example 4 | — |
| Example 35 | Base material A | Reference Example 9 | Comparative Example 1 | — |
| Example 36 | Base material A | Reference Example 9 | Comparative Example 2 | — |
| Example 37 | Base material A | Reference Example 9 | Reference Example 12 | — |
| Example 38 | Base material A | Reference Example 9 | Comparative Example 3 | — |
| Example 39 | Base material A | Reference Example 9 | Comparative Example 4 | — |
| Example 40 | Base material A | Reference Example 9 | Example 9 | — |
| Comparative Example 18 | Base material C | Reference Example 8 | Example 1 | C |

Example 41

In accordance with the method for producing the base material A of Reference Example 2, a contact lens $A_1$ (including an edge portion having a diameter of about 13 mm and a center portion having a thickness of about 0.07 mm) including a plurality of through holes (having a diameter of 0.8 mm), like the lacrimal fluid exchange-promoting pattern 510 shown in FIG. 6, was obtained. In a stage after polymerization of a contact lens and before separation of a mold from a contact lens, the contact lens was perforated to form through holes together with the mold, using an exclusive punching die.

Example 42

In accordance with the method for producing the base material A of Reference Example 2, except for using a mold having an exclusive shape, a contact lens $A_2$ (including an edge portion having a diameter of about 13 mm and a center portion having a thickness of about 0.07 mm) including a plurality of through holes [having a major diameter (diameter) of 3 mm and a minor diameter of 0.8 mm], like the lacrimal fluid exchange-promoting pattern 520 shown in FIG. 7, was obtained.

Example 43

In accordance with the method for producing the base material A of Reference Example 2, except for using a mold having an exclusive shape, a contact lens $A_3$ (including an edge portion having a diameter of about 13 mm and a center portion having a thickness of about 0.07 mm) including a plurality of through holes [having a length of 4 mm and a width of 1 mm], like the lacrimal fluid exchange-promoting pattern 530 shown in FIG. 8, was obtained.

Comparative Example 19

In accordance with the method for producing the base material C of Reference Example 4, a contact lens $C_1$ (including an edge portion having a diameter of about 13 mm and a center portion having a thickness of about 0.07 mm) including a plurality of through holes (having a diameter of 0.8 mm), like the lacrimal fluid exchange-promoting pattern 510 shown in FIG. 6, was obtained. In a stage after polymerization of a contact lens and before separation of a mold from a contact lens, the contact lens was perforated to form through holes together with the mold, using an exclusive punching die.

Examples 44 to 73, Comparative Example 20, and Comparative Example 21

Using the contact lenses (or base materials) mentioned in Table 7 as base materials, a surface treatment was carried out by the method disclosed in the Reference Examples shown in Table 7 was carried out to obtain contact lenses. The evaluation results are shown in Table 7.

TABLE 7

| | | | Evaluation results | |
|---|---|---|---|---|
| | Base material | Surface treatment | Lacrimal fluid dynamics | Comfort |
| Example 44 | Contact lens $A_1$ | Example 1 | A | A |
| Example 45 | Contact lens $A_1$ | Example 2 | A | A |
| Example 46 | Contact lens $A_1$ | Example 3 | A | A |
| Example 47 | Contact lens $A_1$ | Example 4 | A | B |
| Example 48 | Contact lens $A_1$ | Comparative Example 1 | — | — |
| Example 49 | Contact lens $A_1$ | Comparative Example 2 | — | — |
| Example 50 | Contact lens $A_1$ | Reference Example 12 | — | — |
| Example 51 | Contact lens $A_1$ | Comparative Example 3 | — | — |
| Example 52 | Contact lens $A_1$ | Comparative Example 4 | — | — |
| Example 53 | Contact lens $A_1$ | Example 9 | — | — |
| Example 54 | Contact lens $A_2$ | Example 1 | A | A |
| Example 55 | Contact lens $A_2$ | Example 2 | A | A |
| Example 56 | Contact lens $A_2$ | Example 3 | A | A |
| Example 57 | Contact lens $A_2$ | Example 4 | — | — |
| Example 58 | Contact lens $A_2$ | Comparative Example 1 | — | — |
| Example 59 | Contact lens $A_2$ | Comparative Example 2 | — | — |
| Example 60 | Contact lens $A_2$ | Reference Example 12 | — | — |
| Example 61 | Contact lens $A_2$ | Comparative Example 3 | — | — |
| Example 62 | Contact lens $A_2$ | Comparative Example 4 | — | — |
| Example 63 | Contact lens $A_2$ | Example 9 | — | — |
| Example 64 | Contact lens $A_3$ | Example 1 | A | A |

TABLE 7-continued

| | Base material | Surface treatment | Evaluation results | |
| --- | --- | --- | --- | --- |
| | | | Lacrimal fluid dynamics | Comfort |
| Example 65 | Contact lens $A_3$ | Example 2 | A | A |
| Example 66 | Contact lens $A_3$ | Example 3 | A | A |
| Example 67 | Contact lens $A_3$ | Example 4 | — | — |
| Example 68 | Contact lens $A_3$ | Comparative Example 1 | — | — |
| Example 69 | Contact lens $A_3$ | Comparative Example 2 | — | — |
| Example 70 | Contact lens $A_3$ | Reference Example 12 | — | — |
| Example 71 | Contact lens $A_3$ | Comparative Example 3 | — | — |
| Example 72 | Contact lens $A_3$ | Comparative Example 4 | — | — |
| Example 73 | Contact lens $A_3$ | Example 9 | — | — |
| Comparative Example 20 | Contact lens $C_2$ | Example 2 | A | C |
| Comparative Example 21 | Base material A | Example 2 | B | A |

The present invention relates to a medical device, a combination of coating solutions for applying to this medical device, and a method for producing a medical device, and the medical device can be suitably used as a device which is contacted with a body surface including a body fluid or the like, or a device which is introduced into the body, for example, a lens for eye and a skin material. The medical device is particularly useful as a low water content soft lens for eye, for example, a lens for eye, such as a soft contact lens, an intraocular lens, an artificial cornea, a corneal inlay, a corneal onlay, or a spectacle lens. The medical device is particularly suitable as a low water content soft contact lens which is used in orthoptic and cosmetic applications.

REFERENCE SIGNS LIST

1 Apparatus
10 Sample stand
10a Quartz glass plate
11 Measurement jig (made of aluminum)
12 Friction detection unit
13 Dynamometer
20 Friction block
21 Mount holder (made of aluminum)
22 Packing (made of "Teflon®")
23 Nut (made of aluminum)
S Sample
41, 42 Low water content soft lens for eye
410, 420 Iris pattern
421 Optical pupil
51, 52, 53 Low water content soft contact lens
510, 520, 530 Lacrimal fluid exchange-promoting pattern
511, 521 Through hole
531 Groove

The invention claimed is:
1. A medical device having:
an elastic modulus of 100 kPa or more and 2,000 kPa or less,
a water content of 5% by mass or less,
a tensile elongation of 50% or more and 3,000% or less, and
a dynamic contact angle (advancing angle) relative to a borate buffer of 80° or less, wherein a surface friction coefficient ratio (Qa) in a state of being wetted with a borate buffer is 0.8 or less,
provided that Qa=MIUa/MIUo:
where MIUa represents a coefficient of surface friction between the medical device and a smooth quartz glass plate in the state of being wetted with the borate buffer; and MIUo is 0.305,
wherein the medical device includes a base material, and a layer made of an acidic polymer and a basic polymer is formed on at least a part of a surface of the base material, at least one of the basic and the acidic polymers comprises a polymer having an amide bond selected from the group consisting of:
acidic polymers having an amide bond selected from a (meth)acrylic acid/N,N-dimethylacrylamide copolymer and a 2-acrylamido-2-methylpropanesulfonic acid/N,N-dimethylacrylamide copolymer, and
basic polymers having an amide bond selected from an N,N-dimethylaminoethyl methacrylate/N,N-dimethylacrylamide copolymer and an N,N-dimethylaminopropyl acrylamide/N,N-dimethylacrylamide copolymer; and
wherein the base material contains, as main components, a copolymer of the following components A and B:
component A: a polysiloxane compound which has a plurality of polymerizable functional groups per molecule, and also has a number average molecular weight of 6,000 or more, and
component B: a polymerizable monomer having a fluoroalkyl group.
2. The medical device according to claim 1, wherein a surface friction coefficient ratio (Qb) in a state of being wetted with a saline is 3 or less,
provided that Qb=MIUb/MIUo:
where MIUb represents a coefficient of surface friction between the medical device and a smooth quartz glass plate in the state of being wetted with the saline; and MIUo is 0.305.
3. The medical device according to claim 1, wherein a difference (Qb−Qa) between the surface friction coefficient ratio (Qb) in the state of being wetted with a saline and the surface friction coefficient ratio (Qa) in the state of being wetted with a borate buffer is 1.6 or less,
provided that Qa=MIUa/MIUo, and
Qb=MIUb/MIUo:
where MIUa represents a coefficient of surface friction between the medical device and a smooth quartz glass plate in the state of being wetted with the borate buffer; MIUb represents a coefficient of surface friction between the medical device and the smooth quartz glass plate in the state of being wetted with the saline; and MIUo is 0.305.

4. The medical device according to claim 1, wherein an iris-pattern being formed on at least a part of the medical device for an eye.

5. The medical device according to claim 4, wherein the pattern is a light shielding pattern having a circular ring shape, and an optical pupil having a diameter of 2.0 mm or less is formed in a center of the pattern.

6. The medical device according to claim 4, wherein the pattern covers a surface of an iris to thereby pseudo-color the iris.

7. The medical device according to claim 1, wherein a layer made of an acidic polymer and a basic polymer is formed on at least a part of the medical device for an eye, an iris pattern being formed on at least the part of the medical device for the eye.

8. The medical device according to claim 7, wherein the pattern is a light shielding pattern having a circular ring shape, and an optical pupil having a diameter of 2.0 mm or less is formed in a center of the pattern.

9. The medical device according to claim 7, wherein the pattern covers a surface of an iris to thereby pseudo-color the iris.

* * * * *